US008067391B2

(12) United States Patent
Korta et al.

(10) Patent No.: US 8,067,391 B2
(45) Date of Patent: *Nov. 29, 2011

(54) ODCASE INHIBITORS FOR THE TREATMENT OF MALARIA

(75) Inventors: Lakshmi P. Korta, Thornhill (CA); Emil F. Pai, Toronto (CA); Angelica M. Bello, Toronto (CA); Masahiro Fujihashi, Kyoto (JP)

(73) Assignee: University Health Network, Toronto, Ontario (CA)

( * ) Notice: Subject to any disclaimer, the term of this patent is extended or adjusted under 35 U.S.C. 154(b) by 233 days.

This patent is subject to a terminal disclaimer.

(21) Appl. No.: 12/089,120

(22) PCT Filed: Oct. 3, 2006

(86) PCT No.: PCT/CA2006/001620
§ 371 (c)(1),
(2), (4) Date: Apr. 23, 2009

(87) PCT Pub. No.: WO2007/038859
PCT Pub. Date: Apr. 12, 2007

(65) Prior Publication Data
US 2009/0221524 A1    Sep. 3, 2009

Related U.S. Application Data

(60) Provisional application No. 60/596,537, filed on Oct. 3, 2005, provisional application No. 60/597,142, filed on Nov. 12, 2005.

(51) Int. Cl.
*A01N 43/04* (2006.01)
*A61K 31/70* (2006.01)

(52) U.S. Cl. ............... 514/49; 514/42; 514/43; 514/50; 514/51; 514/52

(58) Field of Classification Search .................... None
See application file for complete search history.

(56) References Cited

U.S. PATENT DOCUMENTS

| | | | |
|---|---|---|---|
| 3,116,282 | A | 12/1963 | Hunter |
| 4,872,278 | A | 10/1989 | Ross et al. |
| 4,873,228 | A | 10/1989 | Schmalzl |
| 5,672,501 | A | 9/1997 | Matulic-Adamic et al. |
| 5,891,684 | A | 4/1999 | Usman et al. |
| 6,020,483 | A | 2/2000 | Beckvermit et al. |
| 6,130,035 | A | 10/2000 | Brusilow |
| 6,355,787 | B1 | 3/2002 | Beckvermit et al. |
| 6,927,026 | B1 | 8/2005 | Pompejus et al. |

FOREIGN PATENT DOCUMENTS

| | | |
|---|---|---|
| DE | 158613 | 1/1983 |
| EP | 0097373 | 1/1984 |
| JP | 05140179 | 6/1993 |
| WO | 9531541 | 11/1995 |
| WO | 9618736 | 6/1996 |
| WO | 9850530 | 11/1998 |
| WO | 0018780 | 4/2000 |
| WO | 0232920 | 4/2002 |
| WO | 02069903 | 9/2002 |
| WO | 03048222 | 6/2003 |
| WO | 03064621 | 8/2003 |
| WO | 03072757 | 9/2003 |
| WO | WO 03/072757 | 9/2003 |
| WO | 2004013300 | 2/2004 |
| WO | 2005020885 | 3/2005 |

OTHER PUBLICATIONS

Pragobpol, S.; Gero, A. M.; Lee, C. S.; O'Sullivan, W. J. Orotate phosphoribosyltransferase and orotidylate decarboxylase from *Crithidia luciliae*: Subcellular location of the enzymes and a study of substrate channeling. Arch. Biochem. Biophys. 1984, 230, 285-293.
Queen, Susan A. et al., "In Vitro Susceptibilities of *Plasmodium falciparum* to Compounds Which Inhibit Nucleotide Metabolism", Antimicrobial Agents and Chemotherapy (1990) vol. 34, No. 7, pp. 1393-1398.
Radzicka, A.; Wolfenden, R. A proficient enzyme. Science 1995, 267, 90-93.
Rathod, Pradipsinh K. et al., "Orotidylate-Metabolizing Enzymes of the Human Malarial Parasite, *Plasmodium falciparum*, Differ from Host Cell Enzymes", The Journal of Biological Chemistry (1983) vol. 258, No. 5, pp. 2852-2855.
Rathod et al., "Selective activity of 5-fluoroorotic acid against *Plasmodium Falciparum* in vitro" Antimicrob. Agents Chemother. Jul. 1989, vol. 33(7), pp. 1090-1094, (whole document).
Reichard, P. The enzymatic synthesis of pyrimidines. Adv. Enzymol. Mol. Biol. 1959, 21, 263-294.
Retallack D. M. et al., "The URA5 Gene is Necessary for *Histoplasma capsulatum* Growth during Infection of Mouse and Human Cells", Infection and Immunity (1999) vol. 67, No. 2, pp. 624-629.
Reyes P. et al., "Enzymes of Purine and Pyrimidine Metabolism from the Human Malaria Parasite, *Plasmodium falciparum*", Molecular Biochemistry Parasitol. (1982) vol. 5, No. 5, pp. 275-290. (Abstract).
San-Félix et al. Novel Series of TSAO-T Derivatives. Synthesis and Anti-HIV Activity of 4-,5-, and 6-Substituted Pyrimidine Analoges. J. Med. Chem. 37:453-460, 1994. Schutz A. G. R.; Konig, S.; Hubner, G.; Tittmann, K. Intermediates and transition states in thiamin diphosphate-dependent decarboxylases. A kinetic and NMR study on wild-type indolepyruvate decarboxylase and variants using indolepyruvate, benzoylformate, and pyruvate as substrates. Biochemistry 2005, 44, 6164-6179.
Scott, H. V.; Gero, A. M.; O'Sullivan, W. J. In vitro inhibition of *Plasmodium falciparum* by pyrazofurin, an inhibitor of pyrimidine biosynthesis de novo. Mol. Biochem. Parasitol. 1986, 18, 3-15. (Abstract).
Seymour, K. K.; Lyons, S. D.; Phillips, L.; Rieckmann, K. H.; Christopherson, R. I. Cytotoxic effects of inhibitors of de novo pyrimidine biosynthesis upon *Plasmodium falciparum*, Biochemistry 1994, 33, 5268-5274.

(Continued)

Primary Examiner — Patrick Lewis
(74) Attorney, Agent, or Firm — Rothwell, Figg, Ernst & Manbeck, P.C.

(57) ABSTRACT

The present invention includes methods of treating or preventing malaria by administering an anti-malarial effective amount of 6-substituted uridine derivatives to a subject need thereof. The invention also includes new 6-substituted uridine derivatives for use as therapeutics, in particular to treat malaria.

26 Claims, 7 Drawing Sheets

OTHER PUBLICATIONS

Sievers, A.; Wolfenden, R. Equilibrium of formation of the 6-carbanion of UMP, a potential intermediate in the action of OMP decarboxylase. J. Am. Chem. Soc. 2002, 124, 13986-13987.

Smee, D. F.; McKernan, P. A.; Nord, L. D.; Willis, R. C.; Petrie, C. R.; Riley, T. M.; Revankar, G. R.; Robins, R. K.; Smith, R. A. Novel pyrazolo[3,4-d]pyrimidine nucleoside analog with broad-spectrum antiviral activity. Antimicrob. Agents. Chemother. 1987, 31, 1535-1541.

Smiley, J. A.; Saleh, L. Active site probes for yeast OMP decarboxylase: Inhibition constants of UMP and thio-substituted UMP analogues and greatly reduced activity toward CMP-6-carboxylate, Bioorg. Chem. 1999, 27, 297-306.

Smilkstein, M.; Sriwilaijaroen, N.; Kelly, J. X.; Wilairat, P.; Riscoe, M. Simple and inexpensive fluorescence-based technique for high-throughput anti-malarial drug screening. Antimicrob. Agents Chemother. 2004, 48, 1803-1806.

Snider, M. J.; Wolfenden, R. The rate of spontaneous decarboxylation of amino acids. J. Am. Chem. Soc. 2000, 122, 11507-11508.

Sowa, T.; Ouchi, S. Facile synthesis of 5'-nucleotides by selective phosphorylation of a primary hydroxyl group of nucleosides with phosphoryl chloride. Bull. Chem. Soc. Jpn. 1975, 48, 2084-2090.

Sowa, T.; Ouchi, S. Facile synthesis of 5'-nucleotides by selective phosphorylation of a primary hydroxyl group of nucleosides with phosphoryl chloride. Bull. Chem. Soc. Jpn. 1975, 48, 2084-2090.

Tanaka, H.; Hayakawa, H.; Haraguchi, K.; Miyasaka, T. Introduction of an azido group to the C-6 position of uridine by the use of a 6-iodouridine derivative. Nucleosides & Nucleotides 1985, 4, 607-612.

Tittmann, K.; Golbik, R.; Uhlemann, K; Khailova, L.; Schneider, G.; Patel, M.; Jordan, F.; Chipman, D. M.; Duggleby, R. G.; Hübner, G. NMR analysis of covalent intermediates in thiamin diphosphate enzymes. Biochemistry 2003, 42, 7885-7891.

Todd, M. J. And Gomez, J. "Enzyme kinetics determined using calorimetry: a general assay for enzyme activity?", Anal. Biochem. (2001) 296, pp. 179-187.

Traut T.W. et al., "The Chemistry of the Reaction Determines the Invariant Amino Acids during the Evolution and Divergence of Orotidine 5'-Monophosphate Decarboxylase", The Journal of Biological Chemistry (2000) vol. 275, No. 37, pp. 28675-28681.

Ueda, T.; Yamamoto, M.; Yamane, A.; Imazawa, M.; Inoue, H. Conversion of uridine nucleotides to the 6-cyano derivatives: synthesis of orotidylic acid. Carbohyd. Nucleosides Nucleotides 1978, 5, 261-271.

Umezu, K.; Amaya, T.; Yoshimoto, A.; Tomita, K. J. Biochem. "Purification and Properties of Orotidine-5'-Phosphate Pyrophosphorylase and Orotidine-5'-Phosphate Decarboxylase from Bakers' Yeast". (Tokyo) 1971, 70, 249-262.

Vilar, S. et al. Probabilistic Neural Network Model for the in Silico Evaluation of Anti-HIV Activity and Mechanism of Action. J. Med. Chem. 49:1118-1124, 2006.

Warshel, A.; Strajbl, M.; Villa, J.; Florian, J. Remarkable rate enhancement of orotidine 5'-monophosphate decarboxylase is due to transition-state stabilization rather than to ground-state destabilization. Biochemistry 2000, 39, 14728-14738.

Warshel, A.; Florian, J. Computer simulations of enzyme catalysis: finding out what has been optimized by evolution. Proc. Natl. Acad. Sci. U.S.A. 1998, 95, 5950-5955.

Wiseman, T. Williston, S., Brandts, J. F. And Lin, L. N., "Rapid measurement of binding constants and heats of binding using a new titration calorimeter", Anal. Biochem. (1989) 179, pp. 131-137.

Wolf-Watz, M., Thai, V., Henzler-Wildman, K, Hadjipavlou, G., Eisenmesser, E. Z. And Kern, D., "Linkage between dynamics and catalysis in a thermophilic-mesophilic enzyme pair", Nat. Struct. Mol. Biol. (2004) 11, pp. 945-949.

Wu, N.; Mo, Y.; Gao, J.; Pai, E. F. Electrostatic stress in catalysis: structure and mechanism of the enzyme orotidine monophosphate decarboxylase. Proc. Natl. Acad. Sci. USA 2000, 97, 2017-2022.

Wu, N., Christendat, D., Dharamsi, A. And Pai, E. F., "Purification, crystallization and preliminary X-ray study of orotidine 5'-monophosphate decarboxylase", Acta Cryst. (2000) D56, pp. 912-914.

Wu, N.; Pai, E. F., "Crystal Structures of Inhibitor Complexes Reveal an Alternate Binding Mode in Orotidine-5'- monophosphate Decarboxylase", Biochemistry 2002, 277, 28080-28087.

Wu, N.; Gillon, W.; Pai, E. F. J. Biol. Chem. 2002, 41, 4002.

Ahmed, A. F. et al. "Synthesis of 6-Substituted Uridine Dervicatives". Journal of Pure and Applied Sciences 21(2):1-12, 2002.

Ahmed, A.F.S. "Synthesis of Some Uridine and Cytidine Derivatives". J. Chem. Research (S) 675, 1978.

Amyes, T. L.; Richard, J. P.; Tait, J. J. Activation of orotidine 5'-monophosphate decarboxylase by phosphate dianion: the whole substrate is the sum of two parts. J. Am. Chem. Soc. 2005, 127, 15708-15709.

Appleby, T. C.; Kinsland, C.; Begley, T. P.; Ealick, S. E. The crystal structure and mechanism of orotidine 5'-monophosphate decarboxylase. Proc. Natl. Acad. Sci. USA 2000, 97, 2005-2010.

Basnak, I. et al. The Synthesis of Some 5-Substituted and 5,6-Disubstituted 2'-Deoxyuridines. Nucleosides & Nucleotides, 13(1): 177-196, 1994.

Bianconi, M. L., "Calorimetric determination of thermodynamic parameters of reaction reveals different enthalpic compensations of the yeast hexokinase isozymes", J. Biol. Chem. (2003) 278, pp. 18709-18713.

Brakhage A. A. et al., "Menacing Mold: The Molecular Biology of *Aspergillus fumigatus*", Annu. Rev. Microbiol. (2002) 56:433-55.

Brown, G. K., Fox, R. M. and O'Sullivan, W. J., Interconversion of different molecular weight forms of human erythrocyte orotidylate decarboxylase, J. Biol. Chem. (1975) 250, pp. 7352-7358.

Brunger, A. T.; Adams, P. D.; Clore, G. M.; DeLano, W. L.; Gros, P.; Grosse-Kunstleve, R. W.; Jiang, J. S.; Kuszewski, J.; Nilges, M.; Pannu, N. S.; Read, R. J.; Rice, L. M.; Simonson, T.; Warren, G. L. Crystallography & NMR system: A new software suite for macromolecular structure determination. Acta Crystallogr D Biol Crystallogr 1998, 54 Part 5, 905-921.

Campling, B. G.; Pym, J.; Galbraith, P. R.; Cole, S. P. Use of MTT assay for rapid determination of chemosensitivity of human leukemic blast cells. Leukemia Res. 1988, 12, 823-831.

CAS Registry Number®, 817818-06-2 REGISTRY, Entered STN: Nov. 16, 1984, CN 5-Fluoro-6-iodo-Uridine.

CAS Registry Number®, 817818-08-4 REGISTRY, Entered STN: Nov. 16, 1984, CN 5-chloro-6-iodo-Uridine.

Christopherson, Richard I. et al. "Inhibitors of de Novo Nucleotide Biosysnthesis as Drugs". Acc. Chem. Res. 35, 961-971, 2002.

Collaborative Computational Project, N. The CCP4 suite: programs for protein crystallography. Acta Crystallogr D Biol Crystallogr 1994, 50, 760-763.

De Clercq, E.D. et al. "Selective in Vitro and in Vivo Activities of 5-(2-Haloalkyl)Pyrimidine Nucleoside Analogs, Particularly 5-(2-Chloroethyl)-2'-Deoxyuridine, Against Herpes Simplex Virus". Antimicrobial Agents and Chemotherapy. 28(2):246-251, 1985.

Donovan, W. P.; Kushnerm, S. R. Purification and characterization of orotidine-5'-monophosphate decarboxylase from *Escherichia coli*K-12. J. Bacteriol. 1983, 156, 620-624.

El Bahnasawy, et al., "Synthesis of Some Antimicrobial Pyrimidine Nucleoside Derivatives". Asw. Sc. Tec. Bull. 20:46-60, 2001.

Fujihashi, M.; Bello, A. M.; Poduch, E.; Wei, L; Annedi, S. C.; Pai, E. F.; Kotra, L. P. "An unprecedented twist to ODCase catalytic activity", J. Am. Chem. Soc. (2005) 127, pp. 15048-15050.

Gabrielsen B. et al., "In vitro and in in vivo antiviral (RNA) evaluation of orotidine 5'orotidine 5'-monophosphate decarboxylase inhibitors and analogs including 6-azauridine-5'(ethyl methoxyalaninyl)phosphate (a 5'-monophosphate prodrug)". Antiviral Chemistry Chemotherapy (1994), 5(4), pp. 209-20, US Army Medical Res. Inst. Infections Diseases, Frederick MD USA (p. 211 compounds 4a and 4g).

Gero, A. M.; O'Sullivan, W. J. Purines and pyrimidines in malarial parasites, Blood Cells 1990, 16, 467-484.

Gero, A. M. et al., "New Malaria Chemotherapy developed by Utilization of a Unique Parasite Transport System", Current Pharmaceutical Design (2003) vol. 9, No. 11, pp. 867-877.

Gómez, Zaida M. et al., "Antimalarial Activity of a Combination of 5-Fluoroorotate and Uridine in Mice", Antimicrobial Agents and Chemotherapy (1990) vol. 34, No. 7, pp. 1371-1375.

Gonzalez-Diaz, Humberto et al., "QSAR for anti-RNA-virus activity, synthesis, and assay of anti-RSV carbonucleosides given a unified representation of spectral moments, quadric, and topologic indices", Bioorganic & Medical Chemistry Letters, 2005, vol. 15, pp. 1651-1657.

Hanna M. M. et al., "Synthesis and characterization of a new photocrosslinking CTP analog and its use in photoaffinity labeling *E.coli* and T7 RNA polymerases", Nucleic Acids Research (1993) vol. 21, No. 9, pp. 2073-2079.

Harris, P.; Navarro Poulsen, J. C.; Jensen, K. F.; Larsen, S. Structural basis for the catalytic mechanism of a proficient enzyme: orotidine 5'-monophosphate decarboxylase. Biochemistry 2000, 39, 4217-4224.

Harris, P.; Poulsen, J. C. N.; Jensen, K. F.; Larsen, S. Substrate binding induces domain movements in orotidine 5'-monophosphate decarboxylase. J. Mol. Biol. 2002, 318, 1019-1029.

Hawley's Condensed Chemical Dictionary, Twelfth Edition, Revised by Richard J. Lewis, Sr., 1993, pp. 355-842.

Hirota, K; Tomishi, T.; Maki, Y.; Sajiki, H. Nucleosides & Nucleotides 1998, 17, 161-173.

Inoue, H.; Ueda, T. Chem. Pharm. Bull. 1978, 26, 2657-2663.

Janta-Lipinki, M. And Langen, P. Synthesis of 6-Substituted Thymine Nucleosides. Symposium Series No. 9, Nucleic Acids Research, 41-44, 1981.

Jencks, W. P. Binding energy, specificity, and enzymic catalysis: the Circe effect. Adv. Enzymol. Related Areas Mol. Biol. 1975, 43, 219-410.

Jones, M. E. Pyrimidine nucleotide biosynthesis in animals: Genes, enzymes, and regulation of UMP biosynthesis, Annu. Rev. Biochem. 1980, 49, 253-279.

Jones, T. A.; Zou, J.Y.; Cowan, S. W. Improved Methods for Building Protein Models in Electron Density Maps and the Location of Errors in these Models. Acta Crystallogr A 1991, 47, 110-119.

Kapuler, A. M. et al. Utilization of Substrate Analogs by Megovirus Induced RNA Polymerase. Short Communications. 701-706, 1969.

Krungkrai, J.; Krungkrai, S. R.; Phakanont, K. Anti-malarial activity of orotate analogs that inhibit dihydroorotase and dihydroorotate dehydrogenase. Biochem. Pharmacol. 1992, 43, 1295-1301.

Krungkrai, Sudaratana R. et al., "A Novel Enzyme Complex of Orotate Phosphoribosyltransferase and Orotidine 5'-Monophosphate Decarboxylase in Human Malaria Parasite *Plasmodium falciparum*.: Physical Association, Kinetics, and Inhibition Characterization", Biochemistry (2005) vol. 44, No. 5, pp. 1643-1652.

Lee, T. S.; Chong, L. T.; Chodera, J. D.; Kollman, P. A. An alternative explanation for the catalytic proficiency of orotidine 5'-phosphate decarboxylase. J. Am. Chem. Soc. 2001, 123, 12837-12848.

Levine, H. L.; Brody, R. S.; Westheimer, F. H. Inhibition of orotidine-5'-phosphate decarboxylase by 1-(5'-phosphobeta-d-ribofuranosyl)barbituric acid, 6 azauridine 5'-phosphate, and uridine 5'-phosphate, Biochemistry 1980, 19, 4993-4999.

Lieberman, I.; Kornberg, A.; Simms, E. S. J. Biol. Chem. 1955, 215, 403-415.

Miller, Brian G. et al., "Effects of Substrate Binding Determinants in the Transition State for Orotidine 5'-Monophosphate Decarboxylase", Bioorganic Chemistry (1998) vol. 26, pp. 283-288.

Miller, B. G.; Hassell, A. M.; Wolfenden, R.; Milburn, M. V.; Short, S. A. Anatomy of a proficient enzyme: the structure of orotidine 5'-monophosphate decarboxylase in the presence and absence of a potential transition state analog. Proc. Natl. Acad. Sci. USA 2000, 97, 2011-2016.

Miller, B. G.; Snider, M. J.; Short, S. A.; Wolfenden, R. Contribution of enzyme-phosphoribosyl contacts to catalysis by orotidine 5'-phosphate decarboxylase. Biochemistry 2000, 39, 8113-8118.

Miller, B. G.; Butterfoss, G. L.; Short, S. A.; Wolfenden, R. Role of enzyme-ribofuranosyl contacts in the ground state and transition state for orotidine 5'-phosphate decarboxylase: a role for substrate destabilization? Biochemistry 2001, 40, 6227-6232.

Miller, B. G.; Wolfenden, R. Catalytic proficiency: The unusual case of OMP decarboxylase. Ann. Rev. Biochem. 2002, 71, 847-885.

Morin, P. E. And Freire, E., Direct calorimetric analysis of the enzymatic activity of yeast cytochrome c oxidase, Biochemistry (1991) 30, pp. 8494-8500.

Neyts, J. et al. "Effect of 5-Iodo-2'-Deoxyuridine on Vaccinia Virus (Orthopoxvirus) Infections in Mice". Antimicrobial Agents and Chemotherapy 46(9):2842-2847, 2002.

Nord, L. D.; Willis, R. C.; Smee, D. F.; Riley, T. A.; Revankar, G. R.; Robins, R. K. Inhibition of orotidylate decarboxylase by 4(5H)-oxo-1-beta-D-ribofuranosylpyrazolo[3,4-d] pyrimidine-3-thiocarboxamide (APR-TC) in B lymphoblasts. Activation by adenosine kinase, Biochem. Pharmacol. 1988, 37, 4697-4705.

O'Brien, P. J.; Herschlag, D. Chem. Biol. 1999, 6, R91-R105.

Poduch, E.; Bello, A.M.; Tang, S.; Fujihashi, M.; Pai, E.F.; Kotra, L.P. Design of Inhibitors of Orotidine Monophosphate Decarboxylase Using Bioisosteric Replacement and Determination of Inhibition Kinetics. J. Med. Chem. 2006, 49, 4937-4935.

Porter, David J. T. et al., "Yeast Orotidine-5'-Phosphate Decarboxylase: Steady-State and Pre-Steady-State Analysis of the Kinetic Mechanism of Substrate Decarboxylation", Biochemistry (2000) vol. 39, No. 38, pp. 11788-11800.

6-Aza-UMP

R = -OH, 6-OH-UMP or BMP

XMP (12)

6-Thiocarboxamido UMP (13)

Pyrazofurin (14)

6-I-Uridine
(Compound Ii)

Pairwise Comparisons

| | Status | 1.00 | | 3.00 | | 4.00 | | 5.00 | |
|---|---|---|---|---|---|---|---|---|---|
| | | Chi-Square | Sig. | Chi-Square | Sig. | Chi-Square | Sig. | Chi-Square | Sig. |
| Log Rank (Mantel-Cox) | 1.00 | | | .020 | .886 | 5.000 | .025 | 5.000 | .025 |
| | 3.00 | .020 | .886 | | | .297 | .586 | 2.469 | .116 |
| | 4.00 | 5.000 | .025 | .297 | .586 | | | 2.469 | .116 |
| | 5.00 | 5.000 | .025 | 2.469 | .116 | 2.469 | .116 | | |

US 8,067,391 B2

ODCASE INHIBITORS FOR THE TREATMENT OF MALARIA

This application is a National Stage of International Application No. PCT/CA2006/001620, filed Oct. 3, 2005, which claims the benefit of Provisional Application Nos. 60/596,537, filed Oct. 3, 2005 and 60/597,142 filed Nov. 12, 2005, the contents of which are herein incorporated by reference.

FIELD OF THE INVENTION

The present invention relates to methods of using certain 6-substituted uridine compounds for the treatment and prevention of malaria. The invention also relates to novel uridine compounds having ODCase inhibitory activity and to pharmaceutical compositions comprising these compounds.

BACKGROUND OF THE INVENTION

ODCase (EC 4.1.1.23) plays a central role in the de novo synthesis of uridine-5'-O-monophosphate (UMP). UMP is a building block, synthesized de novo from aspartic acid, for the synthesis of other pyrimidine nucleotides such as uridine-5'-O-triphosphate (UTP), cytidine-5'-O-triphosphate (CTP), thymidine-5'-O-triphosphate (TMP) and 2'-deoxy-cytidine-5'-O-triphosphate (dCTP) (FIG. 1). Pyrimidine nucleotides are the building blocks for the synthesis of RNA and DNA, the essential molecules for cell replication and survival. Due to its important role in the cell's de novo nucleic acid synthesis, ODCase is present in bacteria, archea, parasites and in humans, i.e. almost every species except in viruses. This enzyme catalyzes the decarboxylation of orotidine monophosphate (OMP) to uridine monophosphate (UMP) (compounds 1 and 2 in the final step in FIG. 1). This enzyme is particularly interesting for enzymologists because it exhibits an extraordinary level of catalytic rate enhancement of over 17 orders of magnitude compared to the uncatalyzed decarboxylation reaction in water at neutral pH 7.0, 25° C.[i,ii] An uncatalyzed decarboxylation occurs of OMP takes about 78 million years, and the enzymic decarboxylation at a millisecond time scale. Thus, ODCase is one of the most proficient members of the enzymic world.[ii,iii,iv,v]

Interestingly, decarboxylases found in Nature use either a cofactor or covalent intermediates during the catalysis of decarboxylation reactions.[vi,vii] For example, thiamin diphosphate-dependent, indole pyruvate decarboxylase (IPDC) uses thiamin as a cofactor and there are covalent intermediates formed with the cofactor during the decarboxylation process. ODCase is thought to be quite unusual in catalyzing decarboxylation with such proficiency without the help of any co-factors, metals, or covalent-intermediates.[i,ii,iii] One interesting difference when one looks at this enzyme across species is that in certain higher level organisms such as human or mouse, ODCase is a part of the bifunctional enzyme, UMP synthase.[viii] In pathogenic organisms such as bacteria, fungi and parasites, ODCase is a monofunctional enzyme.[ix,x] In all species, ODCase (whether monofunctional or bifunctional) is active as a dimeric unit.

In general, investigations targeting ODCase focused on malaria, cancer and few antiviral investigations. In the past two decades, several analogs of OMP were investigated extensively to understand the catalytic mechanism of ODCase.[iii,xi] Among these analogs, 6-aza-UMP (3) and 6-hydroxy-UMP (or BMP, 4), pyrazofurin, xanthosine-5'-monophosphate (XMP, 12) and 6-thiocarboxamido-UMP (13) are some of the potent inhibitors that were studied against ODCase (FIG. 2).[xii,xiii,xiv] However, the development of inhibitor candidates has been limited due to their toxicities and lack of specificity.[xii] There is also very limited or non-existent structure-activity relationship investigations and inhibitor design against ODCase. Thus, ODCase has not gained much traction in 1980s and 1990s as a drug target.

Aside from its obvious pharmacological interest, ODCase has been a favorite enzyme for biochemists and structural biologists due to its unusual catalytic properties. A number of mechanisms were proposed prior to and after the availability of X-ray crystal structures for several ODCases in 2000.[xv,xvi,xvii,xviii] Although ideas of covalent catalysis were discussed, none of the mechanisms presented included a covalent species formation as a key step during the decarboxylation by ODCase. An analysis of the catalytic site of ODCase from *Methanobacterium thermoautotrophicum* (Mt) revealed two aspartate residues (Asp70 and Asp75B, the latter contributed by the second subunit of the dimeric ODCase) and two lysine residues (Lys42 and Lys72) that are held via a strong network of hydrogen bonds (FIG. 3). Analyses of several co-crystal structures of ODCase with a variety of ligands confirm that these residues are held tightly in their respective positions in the active site and there is less than 0.5 Å movement in the positions of the side chains of these residues. Existing evidence does not support any active site residue forming a covalent bond either to the substrate during catalysis or to any known inhibitor.[iii,xvi,xix,xx,xxi] The above four residues are proposed to exert strong steric and electrostatic stress onto the C-6 carboxylate group of OMP and eliminate the carboxyl group.[xvi]

The x-ray crystal structures of ODCase from ten different species are known today. In 2000, four x-ray crystal structures of ODCase brought insights into the catalytic mechanism of this enzyme. Based on the structure of *S. cerevisiae* ODCase complexed with the transition-state analogue BMP (4), a transition-state stabilization mechanism of OMP decarboxylation was proposed.[xviii] A similar proposal was also suggested by Appleby et al. based on the crystal structure of ODCase (*Bacillus subtilis*) complexed with the product, UMP.[xvii] These authors suggested that the decarboxylation reaction proceeds via an electrophilic substitution in which C-6 is protonated by Lys62 as the carbon dioxide molecule is released.[xvii] The structure of the ODCase enzyme from *E. coli* co-crystallized with BMP was the basis of the proposal submitted by Harris et al.[xxii] Based on the proximity of the carboxylate moiety on OMP (1) and Asp71 residue in the active site of ODCase, it was proposed that OMP decarboxylation depends on the existence of a shared proton between Asp71 and the carboxyl group of the substrate.[xxii] A similar mechanism involving electrostatic repulsion was put forward by Wu et al.[xvi] This mechanism of OMP decarboxylation is based on the principles of the Circe effect described by Jencks in 1975.[xxiii] The Circe effect states that only the reactive group of the substrate needs to be destabilized. The strong interaction between the unreactive part of the substrate and the enzyme active site provides the energy to directly destabilize the reactive group of the substrate.[xxiii] The electrostatic repulsion mechanism points to the active site aspartate residue. In four different species the location and function of this residue is highly conserved. The catalytic residues, Asp70 and Lys72 are located near the reaction center C-6 of the pyrimidine ring of the substrate OMP and Asp70 (*M. thermoautotrophicum*) was postulated to provide the electrostatic destabilization of the enzyme-substrate complex. Lys72 in the active site furnishes the proton to neutralize the carbanion developed after the departure of the carboxylate.[xvi] Despite several x-ray structures and in-depth enzymology in the past two decades, ODCase continues to challenge biochemists with still-unresolved mechanism and new twists (vide infra).

In the active site of ODCase, the monophosphate group of OMP is proposed to bind first and this group contributes the largest energy required for the binding of the substrate to ODCase.[xxiv] The removal of phosphate from the molecule of substrate resulted in a significantly lower catalytic efficiency measured as the second-order rate constant ($k_{cat}/K_M$) for the catalysis of substrate to product.[xxiv] In an interesting experiment, the binding of phosphite dianion ($HPO_3^{2-}$) to ODCase (from S. cerevisiae) resulted in an 80,000 fold increase in the second order rate constant for the decarboxylation of the truncated substrate lacking a phosphate moiety.[xxv] Thus, the phosphate group is an important component for ODCase binding. Thus, in order for nucleoside drugs (correct terminology is prodrugs) to be active against ODCase in vivo, the nucleoside compound has to be converted into its monophosphate form inside the cell by any nucleoside kinase and then inhibit ODCase (whether in a pathogen or human cell). This is very similar to other nucleoside drugs such as AZT, 3TC, gemcitabine among several nucleoside drugs that are clinically used, thus there is a good possibility for the "nucleoside forms" of ODCase inhibitors to function as drugs.

If one carefully analyzes the biochemical and pharmacological basis, ODCase is one of most fascinating enzymes as a drug target. For example, Plasmodia species such as P. falciparum and P. vivax are dependent on their own de novo synthesis of pyrimidine nucleotides due to the absence of the salvage pathway in these parasites.[xxvi] In human, however, pyrimidine nucleotides are synthesized via both the de novo and salvage pathways.[xxvii] Thus, inhibition of plasmodial ODCase has been proposed as a strategy to design compounds directed against malaria and limited number of orotate analogs were investigated as potential drugs against the malarial parasite.[xii,xxviii,xxix] Most of these compounds are very polar with poor pharmacokinetics problems.

There remains a need for new inhibitors of ODCase as therapeutic agents, for example, for the prevention and treatment of malaria.

SUMMARY OF THE INVENTION

Several C6 derivatives of uridine were prepared and found to be noncovalent (competitive) and covalent (irreversible) inhibitors against ODCase. These compounds also exhibited potent anti-plasmodial activity.

Accordingly, the present invention includes a method of treating or preventing malaria comprising administering to a subject in need thereof an anti-malarial effective amount of a compound selected from a compound of Formula I, tautomers thereof and pharmaceutically acceptable salts, solvates, and prodrugs thereof:

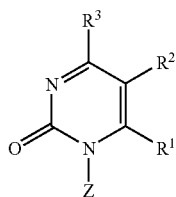

(I)

wherein,
$R^1$ is selected from CN, $N_3$, I, Br, $NH_2$, $NO_2$, $C(O)C_{1-6}$alkyl, $NHC_1$-$C_6$alkyl, $N(C_1$-$C_6$alkyl$)_2$, $NHC(O)C_1$-$C_6$alkyl and $NHC(O)OC_1$-$C_6$alkyl;

$R^2$ is selected from H, halo, $C_1$-$C_6$alkyl, $C_1$-$C_6$alkoxy, fluoro-substituted-$C_1$-$C_6$alkyl, fluoro-substituted-$C_1$-$C_6$alkoxy, $N_3$, $NH_2$ and CN;

$R^3$ is selected from OH, $NH_2$, H and $NHC(O)C_1$-$C_6$alkyl;

Z is selected from:

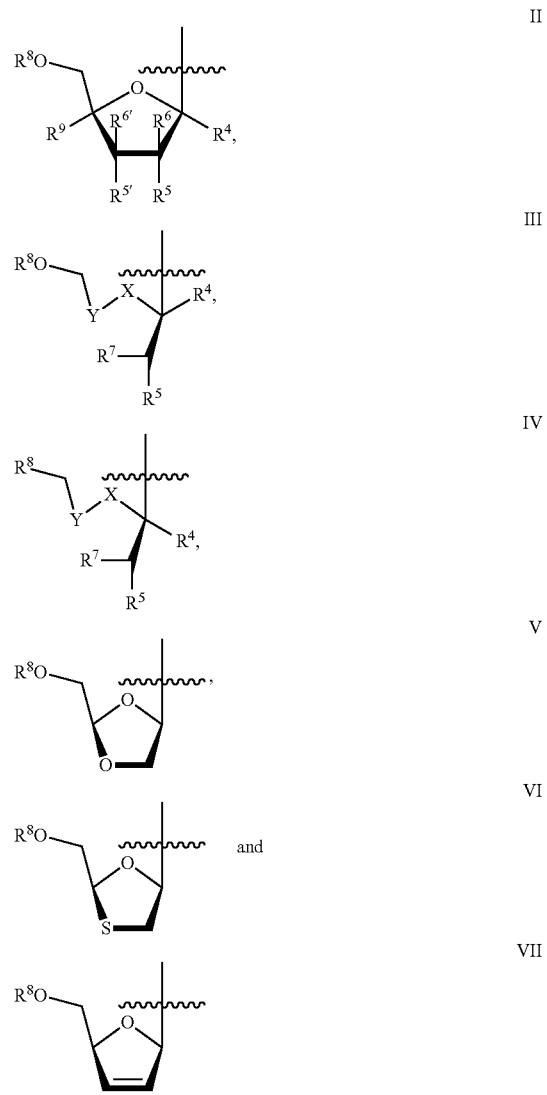

wherein,
$R^4$ is selected from H, $C_1$-$C_6$alkyl and hydroxy-substituted-$C_1$-$C_6$alkyl;

One of $R^5$ and $R^6$ is hydrogen and the other is selected from H, OH and F and one of $R^{5'}$ and $R^{6'}$ is hydrogen and the other is selected from H, OH and F; or $R^5$ and $R^6$ or $R^{5'}$ and $R^{6'}$ together may be =O or =$CH_2$;

$R^7$ is selected from H, F and OH;

$R^8$ is selected from H, $C(O)C_1$-$C_6$alkyl, $P(O)(OH)_2$, $P(O)(OC_1$-$C_6$alkyl$)_2$ and $P(O)(OC_1$-$C_6$alkyl)OH;

$R^9$ is selected from H, $N_3$, CN, $C_1$-$C_6$alkyl; and

X—Y is selected from —$CH_2$—O—, —O—$CH_2$— and —S—$CH_2$—.

In further embodiments, the present invention includes a use of a compound selected from a compound of Formula I as defined above, and pharmaceutically acceptable salts, solvates, and prodrugs thereof, for the prevention or treatment of malaria as well as a use of a compound selected from a compound of Formula I as defined above, and pharmaceutically acceptable salts, solvates, and prodrugs thereof, for the preparation of a medicament for the prevention or treatment of malaria.

The present invention further includes a method of preventing or treating an infection of a malarial parasite in a subject in need thereof comprising administering to the subject a compound selected from a compound of Formula I as defined above, and pharmaceutically acceptable salts, solvates, and prodrugs thereof. Also included in the present invention is a method of inhibiting ODCase in a plasma or blood sample isolated from a subject comprising adding to said plasma or blood sample an inhibiting effective amount of a compound selected from a compound of Formula I as defined above, and pharmaceutically acceptable salts, solvates, and prodrugs thereof, The present invention also includes a use of a compound selected from a compound of Formula I as defined above, and pharmaceutically acceptable salts, solvates, and prodrugs thereof, to prevent or treat an infection of a malarial parasite in a subject as well as a use of a compound selected from a compound of Formula I as defined above, and pharmaceutically acceptable salts, solvates, and prodrugs thereof, to prepare a medicament to prevent or treat an infection of a malarial parasite in a subject. Still further, the present invention further includes a use of a compound selected from a compound of Formula I as defined above, and pharmaceutically acceptable salts, solvates, and prodrugs thereof, for inhibiting ODCase in a plasma or blood sample isolated from a subject as well as a use of a compound selected from a compound of Formula I as defined above, and pharmaceutically acceptable salts, solvates, and prodrugs thereof, to prepare a medicament for inhibiting ODCase in a plasma or blood sample isolated from a subject.

According to another aspect of the present invention, there is included a pharmaceutical composition for the treatment or prevention of malaria comprising an antimalarial effective amount of a compound selected from a compound of Formula I as defined above, and pharmaceutically acceptable salts, solvates, and prodrugs thereof, and a pharmaceutically acceptable carrier or diluent.

The present inventors have shown that certain novel 6-substituted uridine derivatives are useful as inhibitors of ODCase, in particular for the treatment and prevention of malaria. Accordingly, the present invention further includes a compound selected from:
6-(dimethylamino) uridine;
5-fluoro-6-amino uridine;
5-bromo-6-amino uridine;
5-fluoro-6-azido uridine;
1'-Hydroxymethyl-6-iodo-uridine;
6-(dimethylamino) 2'-deoxyuridine;
5-fluoro-6-amino 2'-deoxyuridine;
5-bromo-6-amino 2'-deoxyuridine;
5-fluoro-6-azido 2'-deoxyuridine;
5-chloro-6-iodo 2'-deoxyuridine;
5-chloro-6-azido 2'-deoxyuridine;
5-methoxy-6-iodo 2'-deoxyuridine;
5-methoxy-6-azido 2'-deoxyuridine;
5-methoxy-6-amino 2'-deoxyuridine;
5-bromo-6-iodo 2'-deoxyuridine;
5-bromo-6-azido 2'-deoxyuridine;
6-(dimethylamino) uridine 5'-monophosphate;
5-fluoro-6-amino uridine 5'-monophosphate;
5-bromo-6-amino uridine 5'-monophosphate;
5-fluoro-6-azido uridine 5'-monophosphate;
1'-hydroxymethyl-6-iodo-uridine-5'-monophosphate
  6-(dimethylamino) 2'-deoxyuridine 5'-monophosphate;
5-fluoro-6-amino 2'-deoxyuridine 5'-monophosphate;
5-bromo-6-amino 2'-deoxyuridine 5'-monophosphate;
5-fluoro-6-azido 2'-deoxyuridine 5'-monophosphate;
5-chloro-6-iodo 2'-deoxyuridine 5'-monophosphate;
5-chloro-6-azido 2'-deoxyuridine 5'-monophosphate;
5-methoxy-6-iodo 2'-deoxyuridine 5'-monophosphate;
5-methoxy-6-azido 2'-deoxyuridine 5'-monophosphate;
5-methoxy-6-amino 2'-deoxyuridine 5'-monophosphate;
5-bromo-6-iodo 2'-deoxyuridine 5'-monophosphate;
5-bromo-6-azido 2'-deoxyuridine 5'-monophosphate;
5-fluoro-6-iodo uridine 5'-monophosphate;
6-iodo uridine 5'-acetate;
6-iodo 2'-deoxyuridine 5'-acetate, and
pharmaceutically acceptable salts, solvates, and prodrugs thereof.

The present invention further includes a pharmaceutical composition comprising a compound selected from:
6-(dimethylamino) uridine;
5-fluoro-6-amino uridine;
5-bromo-6-amino uridine;
5-fluoro-6-azido uridine;
1'-Hydroxymethyl-6-iodo-uridine;
6-(dimethylamino) 2'-deoxyuridine;
5-fluoro-6-amino 2'-deoxyuridine;
5-bromo-6-amino 2'-deoxyuridine;
5-fluoro-6-azido 2'-deoxyuridine;
5-chloro-6-iodo 2'-deoxyuridine;
5-chloro-6-azido 2'-deoxyuridine;
5-methoxy-6-iodo 2'-deoxyuridine;
5-methoxy-6-azido 2'-deoxyuridine;
5-methoxy-6-amino 2'-deoxyuridine;
5-bromo-6-iodo 2'-deoxyuridine;
5-bromo-6-azido 2'-deoxyuridine;
6-(dimethylamino) uridine 5'-monophosphate;
5-fluoro-6-amino uridine 5'-monophosphate;
5-bromo-6-amino uridine 5'-monophosphate;
5-fluoro-6-azido uridine 5'-monophosphate;
1'-hydroxymethyl-6-iodo-uridine-5'-monophosphate
  6-(dimethylamino) 2'-deoxyuridine 5'-monophosphate;
5-fluoro-6-amino 2'-deoxyuridine 5'-monophosphate;
5-bromo-6-amino 2'-deoxyuridine 5'-monophosphate;
5-fluoro-6-azido 2'-deoxyuridine 5'-monophosphate;
5-chloro-6-iodo 2'-deoxyuridine 5'-monophosphate;
5-chloro-6-azido 2'-deoxyuridine 5'-monophosphate;
5-methoxy-6-iodo 2'-deoxyuridine 5'-monophosphate;
5-methoxy-6-azido 2'-deoxyuridine 5'-monophosphate;
5-methoxy-6-amino 2'-deoxyuridine 5'-monophosphate;
5-bromo-6-iodo 2'-deoxyuridine 5'-monophosphate;
5-bromo-6-azido 2'-deoxyuridine 5'-monophosphate;
5-fluoro-6-iodo uridine 5'-monophosphate;
6-iodo uridine 5'-acetate;
6-iodo 2'-deoxyuridine 5'-acetate, and
pharmaceutically acceptable salts, solvates, and prodrugs thereof, along with a pharmaceutically acceptable carrier.

Other features and advantages of the present invention will become apparent from the following detailed description. It should be understood, however, that the detailed description and the specific examples while indicating preferred embodiments of the invention are given by way of illustration only, since various changes and modifications within the spirit and scope of the invention will become apparent to those skilled in the art from this detailed description.

DETAILED DESCRIPTION OF THE INVENTION

I. Definitions

Figure 1:
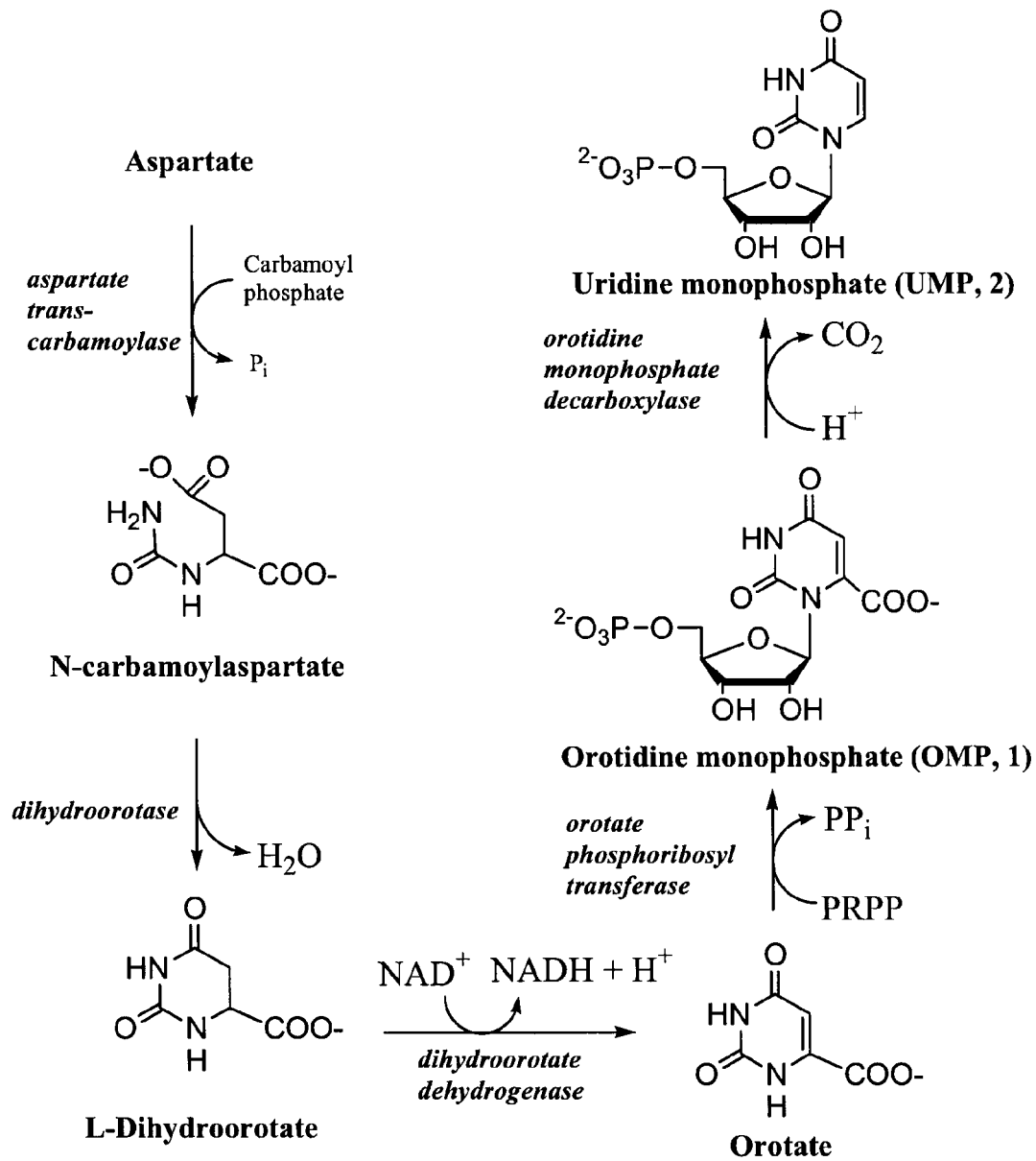
FIG. 1 is a schematic showing the de novo synthesis of uridine monophosphate from aspartic acid (prior art).
Figure 2:
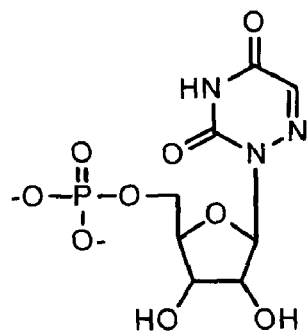
FIG. 2 is a schematic showing the chemical structures of analogs of orotidine monophosphate (OMP) that are known as inhibitors of ODCase.
Figure 2:
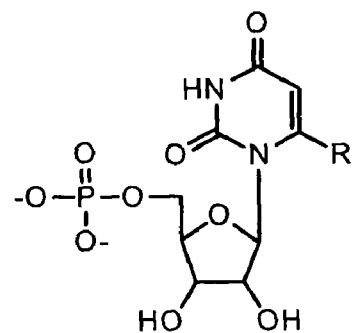
Figure 2:
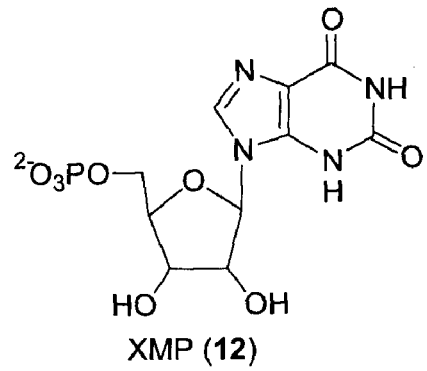
Figure 2:
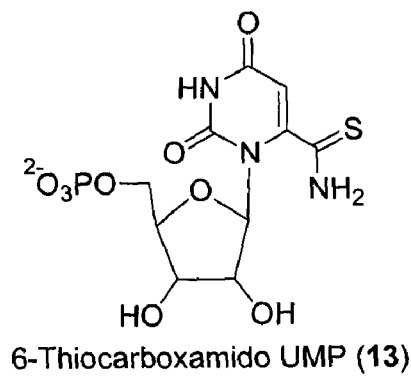
Figure 2:
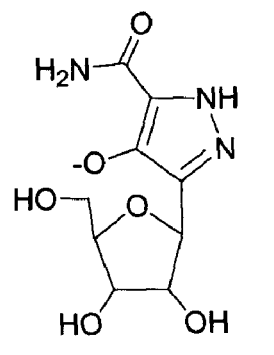
Figure 3:
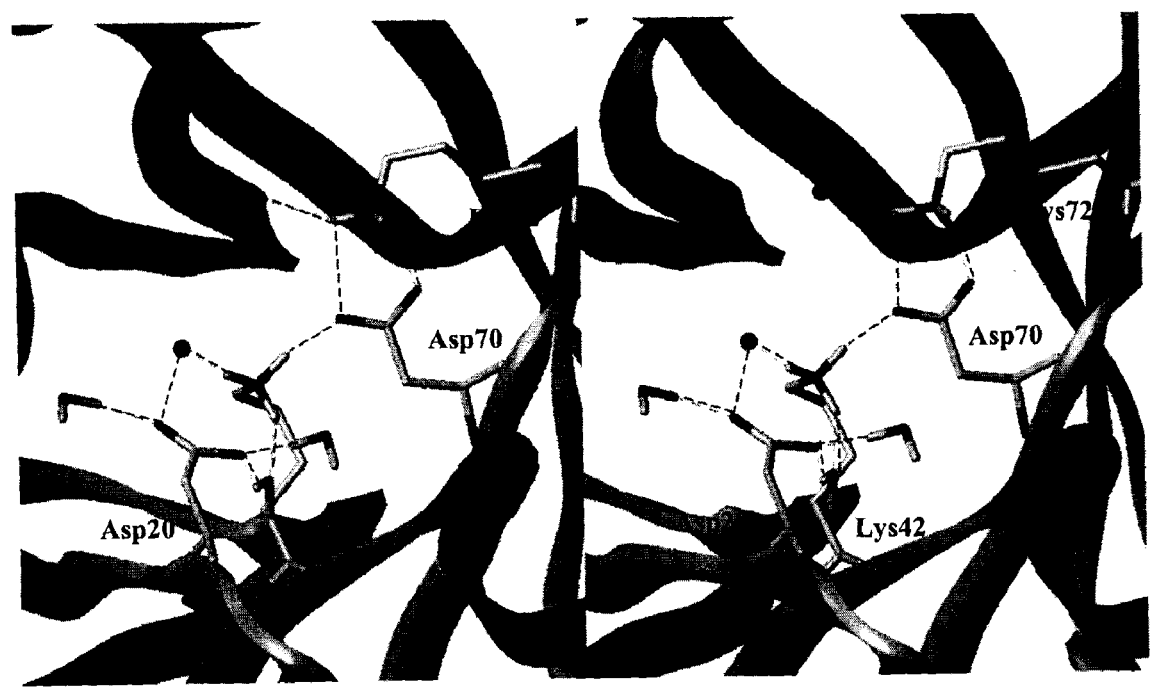
FIG. 3 shows the X-ray structure of the catalytic site of ODCase from *Methanobacterium thermoautotrophicum*.

The term "$C_{1-n}$alkyl" as used herein means straight and/or branched chain, saturated alkyl radicals containing from one to "n" carbon atoms and includes (depending on the identity of n) methyl, ethyl, propyl, isopropyl, n-butyl, s-butyl, isobutyl, t-butyl, 2,2-dimethylbutyl, n-pentyl, 2-methylpentyl, 3-methylpentyl, 4-methylpentyl, n-hexyl and the like, where the variable n is an integer representing the largest number of carbon atoms in the alkyl radical.

The term "fluoro-substituted $C_{1-n}$alkyl" as used herein means straight and/or branched chain, saturated alkyl radicals containing from one to n carbon atoms in which one or all of the hydrogen atoms have been replaced with a fluorine, and includes (depending on the identity of "n") trifluoromethyl, pentafluoroethyl, fluoromethyl and the like, where the variable n is an integer representing the largest number of carbon atoms in the alkyl radical.

The term "hydroxy-substituted $C_{1-n}$alkyl" as used herein means straight and/or branched chain, saturated alkyl radicals containing from one to n carbon atoms in which one or two of the hydrogen atoms have been replaced with a hydroxyl group, and includes (depending on the identity of "n") $CH_2OH$, $CHOHCH_2CH_3$, $CH_2CHOHCH_2CH_2OH$ and the like, where the variable n is an integer representing the largest number of carbon atoms in the alkyl radical.

The term "halo" as used herein means halogen and includes chloro, fluoro, bromo and iodo.

The term "tautomer" as used herein refers to compounds that are interconvertible by a formal migration of a hydrogen atom or proton, accompanied by a switch of a single bond and an adjacent double bond. In solutions where tautomerization is possible, a chemical equilibrium of the tautomers will be reached. The exact ratio of the tautomers depends on several factors, including temperature, solvent and pH.

The term "solvate" as used herein means a compound of Formula I, or a salt of a compound of Formula I, wherein molecules of a suitable solvent are incorporated in the crystal lattice. A suitable solvent is physiologically tolerable at the dosage administered. Examples of suitable solvents are ethanol, water and the like. When water is the solvent, the molecule is referred to as a "hydrate".

The term "compound(s) of the invention" as used herein means compound(s) of Formula I, and salts, solvates and prodrugs thereof.

The term "pharmaceutically acceptable salt" means an acid addition salt or a basic addition salt which is suitable for or compatible with the treatment of patients.

The term "pharmaceutically acceptable acid addition salt" as used herein means any non-toxic organic or inorganic salt of any base compound of the invention, or any of its intermediates. Basic compounds of the invention that may form an acid addition salt include, for example, where the $R^1$, $R^2$ and/or $R^3$ is $NH_2$ and $NHC_{1-6}$alkyl. Illustrative inorganic acids which form suitable salts include hydrochloric, hydrobromic, sulfuric and phosphoric acids, as well as metal salts such as sodium monohydrogen orthophosphate and potassium hydrogen sulfate. Illustrative organic acids that form suitable salts include mono-, di-, and tricarboxylic acids such as glycolic, lactic, pyruvic, malonic, succinic, glutaric, fumaric, malic, tartaric, citric, ascorbic, maleic, benzoic, phenylacetic, cinnamic and salicylic acids, as well as sulfonic acids such as p-toluene sulfonic and methanesulfonic acids. Either the mono or di-acid salts can be formed, and such salts may exist in either a hydrated, solvated or substantially anhydrous form. In general, the acid addition salts of the compounds of the invention are more soluble in water and various hydrophilic organic solvents, and generally demonstrate higher melting points in comparison to their free base forms. The selection of the appropriate salt will be known to one skilled in the art. Other non-pharmaceutically acceptable acid addition salts, e.g. oxalates, may be used, for example, in the isolation of the compounds of the invention, for laboratory use, or for subsequent conversion to a pharmaceutically acceptable acid addition salt.

The term "pharmaceutically acceptable basic addition salt" as used herein means any non-toxic organic or inorganic base addition salt of any acid compound of the invention, or any of its intermediates. Acidic compounds of the invention that may form a basic addition salt include, for example, where $R^8$ is a phosphate. Illustrative inorganic bases which form suitable salts include lithium, sodium, potassium, calcium, magnesium or barium hydroxide. Illustrative organic bases which form suitable salts include aliphatic, alicyclic or aromatic organic amines such as methylamine, trimethylamine and picoline, alkylammonias or ammonia. The selection of the appropriate salt will be known to a person skilled in the art. Other non-pharmaceutically acceptable basic addition salts, may be used, for example, in the isolation of the compounds of the invention, for laboratory use, or for subsequent conversion to a pharmaceutically acceptable acid addition salt.

The term "malaria" as used herein refers to an infectious disease, also known as ague or marsh fever, typically caused by a protistan parasite of the genus *Plasmodium*, suitably, *P. falciparum, P. virax, P. ovale* or *P. malariae*. This parasite is transmitted primarily by female *Anopheles* mosquitoes. *Plasmodium* invades and consumes the red blood cells of its hosts, which leads to symptoms including fever, anemia, and in severe cases, a coma potentially leading to death.

The term a "therapeutically effective amount", "effective amount" or a "sufficient amount" of a compound of the present invention is a quantity sufficient to, when administered to the subject, including a mammal, for example a human, effect beneficial or desired results, including clinical results, and, as such, an "effective amount" or synonym thereto depends upon the context in which it is being applied. For example, in the context of inhibiting ODCase, for example, it is an amount of the compound sufficient to achieve such an inhibition in ODCase activity as compared to the response obtained without administration of the compound. In the context of disease, therapeutically effective amounts of the compounds of the present invention are used to treat, modulate, attenuate, reverse, or effect malaria in a mammal. An "effective amount" is intended to mean that amount of a compound that is sufficient to treat, prevent or inhibit malaria or a disease associated with malaria. In some suitable embodiments, malaria or the disease or disorder associated with malaria is caused by a *Plasmodium* parasite, suitably, *P. falciparum, P. virax, P. ovale* or *P. malariae*, thus it is the amount sufficient to, when administered to the subject, including a mammal, e.g., a human, to treat, prevent or inhibit malaria or a disease or a disorder associated with malaria or a malarial parasite, e.g. *Plasmodium* parasite. The amount of a given compound of the present invention that will correspond to such an amount will vary depending upon various factors, such as the given drug or compound, the pharmaceutical formulation, the route of administration, the type of disease or disorder, the identity of the subject or host being treated, and the like, but can nevertheless be routinely determined by one skilled in the art. Also, as used herein, a "therapeutically effective amount" of a compound of the present invention is an amount which prevents, inhibits, suppresses or reduces malaria (e.g., as determined by clinical symptoms or the amount of malarial parasites, e.g., *Plasmodium* organisms) in a subject as compared to a control. As defined herein, a therapeutically effective amount of a compound of the present invention may be readily determined by one of ordinary skill by routine methods known in the art.

In an embodiment, a therapeutically effective amount of a compound of the present invention ranges from about 0.1 to about 7 mg/kg body weight, suitably about 1 to about 5 mg/kg body weight, and more suitably, from about 2 to about 3 mg/kg body weight. The skilled artisan will appreciate that certain factors may influence the dosage required to effectively treat a subject, or prevent a subject, from being afflicted with malaria and these factors include, but are not limited to, the severity of the disease or disorder, previous treatments, the general health and/or age of the subject and other diseases present.

Moreover, a "treatment" or "prevention" regime of a subject with a therapeutically effective amount of the compound of the present invention may consist of a single administration, or alternatively comprise a series of applications. For example, the compound of the present invention may be administered at least once a week. However, in another embodiment, the compound may be administered to the patient from about one time per week to about once daily for a given treatment. The length of the treatment period depends on a variety of factors, such as the severity of the disease, the age of the patient, the concentration and the activity of the compounds of the present invention, or a combination thereof. It will also be appreciated that the effective dosage of the compound used for the treatment or prophylaxis may increase or decrease over the course of a particular treatment or prophylaxis regime. Changes in dosage may result and become apparent by standard diagnostic assays known in the art. In some instances, chronic administration may be required. The compounds of the present invention may be administered before, during or after exposure to malaria or malarial parasite, e.g. *Plasmodium* parasite.

As used herein, "administered contemporaneously" means that two substances are administered to a subject such that they are both biologically active in the subject at the same time. The exact details of the administration will depend on the pharmacokinetics of the two substances in the presence of each other, and can include administering one substance within 24 hours of administration of the other, if the pharmacokinetics are suitable. Design of suitable dosing regimens are routine for one skilled in the art. In particular embodiments, two substances will be administered substantially simultaneously, i.e. within minutes of each other, or in a single composition that comprises both substances.

As used herein, and as well understood in the art, "treatment" is an approach for obtaining beneficial or desired results, including clinical results. Beneficial or desired clinical results can include, but are not limited to, alleviation or amelioration of one or more symptoms or conditions, diminishment of extent of disease, stabilized (i.e. not worsening) state of disease, preventing spread of disease, delay or slowing of disease progression, amelioration or palliation of the disease state, and remission (whether partial or total), whether detectable or undetectable. "Treatment" can also mean prolonging survival as compared to expected survival if not receiving treatment.

"Palliating" a disease or disorder means that the extent and/or undesirable clinical manifestations of a disorder or a disease state are lessened and/or time course of the progression is slowed or lengthened, as compared to not treating the disorder.

The term "prevention" or "prophylaxis", or synonym thereto, as used herein refers to a reduction in the risk or probability of a patient becoming afflicted with malaria or manifesting a symptom associated with malaria.

To "inhibit" or "suppress" or "reduce" a function or activity, such as ODCase activity, is to reduce the function or activity when compared to otherwise same conditions except for a condition or parameter of interest, or alternatively, as compared to another conditions.

The term "subject" as used herein includes all members of the animal kingdom including human. The subject is suitably a human.

II. Methods of the Invention

The present invention includes a method of treating or preventing malaria comprising administering to a subject in need thereof an anti-malarial effective amount compound selected from a compound of Formula I, tautomers thereof and pharmaceutically acceptable salts, solvates, and prodrugs thereof:

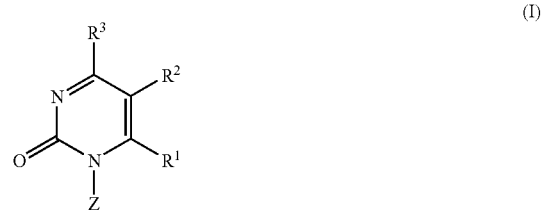

(I)

wherein, $R^1$ is selected from CN, $N_3$, I, Br, $NH_2$, $NO_2$, $C(O)C_{1-6}$alkyl, $NHC_1$-$C_6$alkyl, $N(C_1$-$C_6$alkyl$)_2$, $NHC(O)C_1$-$C_6$alkyl and $NHC(O)OC_1$-$C_6$alkyl;

$R^2$ is selected from H, halo, $C_1$-$C_6$alkyl, $C_1$-$C_6$alkoxy, fluoro-substituted-$C_1$-$C_6$alkyl, fluoro-substituted-$C_1$-$C_6$alkoxy, $N_3$, $NH_2$ and CN;

$R^3$ is selected from OH, $NH_2$, H and $NHC(O)C_1$-$C_6$alkyl;
Z is selected from:

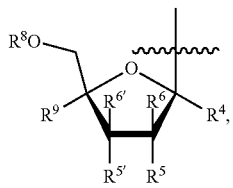  II

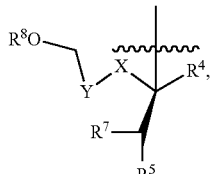  III

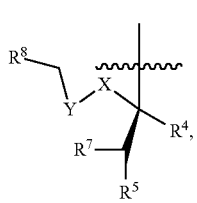  IV

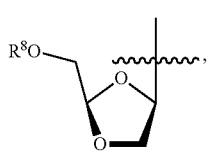  V

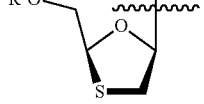  VI  and

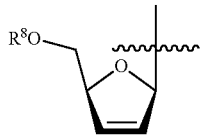  VII wherein,
$R^4$ is selected from H, $C_1$-$C_6$alkyl and hydroxy-substituted-$C_1$-$C_6$alkyl;
One of $R^5$ and $R^6$ is hydrogen and the other is selected from H, OH and F and one of $R^{5'}$ and $R^{6'}$ is hydrogen and the other is selected from H, OH and F; or
$R^5$ and $R^6$ or $R^{5'}$ and $R^{6'}$ together may be =O or =$CH_2$;
$R^7$ is selected from H, F and OH;
$R^8$ is selected from H, $C(O)C_1$-$C_6$alkyl, $P(O)(OH)_2$, $P(O)(OC_1$-$C_6$alkyl$)_2$ and $P(O)(OC_1$-$C_6$alkyl)OH;
$R^9$ is selected from H, $N_3$, CN, $C_1$-$C_6$alkyl; and
X—Y is selected from —$CH_2$—O—, —O—$CH_2$— and —S—$CH_2$—.

In the method of the invention, $R^1$ in the compounds of Formula I is selected from CN, $N_3$, I, Br, $NH_2$, $NO_2$, $NHC_1$-$C_6$alkyl, $N(C_1$-$C_6$alkyl$)_2$, $NHC(O)C_1$-$C_6$alkyl and $NHC(O)OC_1$-$C_6$alkyl. In embodiments of the invention, $R^1$ in the compounds of Formula I is selected from I, Br, $NO_2$, $N(C_1$-$C_4$alkyl$)_2$, $NHC(O)C_1$-$C_4$alkyl and $NHC(O)OC_1$-$C_4$alkyl. In further embodiments of the invention, $R^1$ in the compounds of Formula I is selected from I, Br, $NO_2$, $N(CH_3)_2$, $NHC(O)CH_3$ and $NHC(O)CH_3$. In still further embodiments of the invention, $R^1$ in the compounds of Formula I is selected from I, Br and $N(CH_3)_2$. $R^1$ in the compounds of Formula I is I (iodine).

In the method of the invention, $R^2$ in the compounds of Formula I is selected H, halo, $C_1$-$C_6$alkyl, $C_1$-$C_6$alkoxy, fluoro-substituted-$C_1$-$C_6$alkyl, fluoro-substituted-$C_1$-$C_6$alkoxy, $N_3$, $NH_2$ and CN. In embodiments of the invention, $R^2$ in the compounds of Formula I is selected H, halo, $C_1$-$C_4$alkyl, $C_1$-$C_4$alkoxy, fluoro-substituted-$C_1$-$C_4$alkyl, fluoro-substituted-$C_1$-$C_4$alkoxy, $N_3$, $NH_2$ and CN. In further embodiments of the invention, $R^2$ in the compounds of Formula I is selected H, fluoro, chloro, bromo, $CH_3$, $OCH_3$, $CF_3$, $CF_3O$, $N_3$, $NH_2$ and CN. In still further embodiments of the invention, $R^2$ in the compounds of Formula I is selected H, fluoro, chloro, bromo, $OCH_3$ and $CF_3$, $CF_3O$.

In the method of the invention, $R^3$ in the compounds of Formula I is selected from OH, $NH_2$, H and $NHC(O)C_1$-$C_6$alkyl. In embodiments of the invention, $R^3$ in the compounds of Formula I is selected OH and $NH_2$. When $R^3$ in the compounds of Formula I is selected OH and $NH_2$, the compounds of formula I may exist as one of the following tautomers:

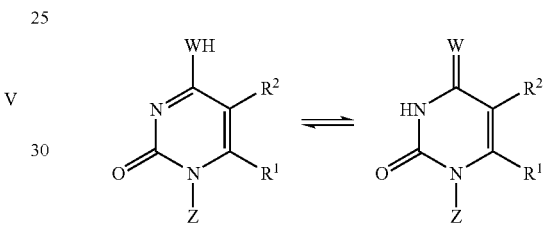

where W is O or NH. In embodiments of the invention W is O and the favoured tautomer is:

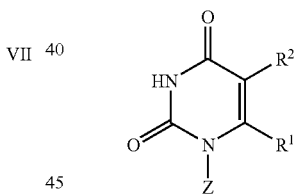

In the method of the invention, Z in the compounds of Formula I is selected from:

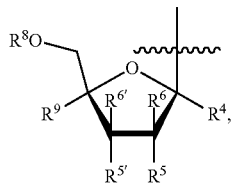  II

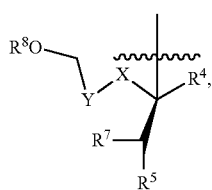  III

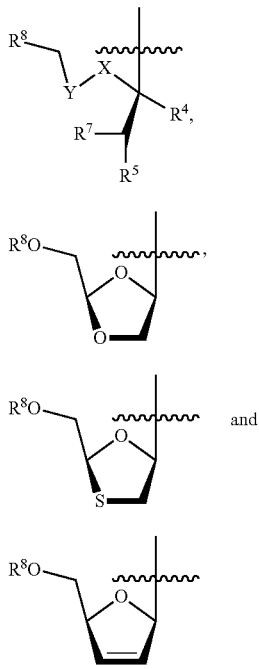

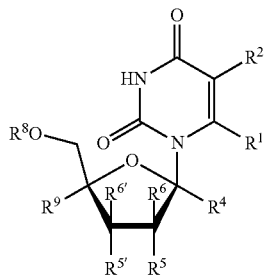

In an embodiment of the invention, Z is of the Formula II.

In the method of the invention, $R^4$ in the compounds of Formula I is selected from H, $C_1$-$C_6$alkyl and hydroxy-substituted-$C_1$-$C_6$alkyl. In an embodiment of the invention $R^4$ in the compounds of Formula I is H.

In the method of the invention, the compounds of Formula I include those in which $R^5$ and $R^{5'}$ are independently selected from H, OH and F and $R^6$ and $R^{6'}$ are independently selected from H, OH and F, provided that when $R^5$ is not H then $R^6$ is H and when $R^{5'}$ is not H then $R^{6'}$ is H; or $R^5$ and $R^6$ or $R^{5'}$ and $R^{6'}$ together may be =O or =CH$_2$. In an embodiment of the invention, $R^5$ and $R^{5'}$ are both OH and $R^6$ and $R^{6'}$ are both H. In a further embodiment of the invention, $R^5$ is H, $R^{5'}$ is OH and $R^6$ and $R^{6'}$ are both H.

In the method of the invention, $R^7$ in the compounds of Formula I is selected from H, F and OH, suitably H or OH.

In the method of the invention, $R^8$ in the compounds of Formula I is selected from H, C(O)$C_1$-$C_6$alkyl, P(O)(OH)$_2$, P(O)(O$C_1$-$C_6$alkyl)$_2$ and P(O)(O$C_1$-$C_6$alkyl)OH. In embodiments of the invention, $R^8$ in the compounds of Formula I is selected from H, C(O)$C_1$-$C_4$alkyl, P(O)(OH)$_2$, P(O)(O$C_1$-$C_4$alkyl)$_2$ and P(O)(O$C_1$-$C_4$alkyl)OH. In further embodiments of the invention, $R^8$ in the compounds of Formula I is selected from H, C(O)CH$_3$, P(O)(OH)$_2$, P(O)(OCH$_3$)$_2$ and P(O)(OCH$_3$)OH. In still further embodiments of the invention, $R^8$ in the compounds of Formula I is selected from H, C(O)CH$_3$, and P(O)(OH)$_2$.

In the method of the invention, $R^9$ in the compounds of Formula I is selected from H, $N_3$, CN, $C_1$-$C_6$alkyl. Suitably $R^9$ is H.

In the method of the invention, X—Y in the compounds of Formula I is selected from —CH$_2$—O—, —O—CH$_2$— and —S—CH$_2$—. Suitably X—Y is —O—CH$_2$—.

It is an embodiment of the invention that $R^3$ is OH and Z is Formula II. In these compounds the keto tautomeric form is preferred. Accordingly, it is an embodiment of the invention that the compound of Formula I in the method of the invention has the following structure.

In an embodiment of the invention, the compound of Formula I in the method of the invention is selected from:
6-Cyanouridine;
6-Cyanouridine-5'-monophosphate;
6-Azido uridine;
6-Azido uridine-5'-O-monophosphate;
6-Amino uridine-5'-O-monophosphate;
6-Amino uridine;
6-Methyl uridine;
6-Methyl uridine-5'-O-monophosphate;
6-Iodo-uridine;
6-N-Methylamino uridine;
6-N,N-Dimethylamino uracil;
6-N,N-Dimethylamino uridine;
6-N-Methylamino uridine-5'-O-monophosphate;
6-Iodo uridine-5'-O-monophosphate;
5-Fluoro-6-amino uridine;
5-Bromo-6-iodo uridine;
5-Fluoro-6-azido uridine;
5-Fluoro-6-iodo uridine;
5-Fluoro-6-amino uridine-5'-O-monophosphate;
5-Bromo-6-iodo uridine-5'-O-monophosphate;
5-Fluoro-6-azido uridine-5'-O-monophosphate;
5-Fluoro-6-iodo uridine-5'-O-monophosphate;
6-Methoxycarbonyl uridine;
6-Ethoxycarbonyl uridine;
6-Methoxycarbonyl uridine-5'-O-monophosphate;
6-Ethoxycarbonyl uridine-5'-O-monophosphate;
1'-Hydroxymethyl-6-iodo-uridine;
1'-Hydroxymethyl-6-iodo-uridine-5'-monophosphate, and
and
pharmaceutically acceptable salts, solvates, and prodrugs thereof.

All of the compounds of Formula I have more than one asymmetric centre. Where the compounds according to the invention possess more than one asymmetric centre, they may exist as diastereomers. It is to be understood that all such isomers and mixtures thereof in any proportion are encompassed within the scope of the present invention. In suitable embodiments of the invention, the stereochemistry is that found in the natural form of uridine as depicted above. It is to be understood that while, the relative stereochemistry of the compounds of Formula I is suitably as shown above, such compounds of Formula I may also contain certain amounts (e.g. less than 20%, preferably less than 10%, more preferably less than 5%) of compounds of Formula I having alternate stereochemistry.

In further embodiments, the present invention includes a use of a compound selected from a compound of Formula I as defined above, and pharmaceutically acceptable salts, solvates, and prodrugs thereof, for the prevention or treatment of malaria as well as a use of a compound selected from a compound of Formula I as defined above, and pharmaceutically acceptable salts, solvates, and prodrugs thereof, for the preparation of a medicament for the prevention or treatment of malaria.

The present invention further includes a method of preventing or treating an infection of a malarial parasite in a subject in need thereof comprising administering to the subject a compound selected from a compound of Formula I as defined above, and pharmaceutically acceptable salts, solvates, and prodrugs thereof. Also included in the present invention is a method of inhibiting ODCase in a plasma or blood sample isolated from a subject comprising adding to said plasma or blood sample an inhibiting effective amount of a compound selected from a compound of Formula I as defined above, and pharmaceutically acceptable salts, solvates, and prodrugs thereof, The present invention also includes a use of a compound selected from a compound of Formula I as defined above, and pharmaceutically acceptable salts, solvates, and prodrugs thereof, to prevent or treat an infection of a malarial parasite in a subject as well as a use of a compound selected from a compound of Formula I as defined above, and pharmaceutically acceptable salts, solvates, and prodrugs thereof, to prepare a medicament to prevent or treat an infection of a malarial parasite in a subject. Still further, the present invention further includes a use of a compound selected from a compound of Formula I as defined above, and pharmaceutically acceptable salts, solvates, and prodrugs thereof, for inhibiting ODCase in a plasma or blood sample isolated from a subject as well as a use of a compound selected from a compound of Formula I as defined above, and pharmaceutically acceptable salts, solvates, and prodrugs thereof, to prepare a medicament for inhibiting ODCase in a plasma or blood sample isolated from a subject.

According to another aspect of the present invention, there is included a pharmaceutical composition for the treatment or prevention of malaria comprising an anti-malarial effective amount of a compound selected from a compound of Formula I as defined above, and pharmaceutically acceptable salts, solvates, and prodrugs thereof, and a pharmaceutically acceptable carrier or diluent.

The compounds of the invention are suitably formulated into pharmaceutical compositions for administration to human subjects in a biologically compatible form suitable for administration in vivo.

The compositions containing the compounds of the invention can be prepared by known methods for the preparation of pharmaceutically acceptable compositions which can be administered to subjects, such that an effective quantity of the active substance is combined in a mixture with a pharmaceutically acceptable vehicle. Suitable vehicles are described, for example, in Remington's Pharmaceutical Sciences (2003-20th edition) and in The United States Pharmacopeia: The National Formulary (USP 24 NF19) published in 1999. On this basis, the compositions include, albeit not exclusively, solutions of the substances in association with one or more pharmaceutically acceptable vehicles or diluents, and contained in buffered solutions with a suitable pH and iso-osmotic with the physiological fluids.

The compounds of Formula I may be used pharmaceutically in the form of the free base, in the form of salts, solvates and as hydrates. All forms are within the scope of the invention. Acid and basic addition salts may be formed with the compounds of the invention for use as sources of the free base form even if the particular salt per se is desired only as an intermediate product as, for example, when the salt is formed only for the purposes of purification and identification. All salts that can be formed with the compounds of the invention are therefore within the scope of the present invention.

In accordance with the methods of the invention, the described compounds of the invention, may be administered to a patient in a variety of forms depending on the selected route of administration, as will be understood by those skilled in the art. The compounds of the invention may be administered, for example, by oral, parenteral, buccal, sublingual, nasal, rectal, patch, pump or transdermal administration and the pharmaceutical compositions formulated accordingly. Parenteral administration includes intravenous, intraperitoneal, subcutaneous, intramuscular, transepithelial, nasal, intrapulmonary, intrathecal, rectal and topical modes of administration. Parenteral administration may be by continuous infusion over a selected period of time.

A compound of the invention may be orally administered, for example, with an inert diluent or with an assimilable edible carrier, or it may be enclosed in hard or soft shell gelatin capsules, or it may be compressed into tablets, or it may be incorporated directly with the food of the diet. For oral therapeutic administration, the compound of the invention may be incorporated with excipient and used in the form of ingestible tablets, buccal tablets, troches, capsules, elixirs, suspensions, syrups, wafers, and the like.

A compound of the invention may also be administered parenterally. Solutions of a compound of the invention can be prepared in water suitably mixed with a surfactant such as hydroxypropylcellulose. Dispersions can also be prepared in glycerol, liquid polyethylene glycols, DMSO and mixtures thereof with or without alcohol, and in oils. Under ordinary conditions of storage and use, these preparations contain a preservative to prevent the growth of microorganisms. A person skilled in the art would know how to prepare suitable formulations. Conventional procedures and ingredients for the selection and preparation of suitable formulations are described, for example, in Remington's Pharmaceutical Sciences (2003-20th edition) and in The United States Pharmacopeia: The National Formulary (USP 24 NF19) published in 1999.

The pharmaceutical forms suitable for injectable use include sterile aqueous solutions or dispersion and sterile powders for the extemporaneous preparation of sterile injectable solutions or dispersions. In all cases the form must be sterile and must be fluid to the extent that easy syringability exists.

Compositions for nasal administration may conveniently be formulated as aerosols, drops, gels and powders. Aerosol formulations typically comprise a solution or fine suspension of the active substance in a physiologically acceptable aqueous or non-aqueous solvent and are usually presented in single or multidose quantities in sterile form in a sealed container, which can take the form of a cartridge or refill for use with an atomizing device. Alternatively, the sealed container may be a unitary dispensing device such as a single dose nasal inhaler or an aerosol dispenser fitted with a metering valve which is intended for disposal after use. Where the dosage form comprises an aerosol dispenser, it will contain a propellant which can be a compressed gas such as compressed air or an organic propellant such as fluorochlorohydrocarbon. The aerosol dosage forms can also take the form of a pump-atomizer.

Compositions suitable for buccal or sublingual administration include tablets, lozenges, and pastilles, wherein the active ingredient is formulated with a carrier such as sugar, acacia, tragacanth, or gelatin and glycerine. Compositions for rectal administration are conveniently in the form of suppositories containing a conventional suppository base such as cocoa butter.

The compounds of the invention, may be administered to an animal alone or in combination with pharmaceutically acceptable carriers, as noted above, the proportion of which is determined by the solubility and chemical nature of the compound, chosen route of administration and standard pharmaceutical practice.

The dosage of the compounds of the invention can vary depending on many factors such as the pharmacodynamic properties of the compound, the mode of administration, the age, health and weight of the recipient, the nature and extent of the symptoms, the frequency of the treatment and the type of concurrent treatment, if any, and the clearance rate of the compound in the animal to be treated. One of skill in the art can determine the appropriate dosage based on the above factors. The compounds of the invention may be administered initially in a suitable dosage that may be adjusted as required, depending on the clinical response. For ex vivo treatment of cells over a short period, for example for 30 minutes to 1 hour or longer, higher doses of compound may be used than for long term in vivo therapy. In an embodiment of the invention, dosage forms (compositions suitable for administration) contain from about 1 mg to about 500 mg of active ingredient (one or more compounds of the invention) per unit. In these pharmaceutical compositions, the active ingredient will ordinarily be present in an amount of about 0.5 to 95% weight based on the total weight of the composition.

The compounds of the invention, can be used alone or contemporaneously with other agents that inhibit ODCase activity or in combination with other types of treatment (which may or may not modulate ODCase) for malaria.

III. Novel Compounds of the Invention

Novel compounds showing inhibition of the enzyme ODCase and anti-malarial activity have been prepared. Accordingly, the present invention includes all uses of these novel compounds including their use in therapeutic methods and compositions for treating or preventing malaria, their use in diagnostic assays and their use as research tools and as starting materials and/or intermediates in the preparation of other chemical entities.

Accordingly, the present invention provides a compound of Formula I selected from:
6-(dimethylamino) uridine;
5-fluoro-6-amino uridine;
5-bromo-6-amino uridine;
5-fluoro-6-azido uridine;
1'-Hydroxymethyl-6-iodo-uridine;
6-(dimethylamino) 2'-deoxyuridine;
5-fluoro-6-amino 2'-deoxyuridine;
5-bromo-6-amino 2'-deoxyuridine;
5-fluoro-6-azido 2'-deoxyuridine;
5-chloro-6-iodo 2'-deoxyuridine;
5-chloro-6-azido 2'-deoxyuridine;
5-methoxy-6-iodo 2'-deoxyuridine;
5-methoxy-6-azido 2'-deoxyuridine;
5-methoxy-6-amino 2'-deoxyuridine;
5-bromo-6-iodo 2'-deoxyuridine;
5-bromo-6-azido 2'-deoxyuridine;
6-(dimethylamino) uridine 5'-monophosphate;
5-fluoro-6-amino uridine 5'-monophosphate;
5-bromo-6-amino uridine 5'-monophosphate;
5-fluoro-6-azido uridine 5'-monophosphate;
1'-Hydroxymethyl-6-iodo-uridine-5'-monophosphate
6-(dimethylamino) 2'-deoxyuridine 5'-monophosphate;
5-fluoro-6-amino 2'-deoxyuridine 5'-monophosphate;
5-bromo-6-amino 2'-deoxyuridine 5'-monophosphate;
5-fluoro-6-azido 2'-deoxyuridine 5'-monophosphate;
5-chloro-6-iodo 2'-deoxyuridine 5'-monophosphate;
5-chloro-6-azido 2'-deoxyuridine 5'-monophosphate;
5-methoxy-6-iodo 2'-deoxyuridine 5'-monophosphate;
5-methoxy-6-azido 2'-deoxyuridine 5'-monophosphate;
5-methoxy-6-amino 2'-deoxyuridine 5'-monophosphate;
5-bromo-6-iodo 2'-deoxyuridine 5'-monophosphate;
5-bromo-6-azido 2'-deoxyuridine 5'-monophosphate;
5-fluoro-6-iodo uridine 5'-monophosphate;
6-iodo uridine 5'-acetate;
6-iodo 2'-deoxyuridine 5'-acetate, and
pharmaceutically acceptable salts, solvates, and prodrugs thereof.

The present invention further includes a pharmaceutical composition comprising a pharmaceutically effective amount of one or more of the above-listed compounds and a pharmaceutically acceptable carrier. The present invention also includes the use of one or more of the above-listed compounds, or pharmaceutically acceptable salts, solvates, and prodrugs thereof, as medicaments.

VI. Methods of Preparing Compounds of the Invention

In accordance with another aspect of the present invention, the compounds of the invention can be prepared by processes analogous to those established in the art. In particular, reactions for functionalizing the 5 and/or 6 position of a uracil, cytosine or thymine ring are well known. For example, treatment of uracil, cytosine or thymine with a strong base, such as an alkyl lithium or lithium diisopropyl amine, at reduced temperatures, such at about −60° C. to about −90° C., followed by reaction with a reagent of the Formula $R^1$-LG, wherein $R^1$ is as defined in Formula I and LG is a suitable leaving group, such as halo, provides a compound substituted at the 6-position of the pyrimidine ring with $R^1$. Compounds substituted with a suitable leaving group at the 5-position of the pyrimidine ring of uracil or cytosine are commercially available or are known in the art. These compounds may be converted to their corresponding anions at reduced temperatures, such at about −60° C. to about −90° C., and reacted with a reagent of the Formula $R^2$-LG, wherein $R^2$ is as defined in Formula I and LG is a suitable leaving group, such as halo to provide a compound substituted at the 5-position of the pyrimidine ring with $R^2$. Conversion of various $R^1$ and $R^2$ groups into other $R^1$ and $R^2$ groups can be done using standard chemistries known to those skilled in the art. For example, azido groups may be reduced to provide amine groups which may be monoalkylated, dialkylated or acylated using known chemistries.

Pyrimidine compounds may be reacted with a reagent of the formula Z-LG, wherein Z is as defined in Formula I and LG is a suitable leaving group under standard conditions to provide nucleosides of Formula I or precursors to Formula I. Such reactions would be well known to those skilled in the art. Substitution of the appropriate $R^1$, $R^2$ and/or $R^3$ groups on the pyrimidine ring may be done before or after the coupling with Z.

Pyrimidine compounds and reagents of the Formula Z-LG are commercially available or may be prepared using methods known in the art. Acylation or addition of the phosphate group on to the 5' position of the nucleoside may be performed using known reactions.

In some cases the chemistries outlined above may have to be modified, for instance by use of protective groups, to prevent side reactions due to reactive groups, such as reactive groups attached as substituents. This may be achieved by means of conventional protecting groups, for example as described in "Protective Groups in Organic Chemistry" McOmie, J. F. W. Ed., Plenum Press, 1973 and in Greene, T. W. and Wuts, P. G. M., "Protective Groups in Organic Synthesis", John Wiley & Sons, $3^{rd}$ Edition, 1999.

The formation of a desired compound salt is achieved using standard techniques. For example, the neutral compound is treated with an acid or base in a suitable solvent and the formed salt is isolated by filtration, extraction or any other suitable method.

The formation of solvates of the compounds of the invention will vary depending on the compound and the solvate. In general, solvates are formed by dissolving the compound in the appropriate solvent and isolating the solvate by cooling or using an antisolvent. The solvate is typically dried or azeotroped under ambient conditions.

Prodrugs of the compounds of Formula I may be, for example, conventional esters formed with available hydroxy, thiol, amino or carboxyl group. For example, available hydroxy or amino groups may be acylated using an activated acid in the presence of a base, and optionally, in inert solvent (e.g. an acid chloride in pyridine). Some common esters which have been utilized as prodrugs are phenyl esters, aliphatic ($C_8$-$C_{24}$) esters, acyloxymethyl esters, carbamates and amino acid esters.

The present invention includes radiolabeled forms of the compounds of the invention, for example, compounds of the invention labeled by incorporation within the structure $^3H$, $^{11}C$ or $^{14}C$ or a radioactive halogen such as $^{125}I$ and $^{18}F$. A radiolabeled compound of the invention may be prepared using standard methods known in the art. For example, tritium may be incorporated into a compound of the invention using standard techniques, for example by hydrogenation of a suitable precursor to a compound of the invention using tritium gas and a catalyst. Alternatively, a compound of the invention containing radioactive iodo may be prepared from the corresponding trialkyltin (suitably trimethyltin) derivative using standard iodination conditions, such as [$^{125}I$] sodium iodide in the presence of chloramine-T in a suitable solvent, such as dimethylformamide. The trialkyltin compound may be prepared from the corresponding non-radioactive halo, suitably iodo, compound using standard palladium-catalyzed stannylation conditions, for example hexamethylditin in the presence of tetrakis(triphenylphosphine) palladium (0) in an inert solvent, such as dioxane, and at elevated temperatures, suitably 50-100° C. Further, a compound of the invention containing a radioactive fluorine may be prepared, for example, by reaction of K[$^{18}F$]/K222 with a suitable precursor compound, such as a compound of Formula I comprising a suitable leaving group, for example a tosyl group, that may be displaced with the $^{18}F$ anion.

The following non-limiting examples are illustrative of the present invention:

VI. Examples

Example 1

Synthesis of Compounds Ia and Ib

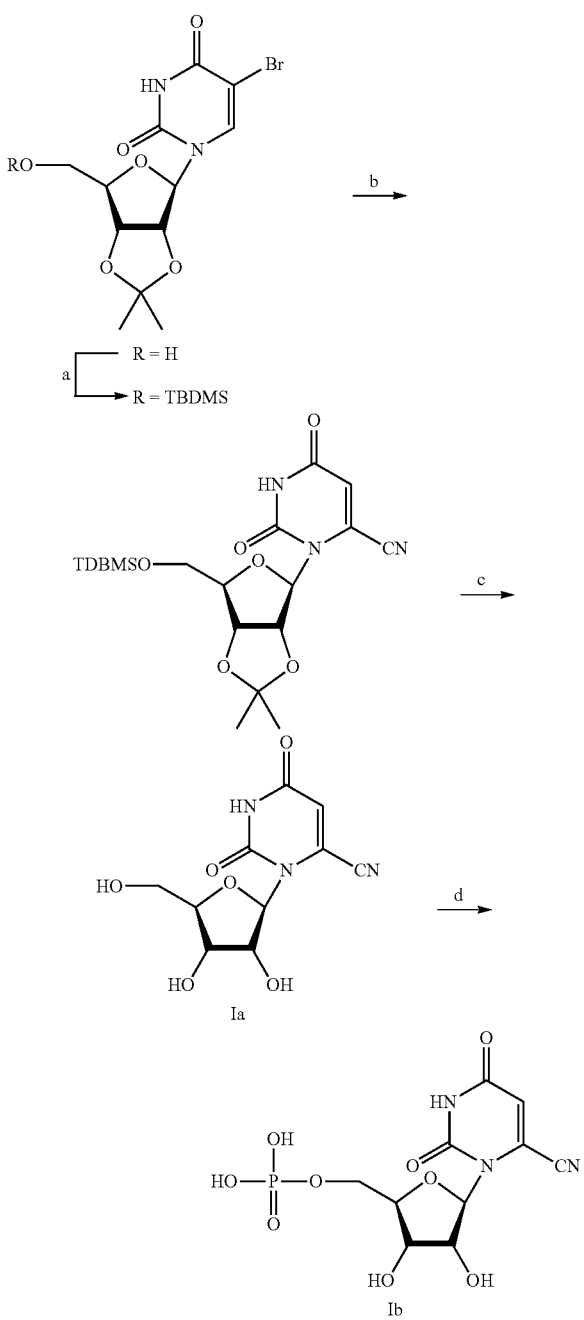

a) TBDMSiCl, imidazole; $CH_2Cl_2$; b) NaCN DMF; c) 50% aq. TFA; d) $POCl_3$, Py, $H_2O$, $CH_3CN$, 0° C.

Target molecules Ia and Ib were synthesized starting from the 5-bromo-uridine derivative as shown in the above scheme. 2',3'-O-isopropylidene-5-bromouridine was prepared according to a literature procedure[xxx]. Protection of the primary alcohol in 2',3'-O-isopropylidene-5-bromouridine as a silyl ether was carried out with TBDMSiCl under basic conditions. Fully protected compound was then converted to the 6-cyano derivative using sodium cyanide.[xxxi] The deprotection of the protecting groups with 50% aqueous solution of trifluoroacetic acid to yield compound Ia, followed by the mono-phosphorylation with phosphorus oxychloride afforded the desired target molecule Ib.[xxxii,xxxiii,xxxiv] Finally compound Ib was converted into its ammonium salt using aqueous $(NH_4)_2CO_3$ solution.

(a) 5'-O-(t-Butyldimethylsilyl)-2',3'-O-isopropylidene-5-bromouridine: A solution of 2',3'-O-isopropylidene-5-bromouridine (0.25 g, 0.69 mmol) in dry $CH_2Cl_2$ (5.0 mL) was treated with imidazole (0.093 g, 1.38 mmol) and TBDMSiCl (0.103 g, 0.69 mmol) at 0° C. The reaction mixture was then brought to room temperature, and stirred for 1 h. The reaction mixture was diluted with $CH_2Cl_2$ and the organic layer was washed with water, brine and dried over $Na_2SO_4$. Organic layer was concentrated under reduced pressure and the crude compound was purified by silica gel column chromatography (EtOAc:Hexane, 1:9) to obtain compound 5'-O-(t-Butyldimethylsilyl)-2',3'-O-isopropylidene-5-bromouridine (0.32 g, 98%) as a foam. $^1$H NMR (CDCl$_3$) δ 0.12 (s, 6H), 0.91 (s, 9H), 1.36 (s, 3H), 1.59 (s, 3H), 3.79 (dd, 1H, J=2.7, 11.5 Hz), 3.93 (dd, 1H, J=2.1, 11.5 Hz), 4.39 (brd, 1H, J=2.1 Hz), 4.67 (dd, 1H, J=3.0, 6.0 Hz), 4.72 (dd, 1H, J=2.1, 6.0 Hz), 5.89 (d, 1H, J=3.0 Hz), 7.90 (s, 1H), 8.41 (brs, 1H).

(b) 5'-O-(t-Butyldimethylsilyl)-2',3'-O-isopropylidene-6-cyanouridine. A solution of 5'-O-(t-butyldimethylsilyl)-2',3'-O-isopropylidene-5-bromouridine (0.32 g, 0.71 mmol) in dry DMF (3 mL) was treated with NaCN (0.052 g, 1.07 mmol) at room temperature and the resulting mixture was stirred for 24 h. The reaction mixture was diluted with water (20 mL) and the pH of the solution was brought to ~6 and was extracted with ethyl acetate (3×20 mL). The combined ethyl acetate layers were washed with brine, dried ($Na_2SO_4$) and concentrated under reduced pressure. The crude compound was purified by silica gel column chromatography (EtOAc:Hexane, 1:3) to obtain 5'-O-(t-butyldimethylsilyl)-2',3'-O-isopropylidene-6-cyanouridine in quantitative yield (0.28 g). $^1$H NMR (CDCl$_3$) δ ppm 0.06 (s, 6H), 0.89 (s, 9H), 1.35 (s, 3H), 1.57 (s, 3H), 3.81-3.85 (m, 2H), 4.13-4.18 (m, 1H), 4.76 (dd, 1H, J=4.8, 6.6 Hz), 5.12 (dd, 1H, J=2.4, 6.6 Hz), 6.03 (d, 1H, J=2.4 Hz), 6.29 (s, 1H), 8.88 (brs, 1H); $^{13}$C NMR (CDCl$_3$) δ ppm 4.79, 18.84, 25.74, 26.27, 27.52, 63.64, 81.45, 83.65, 88.62, 93.74, 110.84, 113.11, 115.06, 127.71, 148.57, 160.55.

(c) 6-Cyanouridine (Ia). Compound 5'-O-(t-Butyldimethylsilyl)-2',3'-O-isopropylidene-6-cyanouridine (0.12 g, 0.30 mmol) was treated with 50% aqueous TFA (5 mL) at 0° C., then brought to room temperature and stirred for 2 h. Solvent was evaporated and the crude compound was purified by silica gel column chromatography (EtOH: CHCl$_3$, 1:9) to obtain 6-cyanouridine (Ia) in quantitative yield (0.076 g). UV $λ_{max}$=283 nm; $^1$H NMR (DMSO-d$_6$/D$_2$O) δ ppm 3.41-3.66 (m, 3H), 4.00 (t, 1H, J=5.7, 6.0 Hz), 4.45 (dd, 1H, J=5.1, 6.0 Hz), 5.73 (d, 1H, J=5.1 Hz), 6.66 (s, 1H).

(d) 6-Cyanouridine-5'-monophosphate (Ib). A stirred solution of POCl$_3$ (0.3 mL, 3.271 mmol), H$_2$O (0.037 g, 2.081 mmol) and CH$_3$CN (2 mL) was treated with pyridine (0.28 mL, 2.081 mmol) at 0° C. and to this, 6-cyanouridine (0.2 g, 0.743 mmol) was added. After 5 h of stirring at 0° C., the reaction mixture was quenched with 50 mL of cold water and the stirring was continued for another 1 h. The reaction mixture was concentrated and the crude compound was purified on Dowex ion-exchange resin (1.0 M formic acid) to obtain 6-Cyanouridine-5'-monophosphate (10) (0.12 g, 46%). UV (H$_2$O): $λ_{max}$=283 nm; $^1$H NMR (D$_2$O) δ 3.98-4.26 (m, 3H), 4.43 (t, 1H, J=6.3 Hz), 4.77 (dd, 1H, J=3.9, 6.3 Hz), 5.95 (d, 1H, J=3.9 Hz), 6.64 (s, 1H).

Example 2

Synthesis of Compounds Ic, Id, Ie and If

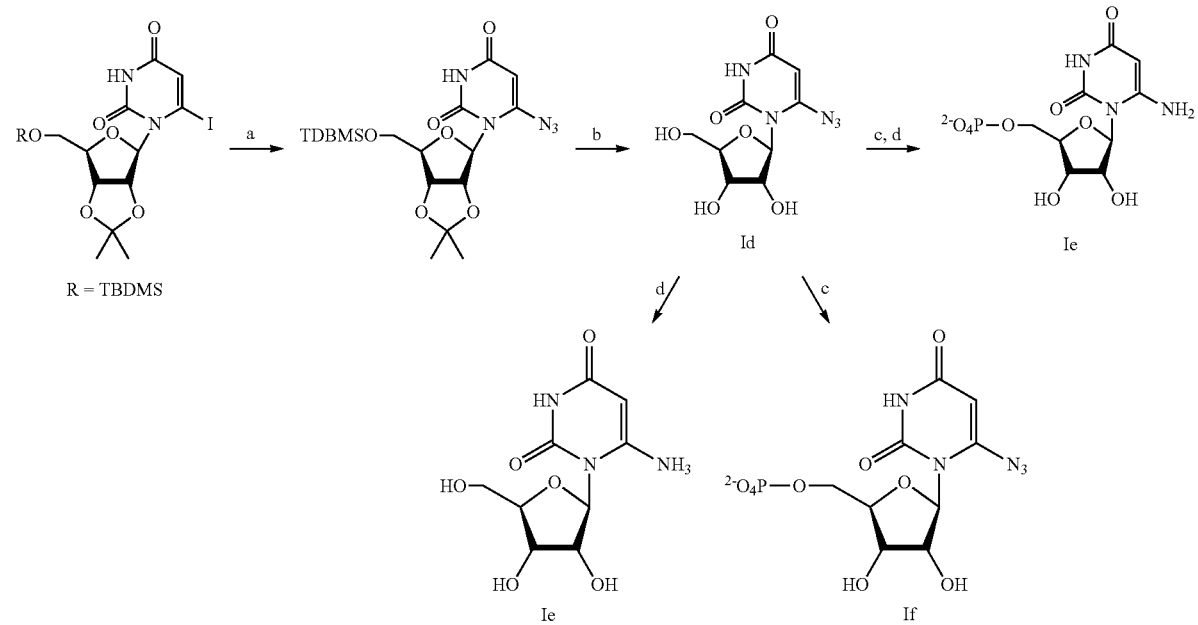

Reaction conditions: (a) NaN$_3$, DMF, r.t.; (b) 50% TFA, r.t.; (c) POCl$_3$, pyridine, H$_2$O, CH$_3$CN, 0° C.; (d) H$_2$, PD/C, MeOH, r.t.

Introduction of the iodo moiety at the C-6 position of fully protected uridine was achieved through LDA and iodine, and further substitution of the iodo by the azido group produced the 6-azido derivative shown in the above scheme.[xxxv] Deprotection of the isopropylidene and t-butyldimethylsilyl groups using trifluoroacetic acid yielded 6-azido-uridine Id. Monophosphorylation of Id with phosphorus oxychloride to afford its mononucleotide followed by the reduction of the azido group with Pd/C gave the compound 6-amino-uridine-5'-O-monophosphate Ie in good yield.[xxxvi,xxxvii,xxxviii] Reduction of the azido moiety in compound Id yielded 6-amino-uridine Ic. Phosphorylation of compound Ic with phosphorus oxychloride afforded its mononucleotide 6-azido-uridine-5'-O-monophosphate Ie.

(a) 6-Azido-5'-O-(t-butyldimethylsilyl)-2',3'-O-isopropylidene uridine. 5'-O-(t-Butyldimethylsilyl)-2',3'-O-isopropylidene-6-iodo uridine (0.25 g, 0.48 mmol) was dissolved in dry DMF (3 mL) and NaN$_3$ (0.034 g, 0.53 mmol) was added. The reaction mixture was stirred at room temperature for 1 hr in the dark. Organic solvent was evaporated under vacuum and the crude was dissolved in ethyl acetate (15 mL), washed with brine and dried (Na$_2$SO$_4$). Organic layers were evaporated and the crude was purified by silica gel column chromatography (1% EtOH:CHCl$_3$). Purification of the compound and solvent evaporation were performed in the dark to yield the title compound 6-azido-5'-O-(t-butyldimethylsilyl)-2',3'-O-isopropylidene uridine (0.19 g, 0.44 mmol) in 92% yield as a light brown solid. $^1$H NMR (CDCl$_3$) δ 0.06 (s, 6H), 0.89 (s, 9H), 1.34 (s, 3H) 1.54 (s, 3H), 3.74-3.85 (m, 2H), 4.08-4.15 (m, 1H), 4.80 (dd, 1H, J=4.8, 6.3 Hz), 5.14 (dd, 1H, J=1.5, 6.3 Hz), 5.50 (s, 1H), 6.09 (dd, 1H, J=1.5 Hz), 9.12 (brs, 1H).

(b) 6-Azido uridine (Id). A stirred solution of 6-azido-5'-O-(t-butyldimethylsilyl)-2',3'-O-isopropylidene uridine (0.300 g, 0.683 mmol) was treated with 50% aqueous trifluoroacetic acid (3 mL) at 0° C. The reaction mixture was then brought to r.t. and was stirred for an additional hour. Evaporation of the solvent and purification of the crude by column chromatography (10-15% EtOH in CHCl$_3$) gave 6-azido uridine Id (0.17 g, 0.61 mmol) in 89% yield as a light brown solid. UV (H$_2$O): λ$_{max}$=285 nm; $^1$H NMR (D$_2$O) δ 3.77 (dd, 1H, J=5.4, 12.0 Hz), 3.89-4.00 (m, 2H), 4.43 (t, J=6.9 Hz 1H), 4.77 (dd, 1H, J=3.6, 6.9 Hz), 5.76 (s, 1H), 6.07 (d, 1H, J=3.6 Hz). HRMS (ESI) Calculated for C$_9$H$_{11}$N$_5$O$_6$Na (M+Na$^+$) 308.0601, found 308.0597.

(c) 6-Azido uridine-5'-O-monophosphate (If). A stirred solution of water (0.03 g, 1.89 mmol) and POCl$_3$ (0.28 mL, 2.97 mmol) in anhydrous acetonitrile (3 mL) was treated with pyridine (0.26 mL, 3.24 mmol) at 0° C. and stirred for 10 min. 6-Azido uridine Id was added (0.25 g, 0.68 mmol) and the mixture was stirred for an additional 5 hr at 0° C. The reaction mixture was quenched with 25 mL of cold water and the stirring was continued for another hour. Evaporation of the solvent and purification of the crude by column chromatography (Dowex ion-exchange basic resin, 0.1 M formic acid) gave the mononucleotide If (0.23 g, 0.63 mmol) in 60% yield as syrup. UV (H$_2$O) λ$_{max}$=283 nm; $^1$H NMR (D$_2$O) δ 3.78-3.85 (m, 1H), 3.89-4.00 (m, 2H), 4.34 (t, J=6.9 Hz 1H), 4.80 (m, 1H), 5.73 (s, 1H), 6.04 (brs, 1H). $^{31}$P NMR (D$_2$O) δ ppm 2.47. HRMS (ESI, negative) Calculated for C$_9$H$_{11}$N$_5$O$_9$P (M$^-$) 364.0299, found 364.0307.

(d) 6-Amino uridine-5'-O-monophosphate Ie. The mononucleotide If (0.06 g, 0.15 mmol) was dissolved in 50% aqueous methanol and 10% Pd/C (10 mg) was added. The reaction mixture was stirred for 2 hr under the hydrogen atmosphere at room temperature. The mixture was filtered through Celite® and the solvent was evaporated to dryness to give 6-amino uridine-5'-O-monophosphate Ie as syrup in 85% yield (43 mg, 0.13 mmol). UV (H$_2$O) λ$_{max}$=270 nm; $^1$H NMR (D$_2$O) δ 3.96-4.05 (m, 2H), 4.12-4.24 (m, 2H), 4.51 (t, J=6.6 Hz 1H), 4.81 (s, 1H), 6.20 (d, J=6.6, 1H). HRMS (ESI, negative) Calculated for C$_9$H$_{13}$N$_3$O$_9$P (M$^-$) 338.0394, found 338.0403.

(e) 6-Amino uridine (Ic). Compound Ic was obtained by treating 6-Azido uridine (Id) with hydrogen in the presence of Pd/C in MeOH using the procedure described above in Example 2(d).

Example 3

Synthesis of Compounds Ig and Ih

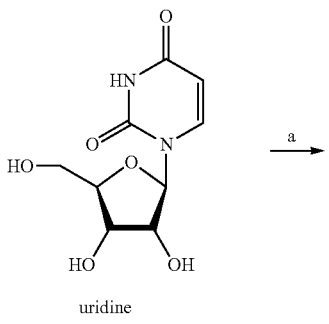
uridine

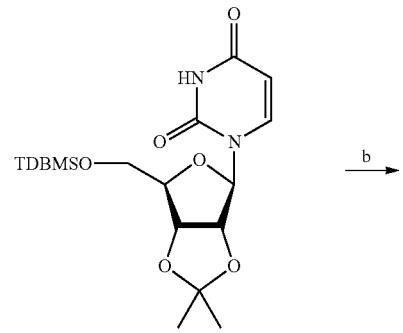

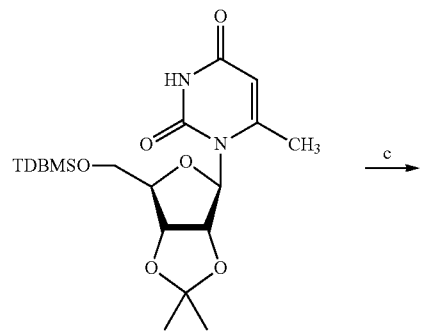

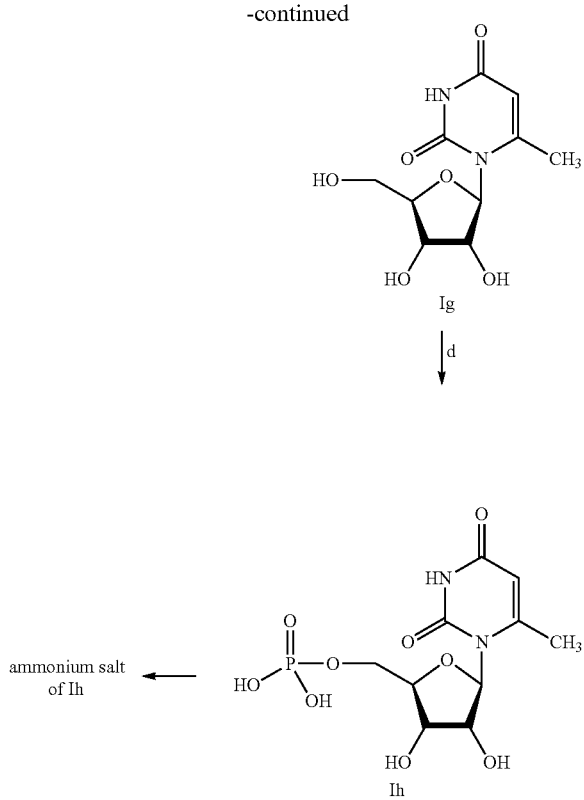

Reaction conditions: (a) i. acetone/H⁺, ii. TBDMSCl, imidazole/CH₂Cl₂, 0-25° C.; (b) LDA, CH₃I, THF, -78° C.; (c) 50% TFA, r.t.; (d) POCl₃, pyridine, H₂O, CH₃CN, 0° C.

Target molecules were synthesized from uridine according to literature methods[xxxix]. Introduction of the methyl group in C-6 position was achieved through LDA and methyl iodide.[xl] Deprotection of the protecting groups with TFA[xli] afforded compound Ig followed by monophosphorylation with phosphorus oxychloride[xlii,xliii] afforded the monophosphorylated nucleoside Ih. Finally, monophosphate compound Ih was transformed into the ammonium salt by neutralization with 0.5 M NH₄OH solution at 0° C. and freeze dried to obtain the ammonium salts as powder.

(a) 5'-O-(t-Butyldimethylsilyl)-2',3'-O-isopropylidene uridine. A stirred suspension of uridine (1 g, 4.098 mmol) in dry acetone (50 mL) was treated with H₂SO₄ (0.5 mL) drop wise at room temperature and the resulting mixture was stirred further 1 h and neutralized with Et₃N. Evaporation of the solvent and purification of the crude by column chromatography (5-8% MeOH in CHCl₃) gave 2',3'-O-isopropylidene uridine (1.15 g) in quantitative yield as a white solid ¹H NMR (CDCl₃) d: 1.36 (s, 3H, —CH₃), 1.57 (s, 3H, —CH₃), 3.80 (dd, 1H, J=3.3, 12.0 Hz, H-5'), 3.91 (dd, 1H, J=2.7, 12.0 Hz, H-5"), 4.26-4.30 (m, 1H, H-4'), 4.95 (dd, 1H, J=3.3, 6.3 Hz, H-3'), 5.02 (dd, 1H, J=2.7, 6.3 Hz, H-2') 5.56 (d, 1H, J=2.7 Hz, H-1'), 5.72 (d, 1H, J=8.1 Hz, H-5), 7.36 (d, 1H, J=8.1 Hz, H-6). A stirred solution of 2',3'-O-isopropylidene uridine (0.2 g, 0.704 mmol) in dry CH₂Cl₂ (3 mL) was treated with imidazole (0.095 g, 1.408 mmol) and TBDMSCl (0.105 g, 0.704 mmol) at 0° C. The reaction mixture was brought to room temperature and stirred for 1 h. The solvent was evaporated under vacuum and the solid was taken into ethyl acetate (30 mL), washed with water (15 mL), brine (15 mL) and dried (Na₂SO₄). Evaporation of the solvent and purification of crude by column chromatography (5% MeOH in CHCl₃) gave 5'-O-(t-butyldimethylsilyl)-2',3'-O-isopropylidene uridine (0.268 mg) in 96% yield as a foamy solid. ¹H NMR (CDCl₃): δ 0.10 (s, 6H, —CH₃), 0.90 (s, 9H, —CH₃), 1.36 (s, 3H, —CH₃) 1.59 (s, 3H, —CH₃), 3.79 (dd, 1H, J=2.7, 11.2 Hz, H-5'), 3.92 (dd, 1H, J=2.4, 11.2 Hz, H-5"), 4.30-4.33 (m, 1H, H-4'), 4.67 (dd, 1H, J=2.7, 6.0 Hz, H-3'), 4.75 (dd, 1H, J=3.0, 6.0 Hz, H-2'), 5.66 (d, 1H, J=8.1 Hz, H-5), 5.96 (dd, 1H, J=3.0 Hz, H-1'), 7.68 (d, 1H, J=8.1 Hz, H-6), 8.47 (brs, 1H, —NH).

(b) 5'-O-(t-Butyldimethylsilyl)-6-methyl-2',3'-O-isopropylidene uridine. A stirred solution of LDA (0.62 mL, 1.256 mmol, 2.0 M solution in THF) in dry THF (2 mL) was treated with 5'-O-(t-butyldimethylsilyl)-2',3'-O-isopropylidene uridine (0.25 g, 0.628 mmol) in dry THF 1.5 mL at −78° C. After stirring for 1 h, methyl iodide (0.628 mmol) in dry THF (2 mL) was added and the mixture was stirred for further 5 h at same temperature. The reaction was quenched with AcOH (0.3 mL), then brought to room temperature and dissolved in ethyl acetate (25 mL). The organic layer was washed with saturated NaHCO₃ solution (10 mL), brine (10 mL) and dried (Na₂SO₄). Evaporation of the solvent and purification of crude by column chromatography (hexanes-ethyl acetate, 70:30) gave 5'-O-(t-butyldimethylsilyl)-6-methyl-2',3'-O-isopropylidene uridine as a foamy white solid.

(c) 6-Methyl uridine (Ig). A stirred solution of 5'-O-(t-butyldimethylsilyl)-6-methyl-2',3'-O-isopropylidene (0.300 g) was treated with 50% aqueous trifluoroacetic acid (3 mL) at 0° C. and then brought to room temperature and stirred for 2 h. Evaporation of solvent and purification of crude by column chromatography (10-15% EtOH in CHCl₃) gave 6-methyl uridine (Ig) as a white solid.

(d) 6-Methyl uridine-5'-O-monophosphate (Ih). A stirred solution of H₂O (0.034 g, 1.89 mmol) and POCl₃ (0.277 mL, 2.973 mmol) in dry acetonitrile (3 mL) was treated with pyridine (0.261 mL, 3.24 mmol) at 0° C. and stirred for 10 min. 6-Methyl uridine (Ig) was added (0.675 mmol) and the mixture was stirred for further 5 h at same temperature. The reaction mixture was quenched with 25 mL of cold water and stirring was continued for further 1 h. Evaporation of solvent and purification of crude by column chromatography (Dowex ion-exchange basic resin, 0.1M formic acid) gave 6-methyl uridine-5'-O-monophosphate (Ih) as syrup. The monophosphate derivative was converted to the di-ammonium salt as described earlier.

Example 4

Synthesis of 6-iodo uridine (Ii) and 6-iodo-uridine-5'-O-monophosphate (Ij)

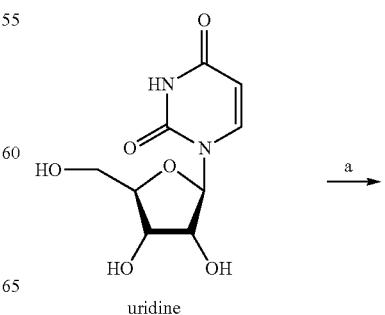

uridine

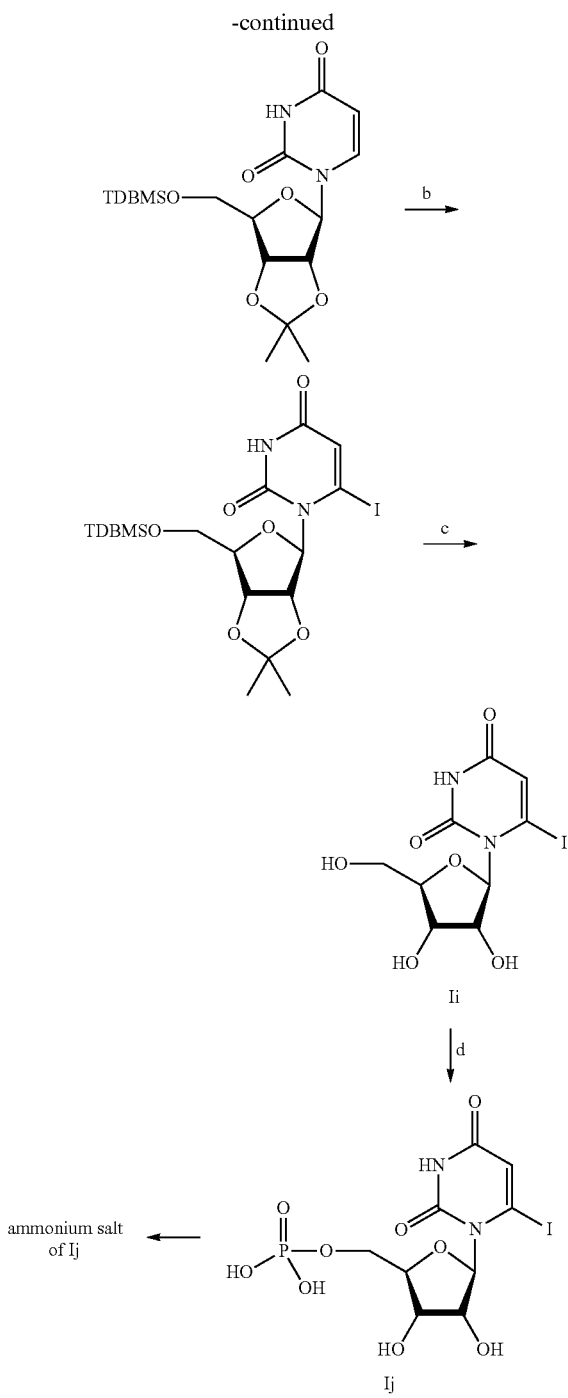

Reaction conditions: (a) i. acetone/H⁺, ii. TBDMSCl, imidazole/CH₂Cl₂, 0-25° C.; (b) LDA, I₂, THF, -78° C.; (c) 50% TFA, r.t.; (d) POCl₃, pyridine, H₂O, CH₃CN, 0° C.

Compounds Ii and Ij were synthesized from uridine. Introduction of the iodo moiety at the C-6 position of protected uridine was achieved using lithium diisopropylamide followed by treatment with iodine.[xliv] Deprotection with TFA followed gave compound Ii, and the subsequent phosphorylation with phosphorus oxychloride afforded the mononucleotide Ij.[xlv,xlvi,xlvii] Then, the compound Ij was transformed into its ammonium salt by neutralization with 0.5 M NH₄OH solution at 0° C. and freeze-dried to get the ammonium salt as a powder.

(a) 5'-O-(t-Butyldimethylsilyl)-2',3'-O-isopropylidene uridine. A stirred suspension of uridine (1 g, 4.1 mmol) in anhydrous acetone (50 mL) was treated with H₂SO₄ (0.5 mL) drop wise at room temperature and the resulting mixture was stirred for an additional hour. The reaction was then neutralized with Et₃N and was concentrated. The crude mixture was purified by column chromatography (5-8% MeOH:CHCl₃) to afford 2',3'-O-isopropylidene uridine (1.15 g, quant.) as a white solid. ¹H NMR (CDCl₃) d ppm 1.36 (s, 3H, —CH₃), 1.57 (s, 3H, —CH₃), 3.80 (dd, 1H, H-5'), 3.91 (dd, 1H, H-5"), 4.26-4.30 (m, 1H, H-4'), 4.95 (dd, 1H, H-3'), 5.02 (dd, 1H, H-2') 5.56 (d, 1H, H-1'), 5.72 (d, 1H, H-5), 7.36 (d, 1H, H-6).

A stirred solution of 2',3'-O-isopropylidene uridine (0.2 g, 0.7 mmol) in anhydrous CH₂Cl₂ (3 mL) was treated with imidazole (0.095 g, 1.4 mmol) and TBDMSiCl (0.105 g, 0.7 mmol) at 0° C. The reaction mixture was brought to room temperature and stirred for an additional hour. The solvent was evaporated under vacuum and the crude was dissolved in ethyl acetate (30 mL), washed with water (15 mL), brine (15 mL) and dried (Na₂SO₄). Evaporation of the solvent and purification of the crude by column chromatography (5% MeOH in CHCl₃) yielded 5'-O-(t-butyldimethylsilyl)-2',3'-O-isopropylidene uridine (0.27 mg, 96% yield) as a foam: ¹H NMR (CDCl₃) d ppm 0.10 (s, 6H, CH₃), 0.90 (s, 9H, CH₃), 1.36 (s, 3H, CH₃) 1.59 (s, 3H, CH₃), 3.79 (dd, 1H, H-5'), 3.92 (dd, 1H, H-5"), 4.30-4.33 (m, 1H, H-4'), 4.67 (dd, 1H, H-3'), 4.75 (dd, 1H, H-2'), 5.66 (d, 1H, H-5), 5.96 (dd, 1H, H-1'), 7.68 (d, 1H, H-6), 8.47 (brs, 1H, —NH).

(b) 5'-O-(t-Butyldimethylsilyl)-6-iodo-2',3'-O-isopropylidene uridine. A stirred solution of LDA (0.62 mL, 1.3 mmol, 2.0 M solution in THF) in anhydrous THF (2 mL) was treated with 5'-O-(t-butyldimethylsilyl)-2',3'-O-isopropylidene uridine (0.25 g, 0.6 mmol) dissolved in 1.5 mL anhydrous THF, at −78° C. After stirring for 1 h, iodine (0.16 g, 0.6 mmol) in anhydrous THF (2 mL) was added and the mixture was stirred for an additional 5 h at the same temperature. The reaction was quenched with AcOH (0.3 mL), then brought to room temperature and dissolved in ethyl acetate (25 mL). The organic layer was washed with saturated NaHCO₃ solution (10 mL), 5% Na₂S₂O₃ solution (10 mL), brine (10 mL) and dried (Na₂SO₄). Evaporation of the solvent and purification of the crude by column chromatography (hexanes-ethyl acetate, 70:30) gave 5'-O-(t-butyldimethylsilyl)-6-iodo-2',3'-O-isopropylidene uridine (0.224 g, 68%) as a yellow foam: ¹H NMR (CDCl₃) d ppm 0.06 (s, 6H, CH₃), 0.89 (s, 9H, 3CH₃), 1.35 (s, 3H, CH₃) 1.56 (s, 3H, CH₃), 3.76-3.86 (m, 2H, H-5', H-5"), 4.15-4.20 (m, 1H, H-4'), 4.81 (dd, 1H, J=4.2, 6.3 Hz, H-3'), 5.18 (dd, 1H, J=2.0, 6.3 Hz, H-2'), 6.09 (s, 1H, H-5), 6.45 (dd, 1H, J=2.0 Hz, H-1'), 8.78 (brs, 1H, NH).

(c) 6-Iodo-uridine (Ii). A stirred solution of 5'-O-(t-butyldimethylsilyl)-6-iodo-2',3'-O-isopropylidene uridine (0.300 g, 0.572 mmol) was treated with 50% aqueous TFA (3 mL) at 0° C., brought to room temperature and stirred for 2 h in the dark. Evaporation of the solvent and purification of the crude by column chromatography (10-15% EtOH in CHCl₃) afforded 6-iodo uridine Ii (0.182 g, 0.49 mmol, 86%) as a light brown solid. UV (H₂O): λ$_{max}$=268 nm (e=8975); ¹H NMR (D₂O) δ ppm 3.77 (dd, 1H, H-5'), 3.91 (dd, 1H, H-5"), 3.978-4.032 (m, 1H, H-4'), 4.43 (t, 1H, H-3'), 4.84 (dd, 1H, H-2'), 6.06 (d, 1H, H-1'), 6.67 (s, 1H, H-5). HRMS (ESI) calculated for C₉H₁₁N₂O₆NaI (M+Na⁺) 392.9554, found 392.9565.

(d) 6-Iodo uridine-5'-O-monophosphate (Ij). A stirred solution of H₂O (0.034 g, 1.89 mmol) and POCl₃ (0.28 mL, 2.97 mmol) in anhydrous acetonitrile (3 mL) was treated with pyridine (0.261 mL, 3.24 mmol) at 0° C. and stirred for 10 min. 6-Iodo uridine (0.250 g, 0.67 mmol) was added and the mixture was stirred for an additional 5 h at 0° C. The reaction mixture was then quenched with 25 mL of cold water and continued stirring for an additional hour. The evaporation of the solvent and purification of the crude by column chromatography (Dowex ion-exchange basic resin, 0.1 M formic acid) afforded 6-iodo uridine-5'-O-monophosphate (Ij) (0.207 g, 68%) as a syrup. UV (H$_2$O): $\lambda_{max}$=267 nm (e=2890); $^1$H NMR (D$_2$O) δ ppm 3.78 (dd, 1H, H-5'), 3.91 (dd, 1H, H-5"), 3.98-4.03 (m, 1H, H-4'), 4.43 (t, H-3'), 4.84 (dd, 1H, H-2'), 6.05 (d, 1H, H-1'), 6.67 (s, 1H, H-5). $^{31}$P NMR (D$_2$O) δ ppm 2.214. HRMS (ESI, negative) calculated for C$_9$H$_{11}$N$_2$O$_9$PI (M$^-$) 448.9252, found 448.9263.

Example 5

Synthesis of Compounds Ik, Ii and Im

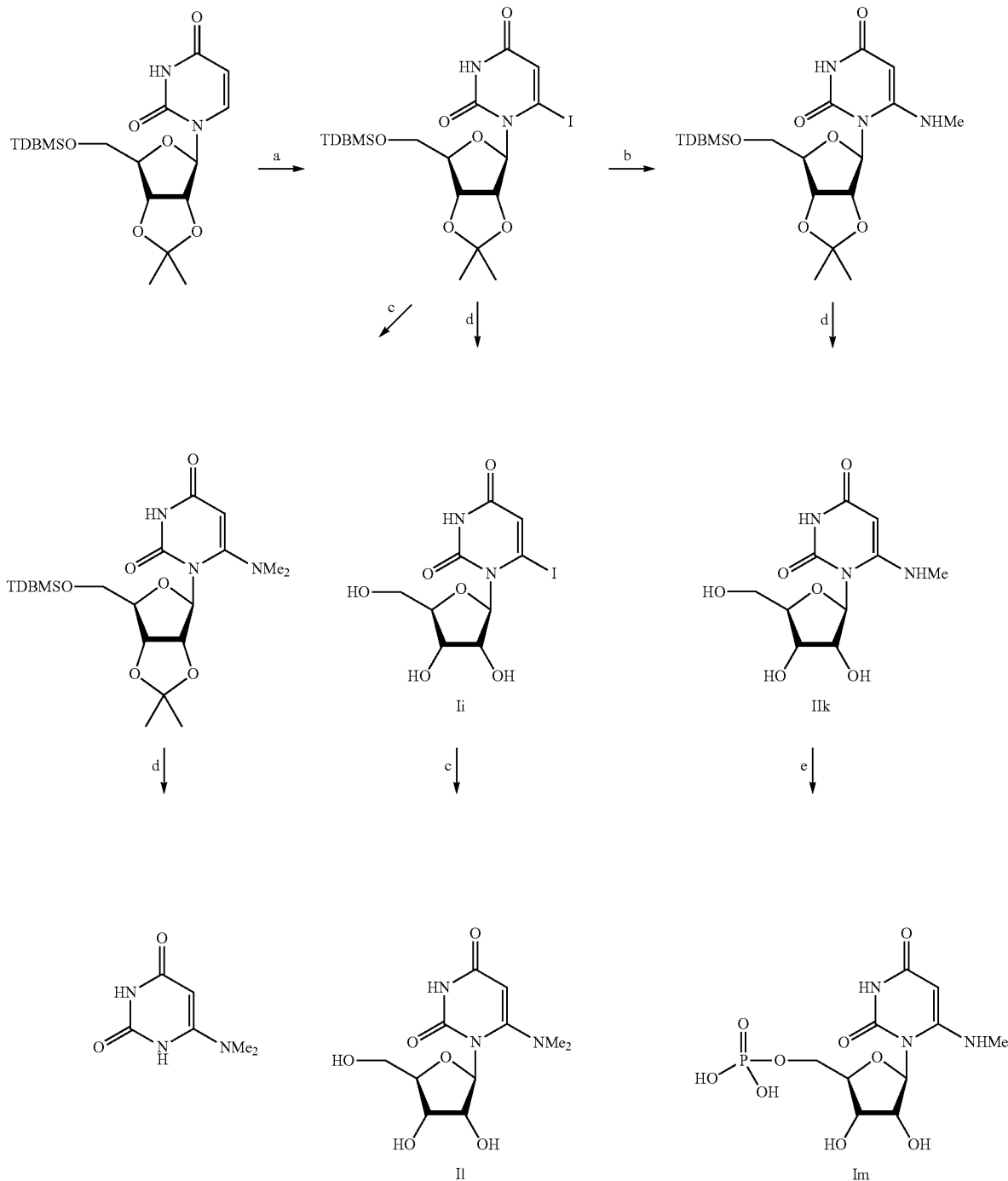

Reaction conditions: (a) THF, I$_2$, -78° C., LDA; (b) NH$_2$Me, EtOH, TEA; (c) NHMe$_2$, EtOH, TEA; (d) TFA, H$_2$O; (e) POCl$_3$, pyridine, H$_2$O, CH$_3$CN.

(a) 5'-O-(t-Butyldimethylsilyl)-6-N-methylamino-2',3'-O-isopropylidene uridine. 5'-O-(t-Butyldimethylsilyl)-6-iodo-2',3'-O-isopropylidene uridine (262 mg, 0.5 mmol) was dissolved 20 mL of dry ethanol, then methylamine (187 mg) was added, followed by adding triethyl amine (1 mL). Reaction mixture was stirred at rt for 3 h and all the start material was consumed. The reaction mixture was evaporated to dryness and purified by column chromatography, ($CHCl_3$:MeOH=9:1) to obtain 98 mg of 5'-O-(t-Butyldimethylsilyl)-6-methylamino-2',3'-O-isopropylidene uridine (yield 50%).

(b) 5'-O-(t-Butyldimethylsilyl)-6-N,N-dimethylamino-2',3'-O-isopropylidene uridine. The procedure was the same as above, except that dimethyl amine was used instead of methyl amine. The reaction was complete in 3 h. The solvent was Hexane:EtoAc=1:1 to purify the product using column chromatography (yield 77.1%).

(c) 6-N,N-Dimethylamino uracil. TFA (10 mL) and $H_2O$ (10 mL) were mixed and cooled to 0° C. and added to the flask with 5'-O-(t-butyldimethylsilyl)-6-N,N-dimethylamino-2',3'-O-isopropylidene uridine. The mixture was stirred at this temperature for 2 h, followed by an additional hour at room temperature. The mixture was evaporated to dryness, neutralized the mixture with triethyl amine and the resulting mixture was purified by column chromatography ($CHCl_3$:MeOH=17:3) to obtain 6-N,N-dimethylamino uracil.

(d) 6-Iodouridine (Ii). 5'-O-(t-Butyldimethylsilyl)-6-iodo-2',3'-O-isopropylidene uridine was treated with trifluoroacetic acid and the product was purified using column chromatography.

(e) 6-N,N-Dimethylamino uridine (Ij)). 6-Iodouridine (Ii) was treated with dimethyl amine in ethanol and triethyl amine, as described above. The product was purified by column chromatography (EtOAc:MeOH=8:1) to get 70 mg of 6-N,N-dimethylamino uridine (Ii) with an yield of 90.3%.

(f) 6-N-Methylamino uridine (Ik). 5'-O-(t-Butyldimethylsilyl)-6-N-methylamino-2',3'-O-isopropylidene uridine was treated with trifluoroacetic acid in water to obtain 6-N-methylamino uridine (Ik).

(g) 6-N-Methylamino uridine-5'-O-monophosphate (Im). A stirred solution of $POCl_3$ (67 mg, 0.44 mmol), $H_2O$ (5 mg) and $CH_3CN$ (0.5 mL) was treated with pyridine (37 mg) at 0° C. 6-N-Methylamino uridine Ik (30 mg, 0.11 mmol) was added and stirred at this temperature for 3 h. The reaction mixture was quenched with 1 mL of cold water and stirred for an additional hour. The mixture was evaporated under reduced pressure and the residue was purified by HPLC to obtain 2 mg of 6-N-methylamino uridine-5'-O-monophosphate (Im).

Example 6

Extension to 5-Fluoro Substituted Analogs

5-Fluoro-6-amino uridine (In), 5-fluoro-6-azido uridine (Io), 5-fluoro-6-iodo uridine (Ip), and their mononucleotide forms (Iq, Ir and Is, respectively) were synthesized using the procedures described in Examples 1-5, by substituting uridine with 5-fluoro uridine as the starting material.

Other compounds can be synthesized by utilizing the appropriately protected nucleosides and substituting the C6 substituents as shown in the above examples. Most of the procedures are common in the literature and can be carried out by persons with technical skills in the art.

Example 7

Synthesis of Compounds It and Iu

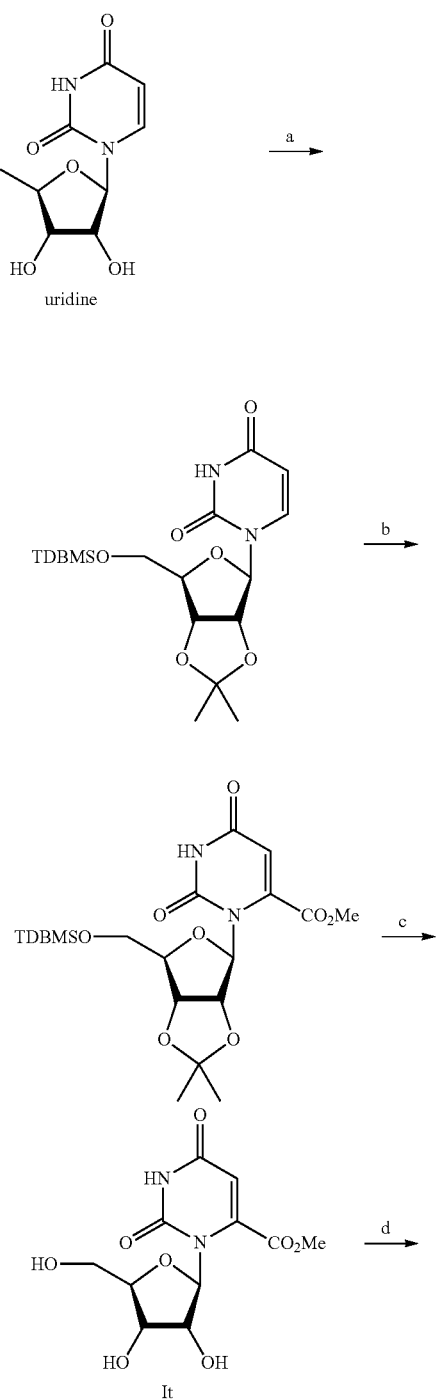

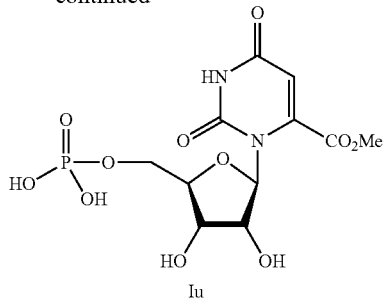

Iu

Reaction conditions: (a) i. acetone/H+, ii, TBDMSCl, imidazole/CH₂Cl₂, 0-25° C.; (b) LDA, ClCO₂Me, THF, -78° C.; (c) 50% TFA, r.t.; (d) POCl₃, pyridine, H₂O, CH₃CN, 0° C.

Compounds It and Iu were synthesized from uridine. Introduction of methoxycarbonyl in C-6 position was achieved through LDA and methyl chloroformate. Deprotection of the protecting groups with TFA followed by the mono-phosphorylation with phosphorus oxychloride afforded the monophosphorylated nucleoside. Finally, monophosphate compound Iu was transformed into the ammonium salt by neutralization with 0.5 M NH₄OH solution at 0° C. and freeze dried to yield the ammonium salts as powder.

(a) 5'-O-(ᵗ-Butyldimethylsilyl)2',3'-O-isopropylidene uridine. A stirred suspension of uridine (1 g, 4.098 mmol) in dry acetone (50 mL) was treated with H₂SO₄ (0.5 mL) drop wise at room temperature and the resulting mixture was stirred further 1 h and neutralized with Et₃N. Evaporation of the solvent and purification of the crude by column chromatography (5-8% MeOH in CHCl₃) gave 2',3'-O-isopropylidene uridine (1.15 g) in quantitative yield as a white solid $^1$H NMR (CDCl₃) d: 1.36 (s, 3H, —CH₃), 1.57 (s, 3H, —CH₃), 3.80 (dd, 1H, J=3.3, 12.0 Hz, H-5'), 3.91 (dd, 1H, J=2.7, 12.0 Hz, H-5"), 4.26-4.30 (m, 1H, H-4'), 4.95 (dd, 1H, J=3.3, 6.3 Hz, H-3'), 5.02 (dd, 1H, J=2.7, 6.3 Hz, H-2') 5.56 (d, 1H, J=2.7 Hz, H-1'), 5.72 (d, 1H, J=8.1 Hz, H-5), 7.36 (d, 1H, J=8.1 Hz, H-6). A stirred solution of 2,3-O-isopropylideneuridine (0.2 g, 0.704 mmol) in dry CH₂Cl₂ (3 mL) was treated with imidazole (0.095 g, 1.408 mmol) and TBDMSCl (0.105 g, 0.704 mmol) at 0° C. The reaction mixture was brought to room temperature and stirred for 1 h. The solvent was evaporated under vacuum and the solid was taken into ethyl acetate (30 mL), washed with water (15 mL), brine (15 mL) and dried (Na₂SO₄). Evaporation of the solvent and purification of crude by column chromatography (5% MeOH in CHCl₃) gave 2 (0.268 mg) in 96% yield as a foamy solid. $^1$H NMR (CDCl₃): δ 0.10 (s, 6H, —CH₃), 0.90 (s, 9H, —CH₃), 1.36 (s, 3H, —CH₃) 1.59 (s, 3H, —CH₃), 3.79 (dd, 1H, J=2.7, 11.2 Hz, H-5'), 3.92 (dd, 1H, J=2.4, 11.2 Hz, H-5"), 4.30-4.33 (m, 1H, H-4'), 4.67 (dd, 1H, J=2.7, 6.0 Hz, H-3'), 4.75 (dd, 1H, J=3.0, 6.0 Hz, H-2'), 5.66 (d, 1H, J=8.1 Hz, H-5), 5.96 (dd, 1H, J=3.0 Hz, H-1'), 7.68 (d, 1H, J=8.1 Hz, H-6), 8.47 (brs, 1H, —NH).

(b) 5'-O-(ᵗ-Butyldimethylsilyl)-6-Methoxycarbonyl-2',3'-O-isopropylidene uridine. A stirred solution of 5'-O-(ᵗ-butyldimethylsilyl)2',3'-O-isopropylidene uridine (0.25 g, 0.628 mmol) in dry THF (2 mL) was treated with LDA (0.62 mL, 1.256 mmol, 2.0 M solution in THF) at −78° C. After stirring for 1 h, methylchloroformate (0.048 g, 0.628 mmol) in dry THF (2 mL) was added and the mixture was stirred for further 5 h at same temperature. The reaction was quenched with AcOH (0.3 mL), then brought to room temperature and dissolved in ethyl acetate (25 mL). The organic layer was washed with saturated NaHCO₃ solution (10 mL), 5% Na₂S₂O₃ solution (10 mL), brine (10 mL) and dried (Na₂SO₄). Evaporation of the solvent and purification of crude by column chromatography (hexanes-ethyl acetate, 70:30) gave the title compound (0.18 g) in 64% yield as a syrup. $^1$H NMR (CDCl₃): d 0.056 (s, 6H, —CH₃), 0.88 (s, 9H, —CH₃), 1.34 (s, 3H, —CH₃) 1.54 (s, 3H, —CH₃), 3.75 (dd, 1H, J=7.2, 10.9 Hz, H-5'), 3.81 (dd, 1H, J=5.1, 10.9 Hz, H-5'), 3.93 (s, 3H —CH₃), 4.06-4.12 (m, 1H, H-4'), 4.71 (dd, 1H, J=4.8, 6.4 Hz, H-3'), 5.15 (dd, 1H, J=2.0, 16.4 Hz, H-2'), 5.89 (d, 1H, J=2.1 Hz, H-1'), 6.07 (s, 1H, H-5), 9.32 (brs, 1H, —NH).

(c) 6-Methoxycarbonyl uridine (It). A stirred solution of compound 5'-O-(ᵗ-butyldimethylsilyl)-6-Methoxycarbonyl-2',3'-O-isopropylidene uridine (0.23 g, 0.504 mmol) was treated with 50% aqueous TFA (3 mL) at 0° C. and then brought to room temperature and stirred for 2 h. Evaporation of solvent and purification of crude by column chromatography (10-15% EtOH in CHCl₃) yielded It (0.135 g) in 89% yield as a solid. $^1$H NMR (DMSO-D₂O): δ 3.37 (dd, 1H, J=6.6, 12.0 Hz, H-5'), 3.54 (dd, 1H, J=3.6, 12.0 Hz, H-5"), 3.62-3.67 (m, 1H, H-4'), 3.80 (s, 3H, —CO₂CH₃), 388-3.97 (m, 1H, H-3'), 4.41 (dd, 1H, J=4.2, 6.3 Hz, H-2'), 5.34 (d, 1H, J=4.2 Hz, H-1'), 5.95 (s, 1H, H-5).

(d) 6-Methoxycarbonyluridine-5'-O-monophosphate (Iu). A stirred solution of H₂O (0.02 g, 1.112 mmol) and POCl₃ (0.16 mL, 1.748 mmol) in dry acetonitrile (3 mL) was treated with pyridine (0.154 mL, 1.907 mmol) at 0° C. and stirred for 10 min. Compound It was added (0.12 g, 0.397 mmol) and the mixture was stirred for further 5 h at same temperature. The reaction mixture was quenched with 25 mL of cold water and stirring was continued for further 1 h. Evaporation of solvent and purification of crude by column chromatography (Dowex ion-exchange basic resin, 0.1M formic acid) gave Iu as syrup. UV (H₂O): λ$_{max}$=274 nm; $^1$H NMR (D₂O): δ 3.99 (s, 3H —CO₂CH₃), 4.02-4.08 (m, 2H, H-5',5"), 4.16-4.23 (m, 1H, H-4'), 4.37 (t, J=6.6 Hz 1H, H-3'), 4.75 (dd, 1H, J=3.3, 6.6 Hz, H-2'), 5.70 (d, 1H, J=3.6 Hz, H-1'), 6.26 (s, 1H, H-5).

Example 8

Synthesis of Compounds Iv and Iw

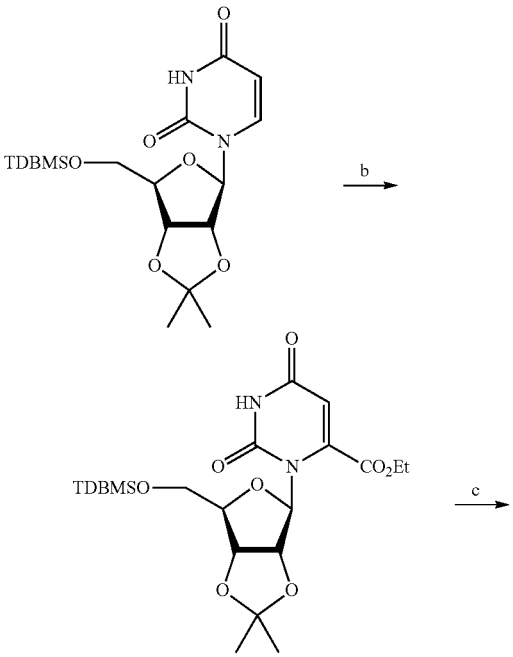

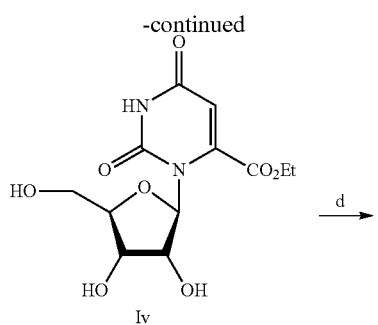

Iv

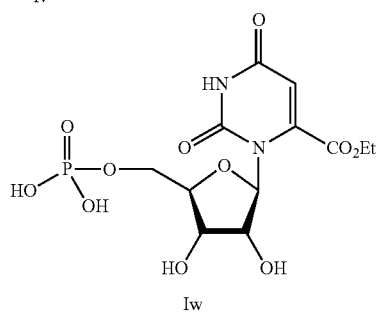

Iw

Reactions conditions: (b) LDA, ClCO$_2$Et, THF, -78° C.; (c) 50% TFA, r.t.; (d) POCl$_3$, pyridine, H$_2$O, CH$_3$CN, 0° C.

Target molecules Iv and Iw were synthesized from 5'-O-($^t$-butyldimethylsilyl)2',3'-O-isopropylidene uridine. Introduction of ethoxycarbonyl in C-6 position was achieved through LDA and ethyl chloroformate. Deprotection of the protecting groups with TFA followed by the mono-phosphorylation with phosphorus oxychloride afforded the mono-phosphorylated nucleoside Iv. Monophosphate Iw was transformed into the ammonium salt by neutralization with 0.5 M NH$_4$OH solution at 0° C. and freeze dried to get the ammonium salts as powder.

(a) 5'-O-($^t$-Butyldimethylsilyl)-6-Ethoxycarbonyl-2',3'-O-isopropylidene uridine. A stirred solution of 5'-O-($^t$-bu-tyldimethylsilyl)2',3'-O-isopropylidene uridine (0.25 g, 0.628 mmol) in dry THF (2 mL) was treated with LDA (0.62 mL, 1.256 mmol, 2.0 M solution in THF) at −78° C. After stirring for 1 h, ethyl chloroformate (0.048 g, 0.628 mmol) in dry THF (2 mL) was added and the mixture was stirred for further 5 h at same temperature. The reaction was quenched with AcOH (0.3 mL), then brought to room temperature and dissolved in ethyl acetate (25 mL). The organic layer was washed with saturated NaHCO$_3$ solution (10 mL), 5% Na$_2$S$_2$O$_3$ solution (10 mL), brine (10 mL) and dried (Na$_2$SO$_4$). Evaporation of the solvent and purification of crude by column chromatography (hexanes-ethyl acetate, 70:30) gave the title compound (0.18 g) in 64% yield as a syrup.

(b) 6-Ethoxycarbonyl uridine (Iv). A stirred solution of 5'-O-($^t$-butyldimethylsilyl)-6-Ethoxycarbonyl-2',3'-O-isopropylidene uridine (0.23 g, 0.504 mmol) was treated with 50% aqueous TFA (3 mL) at 0° C. and then brought to room temperature and stirred for 2 h. Evaporation of solvent and purification of crude by column chromatography (10-15% EtOH in CHC$_3$) gave Iv (0.135 g) in 89% yield as a solid.

(c) 6-Ethoxycarbonyluridine-5'-O-monophosphate (Iw). A stirred solution of H$_2$O (0.02 g, 1.112 mmol) and POCl$_3$ (0.16 mL, 1.748 mmol) in dry acetonitrile (3 mL) was treated with pyridine (0.154 mL, 1.907 mmol) at 0° C. and stirred for 10 min. Compound Iv was added (0.12 g, 0.397 mmol) and the mixture was stirred for further 5 h at same temperature. The reaction mixture was quenched with 25 mL of cold water and stirring was continued for further 1 h. Evaporation of solvent and purification of crude by column chromatography (Dowex ion-exchange basic resin, 0.1M formic acid) gave Iw as syrup. Monophosphate Iw was transformed into the ammonium salt by neutralization with 0.5 M NH$_4$OH solution at 0° C. and freeze dried to get the ammonium salts as powder.

Example 9

Synthesis of compound Ix

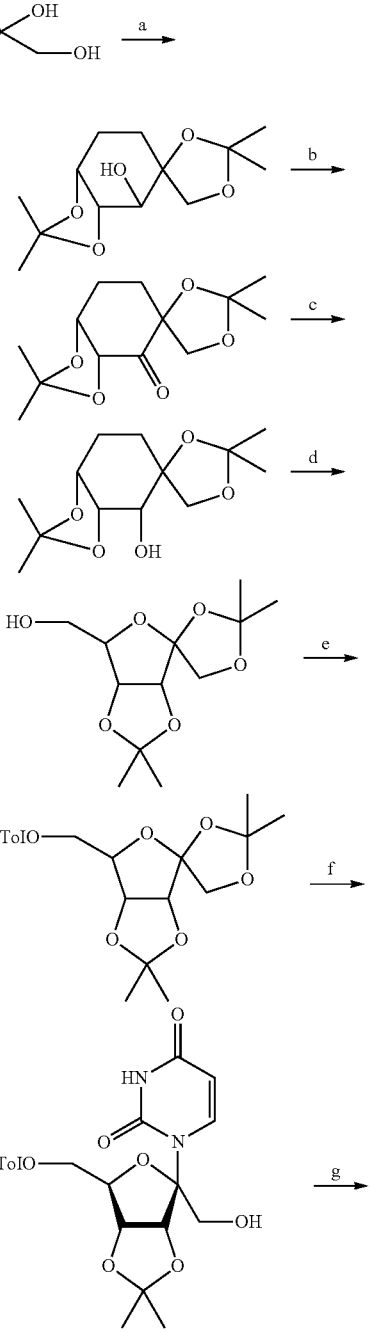

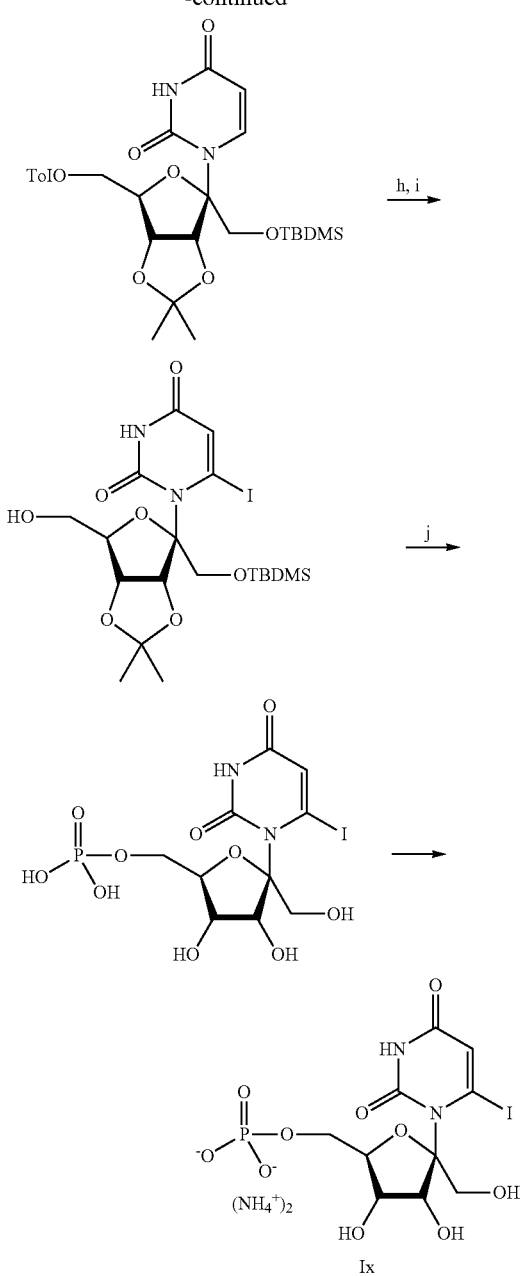

Reaction conditions: (a) acetone, conc. H₂SO₄, r.t.; (b) PCC, 4 angstrom molecular sieves, DCM, r.t.; (c) NaBH₄, EtOH, 0° C.; (d) 50% HClO₄, dimethoxypropoane, acetone, r.t.; (e) p-methyl-benzoyl chloride, triethylamine, DCM; (f) presilylated uracil, TMSOTf, CH₃CN, 0° C. to r.t.; (g) TBDMSCl, DMAP, TEA, DCM, r.t.; (h) LDA, I₂, THF, -78° C.; (i) 7N NH₃ in methanol, r.t.; (j) POCl₃, pyridine, H₂O, CH₃CN, 0° C.

D-Fructose was selectively protected, oxidized and then reduced. Rearrangement of the resulting compound was achieved through 2,2-dimethoxypropane and catalytic amount of 50% HClO₄ in acetone. The coupling of the modified sugar with uracil in dry acetonitrile produced a mixture of two isomers, the α-isomer and β-isomer, in ~1:1 ratio. The desired β-isomer may be iodinated and deprotected with 7N NH₃ in methanol and phosphorylated to give desired monophosphate in one step. The protection groups will come off during hydrolysis. Finally the nucleoside may be converted to ammonium salt Ix.

(a) 1,2:4,5-Di-O-isopropylidine-β-fructopyranose

To a suspension of D-Fructose (15 g, 83.26 mmol) in dry acetone was added concentrated H₂SO₄ (1.4 mL) by syringe at room temperature. The suspension was stirred at rt and turned clear slowly over a period of 3 h. It was cooled to 0° C. and a solution of NaOH (4.65 g) in water (42 mL) was added to neutralize the sulfuric acid. The solvent was removed under reduced pressure and the residue was extracted with methylene chloride (2×). The combined extracts were washed with water (2×) and then dried over anhydrous Na₂SO₄. After filtration, the solvent was removed to give crude as white solid. The crude was dissolved in dimethyl ether and hexane was added to precipitate the pure product (8.5 g) as a white solid.

(b) 1,2:4,5-Di-O-isopropylidine-β-D-erytro-2,3-hexodiulo-2,6-pyranose

To a mixture of 1,2:4,5-di-O-isopropylidine-β-fructopyranose (8.24 g, 31.67 mmol, 1.0 equiv.) and powdered 4 Å molecule sieve (20 g) in dichloromethane (200 mL) was added PCC (20.5 g, 3.0 equiv.) in portions over a period of 20 min at room temperature under N₂. The mixture was stirred at r.t. for 5 h and then diluted with large amount of ether and filtered. The filtrate was passed through a pad of celite. The filtrate was passed through a pad of silica gel. The solvent was removed under vacuum to afford product as a white solid (7.8 g, 95% yield). It was used for next reaction without further purification.

(c) 1,2:4,5-Di-O-isopropylidine-β-D-psicopyranose

To a solution of 1,2:4,5-di-O-isopropylidine-β-D-erytro-2,3-hexodiulo-2,6-pyranose (16.4 g, 63.52 mmol, 1.0 equiv.) in ethanol (160 mL) was added NaBH₄ solid (1.45 g, 38.11 mmol, 0.6 equiv.) in one portion at 15° C. The mixture was stirred for 1.5 h and then evaporated to almost dryness under reduced pressure. A saturated solution of NH₄Cl (100 mL) was added and the mixture was stirred for 3 h at rt. It was extracted with ether (3×). The combined extracts were washed with brine (2×), dried over anhydrous Na₂SO₄ and filtered. The solvent was removed to give crude as oil, which was used for next reaction directly.

(d) 1,2:3,4-Di-O-isopropylidine-β-D-psicofuranose

To a solution of crude 1,2:4,5-di-O-isopropylidine-β-D-psicopyranose (14.4 g) in acetone (150 mL) was added dimethoxypropane (4 mL) and 60% HClO₄ (1.0 mL) at 0° C. The mixture was stirred for 3 h at the same temperature. A solution of ammonium hydroxide (2 mL) was added. After evaporation, water was added. The mixture was extracted with ether (3×). The combined extracts were washed with brine (2×), dried over anhydrous Na₂SO₄ and filtered. Evaporation of solvent gave crude product (10.5 g) as an oil, which solidified after vacuum-drying.

(e) 6-O-(4-Toluoyl)-1,2:3,4-di-O-isopropylidene-D-psicofuranose

To a stirring solution of crude 1,2:3,4-di-O-isopropylidine-β-D-psicofuranose (10.5 g, 40.35 mmol, 1.0 equiv.), DMAP (0.49 g, 4.035 mmol, 0.1 equiv.) and TEA (20.42 g, 201.75 mmol, 5.0 equiv.) was added p-toluoyl chloride (6.86 g, 44.39 mmol, 1.1 equiv.) drop wise at 0° C. The resulting light yellow solution was allowed to reach r.t. slowly and then stirred at r.t.

overnight. A saturated solution of NaHCO₃ was added. After stirring for 30 min, the organic layer was separated and washed with water (2×) and dried over anhydrous Na₂SO₄. Filtration and evaporation of solvent gave crude, which was purified by column chromatography on silica gel (50:1-20:1 hexane/EtOAc) to provide pure product (10.0 g) as a white solid.

(f) 1-[3',4'-O-Isopropylidene-6'-O-(4-toluoyl)-β-D-psicofuranosyl]uracil

To a flask with uracil (2.2 g) were added HMDS (15 mL) and TMSCl (2.4 mL). The resulting suspension was heated to 120° C. under N₂ and stirred at this temperature for 4 h. after which the suspension turned to a clear solution. It was cooled to r.t. and the volatile materials were removed in vacuum. The residue was kept under vacuum for 45 min. and then dissolved in dry acetonitrile (25 mL) and transferred to a solution of 6-O-(4-toluoyl)-1,2:3,4-di-O-isopropylidene-D-psicofuranose (4.2 g, 11.1 mmol, 1.0 equiv.) via cannula at rt. The mixture was cooled to 0° C. and TMSOTf (2.96 g, 2.41 mL, 13.31 mmol, 1.2 equiv.) was added by syringe. The solution was allowed to reach r.t. slowly and then stirred overnight. A saturated solution of NaHCO₃ was added drop wise. After stirring for 30 min, water was added. The mixture was extracted with EtOAc (3×). The combined extracts were washed with brine (2×), dried over anhydrous MgSO₄ and filtered. Evaporation of solvent gave the cruden product, which was chromatographyed on silica gel (100:1-40:1 CH₂Cl₂/MeOH) to provide pure 1-[3',4'-O-isopropylidene-6'-O-(4-toluoyl)-α-D-psicofuranosyl]uracil and 1-[3',4'-O-isopropylidene-6'-O-(4-toluoyl)-β-D-psicofuranosyl]uracil (~1:1 ratio, 4.26 g, 88.7% yield) as white solids.

(g) 1-[3',4'-O-Isopropylidene-6'-O-(4-toluoyl)-β-D-psicofuranosyl]-6-iodouracil (Prophetic)

A stirred solution of 1-[3',4'-O-isopropylidene-6'-O-(4-toluoyl)-β-D-psicofuranosyl]-uracil (0.628 mmol) in dry THF (5 mL) is treated with LDA (1.984 mmol, 2.0 M solution in THF) in dry THF (2 mL) at −78° C. After stirring for 1 h, iodine (0.161 g, 0.628 mmol) in dry THF (2 mL) is added and the mixture is stirred for further 5 h at same temperature. The reaction is quenched with AcOH (0.3 mL), then brought to room temperature and dissolved in ethyl acetate (25 mL). The organic layer is washed with saturated NaHCO₃ solution (10 mL), brine (10 mL) and dried (Na₂SO₄). Evaporation of the solvent and purification of crude by column chromatography (hexanes-ethyl acetate, 70:30) gives the title compound.

(h) 1-[1'-O-(t-Butyldimethylsilyl)-3',4'-O-isopropylidene-6'-O-(4-toluoyl)-β-D-psicofuranosyl]-6-iodouracil (Prophetic)

A mixture of compound 1-[3',4'-O-isopropylidene-6'-O-(4-toluoyl)-β-D-psicofuranosyl]-6-iodouracil (1.51 g, 3.48 mmol, 1.0 equiv.), TBDMSCl (0.63 g, 4.18 mmol, 1.2 eq.), imidazole (1.19 g, 17.42 mmol, and DMAP in dry methylene chloride (50 mL) is stirred at r.t. overnight. A saturated solution of NaHCO₃ is added. The organic layer is separated and the aqueous layer is extracted with methylene chloride. The combined organic layers are washed with water, dried over anhydrous MgSO₄, filtered. The solvent is removed to give crude, which is re-crystallized from ethyl acetate/hexane to afford pure product.

(i) 1-[1'-O-(t-Butyldimethylsilyl)-3',4'-O-isopropylidene-β-D-psicofuranosyl]'-6-iodouracil (Prophetic)

1-[1'-O-(t-Butyldimethylsilyl)-3',4'-O-isopropylidene-6'-O-(4-toluoyl)-β-D-psicofuranosyl]-6-iodouracil (1.22 g) is dissolved in 7 N NH₃ in methanol. The solution is stirred at r.t. for 2 days. The solvent was removed under reduced pressure. The residue is purified by column chromatography on silica gel (50:1-20:1 CH₂Cl₂/MeOH) to give pure product.

(j) 1'-Hydroxymethyl-6-iodo-uridine-5'-monophosphate and its Ammonium salt (Ix) (Prophetic)

To a solution of POCl₃ (0.676 g, 4.4 mmol, 4.4 equiv.) in dry acetonitrile (4 mL) is added pyridine (0.380 g, 4.8 mmol, 4.8 equiv.) and water (0.050 g, 2.8 mmol, 2.8 equiv.) at 0° C. After stirring, 1-[1'-O-(t-butyldimethylsilyl)-3',4'-O-isopropylidene-β-D-psicofuranosyl]-6-iodouracil (0.429 g, 1.0 mmol, 1.0 equiv.) is added. The resulting solution is stirred for 4.5 h and ice-water (20 mL) is added. The mixture is stirred for additional 1.5 h and then evaporated under vacuum. The residue is loaded to a basic resin Dowex column. The column is washed with large amount of water (~300 mL) and then with 5% formic acid to yield the product acid. This oil is neutralized carefully with ammonium hydroxide 0.5N at 0° C. and freeze dried to give compound Ix.

Example 10

Synthesis of Compound Iy

Reaction conditions: (a) acetic anhydride, pyridine, r.t. 1 hour.

A stirred mixture of 6-iodouridine (Ii) in 2 mL of dry pyridine (50 mg, 0.135 mmol) was prepared. To this mixture, 0.068 mmol of acetic anhydride in dry pyridine (2 mL) was added. This mixture was stirred for 25 min, and an additional 0.034 mmol of acetic anhydride in dry pyridine (1 mL) was added, followed by an additional 0.017 mmol of acetic anhydride in pyridine (1 mL). After 15 minutes of stirring, the reaction mixture was evaporated to dryness and the product was purified by column chromatography (3% MeOH in CHCl$_3$), to obtain 10 mg (18% yield) of the target compound Iy.

Example 11

Synthesis of Compounds Iz and Iaa

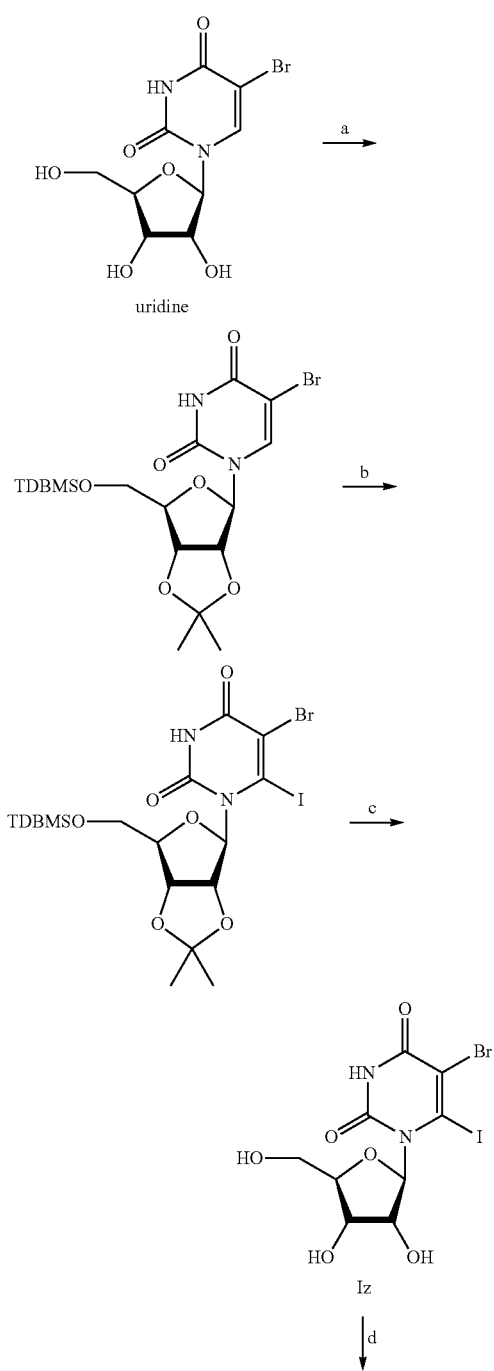

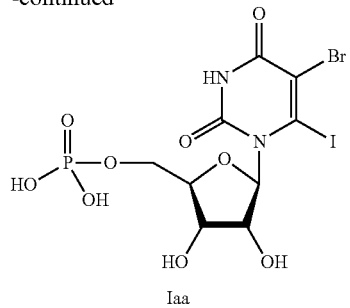

Reaction conditions: (a) i. acetone/H$^+$, ii. TBDMSCl, imidazole/CH$_2$Cl$_2$, 0-25° C.; (b) LDA, I$_2$, THF, -78° C.; (c) 50% TFA, r.t.; (d) POCl$_3$, pyridine, H$_2$O, CH$_3$CN, 0° C.

Compounds Iz and Iaa were synthesized from 5-bromouridine. Introduction of iodo in C-6 position was achieved through LDA and iodine. Deprotection of the protecting groups with TFA followed by the mono-phosphorylation with phosphorus oxychloride afforded the mono-phosphorylated nucleoside. Finally, the monophosphate compound was transformed into the ammonium salt of Iaa by neutralization with a 0.5 M NH$_4$OH solution at 0° C. and freeze dried to get the ammonium salts as powder.

(a) 5'-O-($^t$-Butyldimethylsilyl)2',3'-O-isopropyliden-5-bromo uridine. A stirred suspension of 5-bromouridine (1 g) in dry acetone (50 mL) was treated with H$_2$SO$_4$ (0.5 mL) drop wise at room temperature and the resulting mixture was stirred further 1 h and neutralized with Et$_3$N. Evaporation of the solvent and purification of the crude by column chromatography (5-8% MeOH in CHCl$_3$) gave 2,3-O-isopropyliden-5-bromouridine (1.15 g) in quantitative yield as a white solid. A stirred solution of 2,3-O-isopropyliden-5-bromouridine (0.2 g) in dry CH$_2$Cl$_2$ (3 mL) was treated with imidazole (0.095 g, 1.408 mmol) and TBDMSCl (0.105 g, 0.704 mmol) at 0° C. The reaction mixture was brought to room temperature and stirred for 1 h. The solvent was evaporated under vacuum and the solid was taken into ethyl acetate (30 mL), washed with water (15 mL), brine (15 mL) and dried (Na$_2$SO$_4$). Evaporation of the solvent and purification of crude by column chromatography (5% MeOH in CHCl$_3$) gave the title compound in 96% yield as a foamy solid.

(b) 5'-O-($^t$-Butyldimethylsilyl)-2',3'-O-isopropylidene 5-bromo-6-Iodo-uridine. A stirred solution of 5'-O-($^t$-butyldimethylsilyl)2',3'-O-isopropyliden-5-bromo uridine (0.628 mmol) in dry THF (5 mL) was treated with LDA (1.984 mmol, 2.0 M solution in THF) in dry THF (2 mL) at -78° C. After stirring for 1 h, iodine (0.161 g, 0.628 mmol) in dry THF (2 mL) was added and the mixture was stirred for further 5 h at same temperature. The reaction was quenched with AcOH (0.3 mL), then brought to room temperature and dissolved in ethyl acetate (25 mL). The organic layer was washed with saturated NaHCO$_3$ solution (10 mL), brine (10 mL) and dried (Na$_2$SO$_4$). Evaporation of the solvent and purification of crude by column chromatography (hexanes-ethyl acetate, 70:30) gave the title compound in 90% yield as a foamy yellow solid.

(c) 5-Bromo-6-Iodo uridine (Iz). A stirred solution of 5'-O-($^t$-butyldimethylsilyl)-2',3'-O-isopropylidene 5-bromo-6-Iodo-uridine (0.300 g) was treated with 50% aqueous TFA (3 mL) at 0° C. and then brought to room temperature and stirred for 2 h, light protected. Evaporation of solvent and purification of crude by column chromatography (10-15% EtOH in CHCl$_3$) gave Iz (0.182 g, 0.492 mmol) in 85% yield as a light brown solid.

(d) 5-Bromo-6-Iodo uridine-5'-O-monophosphate, ammonium salt (Iaa). A stirred solution of $H_2O$ (0.034 g, 1.89 mmol) and $POCl_3$ (0.277 mL, 2.973 mmol) in dry acetonitrile (3 mL) was treated with pyridine (0.261 mL, 3.24 mmol) at 0° C. and stirred for 10 min. Compound Iz was added (0.675 mmol) and the mixture was stirred for further 5 h at same temperature. The reaction mixture was quenched with 25 mL of cold water and stirring was continued for further 1 h. Evaporation of solvent and purification of crude by column chromatography (Dowex ion-exchange basic resin, 0.1M formic acid) gave the monopshophate derivative in 61% yield as syrup. Finally, monophosphate compound was transformed into the ammonium salt of Iaa by neutralization with 0.5 M $NH_4OH$ solution at 0° C. and freeze dried to get the ammonium salts as powder.

Example 12

P. falciparum Cultures and CHO Cell Assays

Assays comparing the antiplasmodial activities of the compounds of the invention were performed using the SYBR-Green method.[xlviii] Briefly, the compounds were dissolved in DMSO to achieve a concentration of 10 mg/mL. Fifty microliters of RPMI-A were added to each well in a 96-well plate before 40 μL of RPMI-A and 10 μL of compound solution were added to the first well, the contents of the well were mixed, 50 μL were removed and added to the next well in the series and the process was repeated until the next-to-last well was reached. This produced a plate with a series of two-fold dilutions across it, except for the last well in the series, which contained RPMI-A alone. Fifty microliters of parasite culture (2% hematocrit, 2% parasitemia) were added to each well and the plates were then incubated at 37° C. in 95% $N_2$, 3% $CO_2$, and 2% $O_2$ for 72 hrs.

CHO cells (ATCC, Manassas, Va.) were grown in RPMI-1640 supplemented with 10% fetal calf serum (Sigma, St. Louis, Mo.), 25 mM HEPES and gentimicin (RPMI-10). Cells were seeded in 96 well plates and grown to 50% confluency in 100 μL of RPMI-10 per well prior to the addition of either DMSO alone, or a test compound dissolved in DMSO to a concentration of 10 mg/mL. Compound gradients were prepared by adding 90 μL of RPMI-10 mixed with 10 μL of compound solution to the first well in the series, mixing, transferring 100 μL to next well and repeating until the next-to-last well was reached. After 48 hrs, the viability of the cells was determined by discarding the media in the wells and adding 100 μL of 10 mg/mL of 3-[4,5-dimethylthiazol-2-yl]-2,5-diphenyltetrazolium bromide (MTT, Sigma, St. Louis, Mo.) in RPMI-10, incubating the plates for an additional hour, and then removing the media and adding 100 μL of DMSO and reading the absorbance at 650 nm.[xlix] The $IC_{50}$ values of individual compounds were determined applying a non-linear regression analysis of the dose-response curve using the computer program SigmaPlot (Jandel Scientific).

(a) Enzymology. ODCase from M. thermoautotrophicum (Mt) and compound Id were incubated at room temperature in the reaction buffer (50 mM Tris, 20 mM DTT, 40 mM NaCl, pH 7.5). The concentrations of the Id were 1×, 2.5×, 3.5× and 5× of the enzyme concentration, corresponding to 50, 125, 175 and 250 μM, respectively. The remaining enzyme activity in the enzyme-inhibitor reaction mixture was measured after 30 min, 2, 4, 8, 12, 24, 48 and 96 hours after the onset of incubation. Aliquots (1 μL) were removed from the reaction mixture and diluted to 2.5 mL with the assay buffer (50 mM Tris, 1 mM DTT, pH 7.5). After dilution, the effective enzyme concentration was 20 nM and inhibitor concentrations were: 20, 50, 70, and 100 nM. Each inhibition assay was initiated by an injection of 5 μL of 11.41 mM OMP (prepared in assay buffer). The final substrate (OMP) concentration was 40 μM.

The inhibition of ODCase from P. falciparum (Pf) was assayed in a similar manner. Pf ODCase (50 μM) was incubated in the presence of 0.5×, 1×, 1.2×, and 2× corresponding to 25, 50, 72, and 100 μM, respectively, of test compound. The control reaction contained no test compound. All samples were prepared in 50 mM Tris, 10 mM DTT, 20 mM NaCl, pH 8.0 and incubated at room temperature. The remaining activity of ODCase was measured at 37° C. for up to 48 hrs. At each time point, a 3 μL aliquot of the incubation mixture was diluted with the reaction buffer (50 mM Tris, 1 mM DTT, pH 8.0) to a final volume of 2.5 mL. The reaction was initiated by a single injection of 6 μL of 2.85 mM OMP into the ITC sample chamber. The final substrate concentration was 12 μM.

The Pf ODCase concentration in each of the samples (15, 30, and 45 min incubation times) was 60 nM. Concentrations of the Id were 30, 60, and 72 nM corresponding to 0.5×, 1×, and 1.2× the concentration of enzyme, respectively. The samples were incubated at 37° C. The remaining enzyme activities in these samples were measured by injecting 3 μL of 2.85 mM OMP. The enzyme activity at t=0 was measured by injecting OMP and 6-iodo-UMP simultaneously into the 60 nM enzyme solution in the ITC sample chamber. The solution of the ligands (substrate and test compound) was prepared to yield the final concentrations of 30, 60, and 75 nM of the test compound and 6 μM OMP in the reaction cell after a 3 μL injection. The control sample with 60 nM enzyme was incubated for 15-45 minutes at 37° C., and the enzyme activity was measured after the addition of 3 μL of 2.85 mM OMP.

(b) Data Analysis. Enzyme activity was derived from the linear portions of progress curves from the isotherms obtained from the isothermal titration calorimetry (Power vs time). A covalent inhibition without inhibitor turn-over was assumed in all calculations.

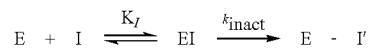

The rate of inhibition (k) at each concentration of the inhibitor was derived from the slope of ln (% enzyme activity) vs time. Enzyme inhibition constants $k_{inact}$ and $K_1$ were derived from the non-linear fit of the slopes to the following equation:

$$k = \frac{k_{inact} \times [I]}{K_I + [I]} \quad (1)$$

where k is the rate of inhibition at a specific inhibitor concentration, $k_{inact}$ is the inactivation rate and $K_1$ is the dissociation constant for inactivation[1].

$$\text{Slope} = \frac{K_I}{k_{inact}} \quad (2)$$

The inactivation rate, $k_{inact}$ is derived from the reciprocal of the y-axis intercept. The inhibition constant for the formation of the reversible complex, $K_1$ is derived form the reciprocal of the negative x-axis.

Half-time of inactivation $t_{1/2}$ was calculated from:

$$t_{1/2} = 0.693/k_{inact} \qquad (3)$$

(c) Crystallographic Analysis. All Mt ODCase concentrations were determined using a BioRAD protein assay kit and BSA as a standard. ODCase (10 mg/mL) with 6-iodo-UMP (Id, 10 mM) was prepared in crystallization buffer composed of 20 mM HEPES-NaOH at pH 7.5, 150 mM sodium chloride and 5 mM DTT. This protein solution (2 µL) was mixed with 2 µL of reservoir solution containing 1.1-1.3 M sodium citrate, 5% (v/v) dioxane and 100 mM MES at pH 6.5 and then set up for crystallization using the hanging drop technique. The following day, microseeding started the formation of diffraction-quality crystals, which took about a week to reach their full size. When harvested, crystals were immediately dipped into mother liquor supplemented with 15% (v/v) glycerol for cryo-protection, then flash-frozen in a stream of dry nitrogen at 100 K. Diffraction data were collected to 1.6 Å resolution at beamline 14BM-C BioCARS, Advanced Photon Source, IL, USA. The data collected were reduced using the programs DENZO, SCALEPACK and TRUNCATE from the CCP4 program suite.[li,lii] The crystals belonged to space group P2$_1$ with unit cell parameters, a=57.8 Å, b=73.3 Å, c=59.1 Å, β=119.3°. Phases were calculated based on the coordinates of the Mt ODCase-BMP complex (PDB code: 1X1Z). An atomic model was constructed with the help of the program O and refined using the program CNS, version 1.1 resulting in final $R_{crystal}$ and $R_{free}$ factors of 15.9% and 18.7%, respectively.[liii,liv] Data collection and final refinement statistics are shown in Table S1. Atomic coordinates and structure factors have been deposited into the Protein Data Bank.

(d) Primary Blood Cells Assays.

The following procedure was used to conduct human primary blood cell assays. Added 3 ml of PBS (OCI media facility) to 3 ml of serum depleted blood from normal, adult, human controls. Pipetted 6 ml Ficoll-Paque Plus (Amersham 17-1440-03) into a 15 ml centrifuge tube. Overlaid with PBS diluted blood. Centrifuged at 2500 rpm for 10 minutes at room temperature, no brake.

Removed and discarded upper (PBS) phase. Transferred cells at the PBS/Ficoll interface to a clean 15 ml centrifuge tube. Added 10 mL PBS. Then, centrifuged at 1250 rpm for 10 minutes at room temperature.

Discarded the supernatant and resuspended the cell pellet in Iscove's Modified Dulbecco's Medium (Gibco 12440 prepared by OCI Media facility) supplemented with 5.5×10-5M 2ME (Fisher 03446-100) and 5% FBS (Hyclone SH-30397-03 Lot # KPG21604). Plated cells at 50,000 cells per well in 96 well flat bottom plates (Costar 3595). Added Concanavalin A (Pharmacia 17-0450-01) to a final concentration of 1.5 micro gm/ml. All conditions were set in triplicate.

Included untreated (Con A alone) controls. Cultured cells for 48 hours or 72 hours at 37° C. with 5% $CO_2$ and 90% relative humidity. Added 0.5 uCi H-3 (Perkin Elmer NET027A) per well in 10 microL for the last 8 hours of the culture period. Transferred wells to Unifilter-96 GFC plates (Perkin Elmer 6005174).

Dried plates for 1 hour at 37° C. Added 25 microL Microscint 0 scintillation fluid (Perkin Elmer 6013611) per well. Data was collected by reading the radioactivity counts.

(e) Mouse Efficacy Studies Against Plasmodia:

*P. chabaudi chabaudi* (Pcc) AS infection: They are two different species of mouse malaria that are used commonly in mice efficacy studies: *P. chabaudi chabaudi* AS and *P. burghei*. Pcc strain induces larger load of parasites and even some mouse strains die. If *P. burghei* strain is given to the mouse, they develop fewer parasites but become very sick. Pcc strain provides an opportunity in mice to observe if parasite numbers are reduced in the context of a reasonably healthy animal. Thus, Pcc strain was used in the efficacy model.

Blood-stage PCCAS was maintained in as described (Podoba J E and Stevenson, 1991)[2]. Infections in experimental animals were initiated by intraperitoneal injection of 1×10$^6$ *P. chabaudi chabaudi* AS-infected erythrocytes (PC-CAS). Course of infection was monitored daily for 18 days by determining parasitemia on thin-blood smears stained with Diff Quik (American Scientific Products, Mississauga, ON). Compounds to be assayed were made up in RPMI 1640 at the concentration required to deliver the target dose in a total volume of 0.5 mL and were then filter sterilized. Compounds were stored at 4° C. prior to use. After infection the presence of parasites in the peripheral circulation was monitored daily until parasites were first observed. The mice were then injected daily for three consecutive days with either RPMI 1640 alone or compound dissolved in RPMI. The health of the animals was assessed daily and the parasitemia determined by examining blood films. Animals that were inactive and considered to be terminally ill were euthanized promptly.

(f) Results

Figure 4:
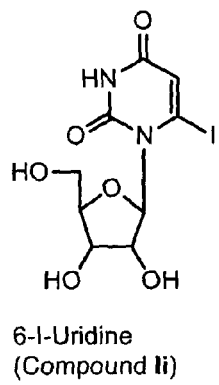
FIG. 4 shows inhibition curves when *P. faliciparum* was treated with compound Ii, against 3D7 and ItG isolates as well as against CHO cell lines.
Figure 4:
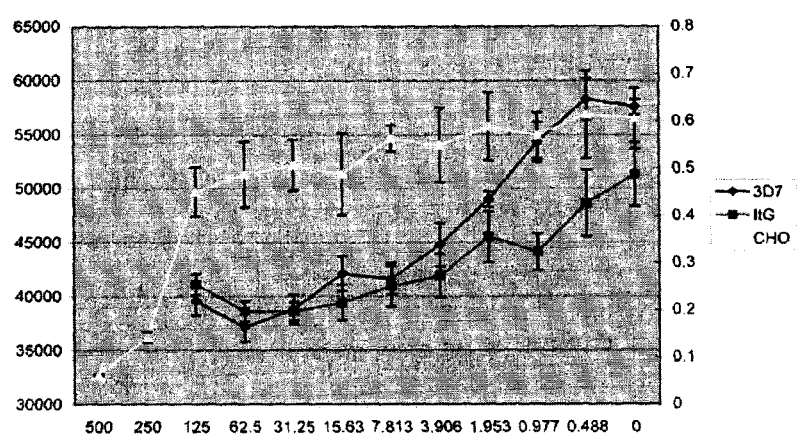

It was found that compound Ii in in vitro antiparasitic activity evaluations exhibited potent anti-plasmodial activity, with IC$_{50}$ of 4.4±1.3 mM and 6.2±0.7 mM against *P. falciparum* ItG and 3D7 isolates, respectively (FIG. 4). Thus, compound Ii is a covalent inhibitor of ODCase and its nucleoside analog paves way to a new class of inhibitors against malaria. The toxicities to Chinese hamster ovary (CHO), Vero and human fibroblast (HFF) cell lines for compound Ii were 366±45 mM (IC$_{50}$), >300 mM (CC$_{50}$) and >300 mM (IC$_{50}$), respectively. Additionally, toxicity on human primary blood cells (PBLs) was also not observed up to 200 mM. These results show that compound Ii may be phosphorylated to its monophosphate derivative Ij and inhibits the parasite (in vitro and in vivo).

Figure 5:
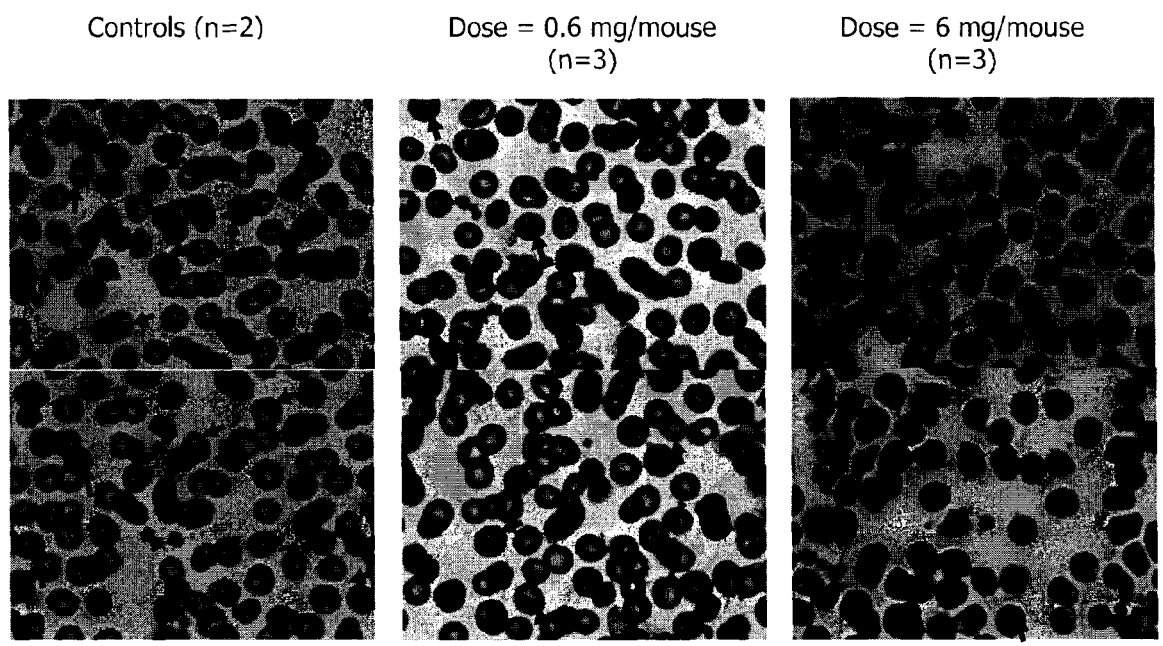
FIG. 5 shows pictures of parasitemia in the mice blood during in vivo efficacy studies in mice using compound Ii. Arrows point to parasite-infected blood cells from the mice.
Figure 6:
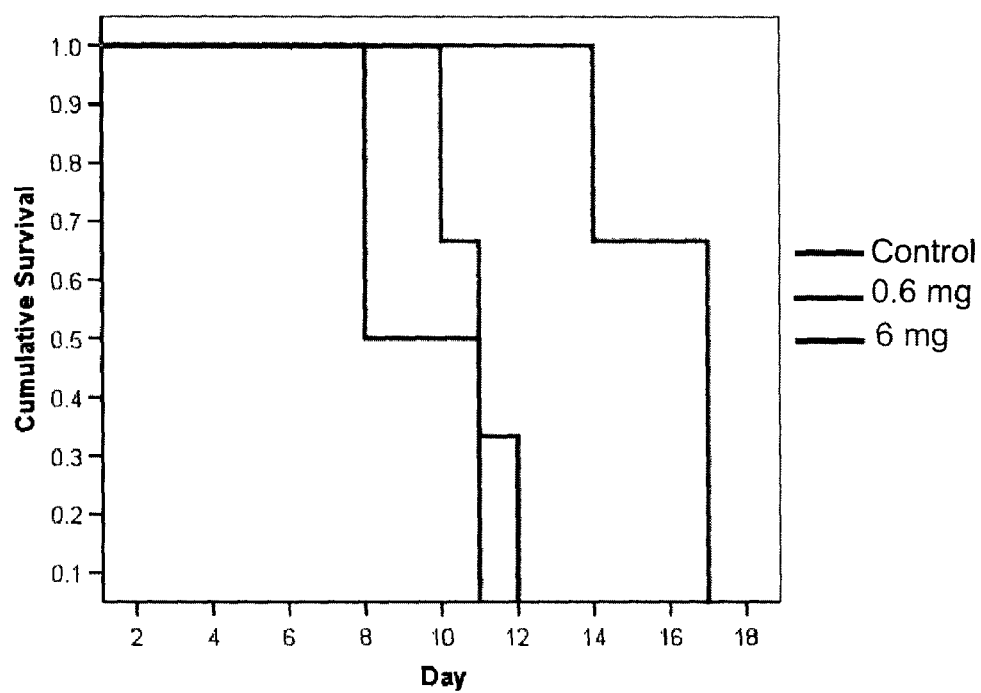
FIG. 6 shows survival rates in mice infected with *P. ubrghei* and when treated with compound Ii.
Figure 7:
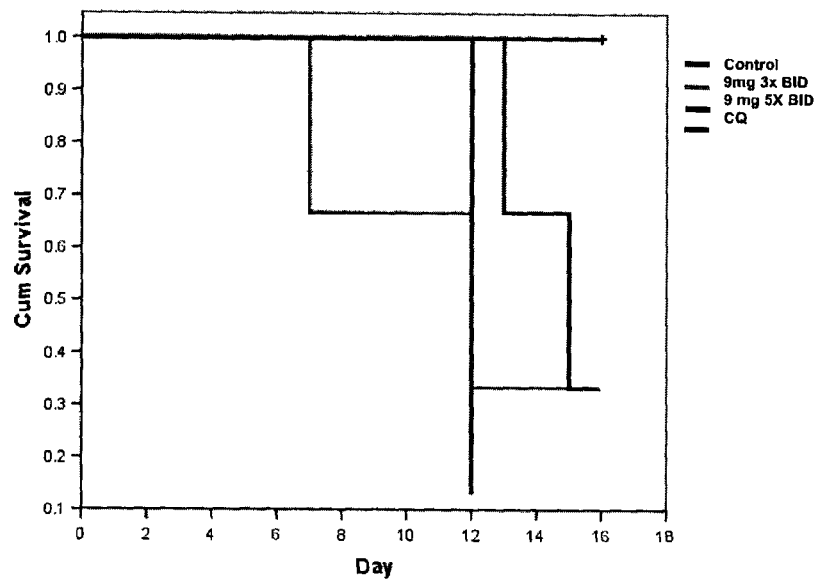
FIG. 7 shows the results of a mouse efficacy study with multiple dosing using treatment with compounds Ii.

Efficacy studies in mice were performed using Ii to test the in vivo potential of this compound. Mice were infected with *P. burghei*, a mouse strain similar to the human malaria parasite *P. falciparum*. *P. burghei* strain is approximately 20 times less sensitive to Ii, so the dose in mice had to be adjusted accordingly. Parasitemia was monitored in mice after the drug was given at two different doses: 0.6 mg/mouse (n=3) and 6 mg/mouse (n=3). There was a control group of mice without any treatment with Ii. FIG. 5 shows the decreased parasitemia in drug-treated mice in comparison to the controls, and this is dose-dependent. FIG. 6 depicts the plot of survival rate in Ii treated animals vs controls, and clearly corroborates the decreased parasitemia with that of the longer survival time, when treated with Ii. Above FIG. 7 confirms that higher doses of Ii enhance the efficacy of this compound against malaria, with increased survival of the treated animals in comparison to those without any drug.

Compounds Ia, Ib, Ic, Id, Ie, If, Ij, Ip, Io, In and It were all tested for anti-malarial activity against *Plasmodium falciparum* and *Plasmodium vivax*. These compounds showed IC$_{50}$'s in the range of about 20 µM to about 2000 µM.

While the present invention has been described with reference to what are presently considered to be the preferred examples, it is to be understood that the invention is not limited to the disclosed examples. To the contrary, the invention is intended to cover various modifications and equivalent arrangements included within the spirit and scope of the appended claims.

All publications, patents and patent applications are herein incorporated by reference in their entirety to the same extent as if each individual publication, patent or patent application was specifically and individually indicated to be incorporated by reference in its entirety. Where a term in the present application is found to be defined differently in a document incorporated herein by reference, the definition provided herein is to serve as the definition for the term.

FULL CITATIONS FOR DOCUMENTS REFERRED TO IN THE SPECIFICATION i. Warshel, A.; Florian, J. Computer simulations of enzyme catalysis: finding out what has been optimized by evolution. *Proc. Natl. Acad. Sci. U.S.* 1998, 95, 5950-5955.

[ii]. Radzicka, A.; Wolfenden, R. A proficient enzyme. *Science* 1995, 267, 90-93.

[iii]. Miller, B. G.; Wolfenden, R. Catalytic proficiency: The unusual case of OMP decarboxylase. *Ann. Rev. Biochem.* 2002, 71, 847-885.

[iviv]. Sievers, A.; Wolfenden, R. Equilibrium of formation of the 6-carbanion of UMP, a potential intermediate in the action of OMP decarboxylase. *J. Am. Chem. Soc.* 2002, 124, 13986-13987.

v. Snider, M. J.; Wolfenden, R. The rate of spontaneous decarboxylation of amino acids. *J. Am. Chem. Soc.* 2000, 122, 11507-11508.

[vi]. Schutz A. G. R.; Konig, S.; Hubner, G.; Tittmann, K. Intermediates and transition states in thiamin diphosphate-dependent decarboxylases. A kinetic and NMR study on wild-type indolepyruvate decarboxylase and variants using indolepyruvate, benzoylformate, and pyruvate as substrates. *Biochemistry* 2005, 44, 6164-6179.

[vii]. Tittmann, K.; Golbik, R.; Uhlemann, K.; Khailova, L.; Schneider, G.; Patel, M.; Jordan, F.; Chipman, D. M.; Duggleby, R. G.; Hübner, G. NMR analysis of covalent intermediates in thiamin diphosphate enzymes. *Biochemistry* 2003, 42, 7885-7891.

[viii]. Reichard, P. The enzymatic synthesis of pyrimidines. *Adv. Enzymol. Mol. Biol.* 1959, 21, 263-294.

[ix]. Donovan, W. P.; Kushnerm, S. R. Purification and characterization of orotidine-5'-monophosphate decarboxylase from *Escherichia coli* K-12. *J. Bacteriol.* 1983, 156, 620-624.

[x]. Pragobpol, S.; Gero, A. M.; Lee, C. S.; O'Sullivan, W. J. Orotate phosphoribosyltransferase and orotidylate decarboxylase from *Crithidia luciliae*: Subcellular location of the enzymes and a study of substrate channeling. *Arch. Biochem. Biophys.* 1984, 230, 285-293.

[xi]. Kotra, L. P.; Pai, E. F.; Bello, A. M.; Fujihashi, M.; Poduch, E. (2005) Inhibitors of orotidine monophosphate decarboxylase (ODCase) activity, U.S. Application No. 60/596, 537, patent pending.

[xii]. Christopherson, R. I.; Lyons, S. D.; Wilson, P. K. Inhibitors of de Novo nucleotide biosynthesis as drugs. *Acc. Chem. Res.* 2002, 35, 961-971.

[xiii]. Scott, H. V.; Gero, A. M.; O'Sullivan, W. J. In vitro inhibition of *Plasmodium falciparum* by pyrazofurin, an inhibitor of pyrimidine biosynthesis de novo. *Mol. Biochem. Parasitol.* 1986, 18, 3-15.

[xiv]. Levine, H. L.; Brody, R. S.; Westheimer, F. H. Inhibition of orotidine-5'-phosphate decarboxylase by 1-(5'-phospho-beta-d-ribofuranosyl)barbituric acid, 6 azauridine 5'-phosphate, and uridine 5'-phosphate, *Biochemistry* 1980, 19, 4993-4999.

[xv]. Harris, P.; Poulsen, J. C. N.; Jensen, K. F.; Larsen, S. Substrate binding induces domain movements in orotidine 5'-monophosphate decarboxylase. *J. Mol. Biol.* 2002, 318, 1019-1029.

[xvi]. Wu, N.; Mo, Y.; Gao, J.; Pai, E. F. Electrostatic stress in catalysis: structure and mechanism of the enzyme orotidine monophosphate decarboxylase. *Proc. Natl. Acad. Sci. USA* 2000, 97, 2017-2022.

[xvii]. Appleby, T. C.; Kinsland, C.; Begley, T. P.; Ealick, S. E. The crystal structure and mechanism of orotidine 5'-monophosphate decarboxylase. *Proc. Natl. Acad. Sci. USA* 2000, 97, 2005-2010.

[xviii]. Miller, B. G.; Hassell, A. M.; Wolfenden, R.; Milburn, M. V.; Short, S. A. Anatomy of a proficient enzyme: the structure of orotidine 5'-monophosphate decarboxylase in the presence and absence of a potential transition state analog. *Proc. Natl. Acad. Sci. USA* 2000, 97, 2011-2016.

[xix]. Lee, T. S.; Chong, L. T.; Chodera, J. D.; Kollman, P. A. An alternative explanation for the catalytic proficiency of orotidine 5'-phosphate decarboxylase. *J. Am. Chem. Soc.* 2001, 123, 12837-12848.

[xx]. Miller, B. G.; Butterfoss, G. L.; Short, S. A.; Wolfenden, R. Role of enzyme-ribofuranosyl contacts in the ground state and transition state for orotidine 5'-phosphate decarboxylase: a role for substrate destabilization? *Biochemistry* 2001, 40, 6227-6232.

[xxi]. Warshel, A.; Strajbl, M.; Villa, J.; Florian, J. Remarkable rate enhancement of orotidine 5'-monophosphate decarboxylase is due to transition-state stabilization rather than to ground-state destabilization. *Biochemistry* 2000, 39, 14728-14738.

[xxii]. Harris, P.; Navarro Poulsen, J. C.; Jensen, K. F.; Larsen, S. Structural basis for the catalytic mechanism of a proficient enzyme: orotidine 5'-monophosphate decarboxylase. *Biochemistry* 2000, 39, 4217-4224.

[xxiii]. Jencks, W. P. Binding energy, specificity, and enzymic catalysis: the Circe effect. *Adv. Enzymol. Related Areas Mol. Biol.* 1975, 43, 219-410.

[xxiv]. Miller, B. G.; Snider, M. J.; Short, S. A.; Wolfenden, R. Contribution of enzyme-phosphoribosyl contacts to catalysis by orotidine 5'-phosphate decarboxylase. *Biochemistry* 2000, 39, 8113-8118.

[xxv]. Amyes, T. L.; Richard, J. P.; Tait, J. J. Activation of orotidine 5'-monophosphate decarboxylase by phosphate dianion: the whole substrate is the sum of two parts. *J. Am. Chem. Soc.* 2005, 127, 15708-15709.

[xxvi]. Gero, A. M.; O'Sullivan, W. J. Purines and pyrimidines in malarial parasites, *Blood Cells* 1990, 16, 467-484.

[xxvii]. Jones, M. E. Pyrimidine nucleotide biosynthesis in animals: Genes, enzymes, and regulation of UMP biosynthesis, *Annu. Rev. Biochem.* 1980, 49, 253-279.

[xxviii]. Seymour, K. K.; Lyons, S. D.; Phillips, L.; Rieckmann, K. H.; Christopherson, R. I. Cytotoxic effects of inhibitors of de novo pyrimidine biosynthesis upon *Plasmodium falciparum*, *Biochemistry* 1994, 33, 5268-5274.

[xxix]. Krungkrai, J.; Krungkrai, S. R.; Phakanont, K. Antimalarial activity of orotate analogs that inhibit dihydroorotase and dihydroorotase dehydrogenase. *Biochem. Pharmacol.* 1992, 43, 1295-1301.

[xxx]. Hirota, K.; Tomishi, T.; Maki, Y.; Sajiki, H. *Nucleosides & Nucleotides* 1998, 17, 161-173.

[xxxv]. Tanaka, H.; Hayakawa, H.; Haraguchi, K.; Miyasaka, T. Introduction of an azido group to the C-6 position of uridine by the use of a 6-iodouridine derivative. *Nucleosides & Nucleotides* 1985, 4, 607-612.

[xxxvi]. Tanaka, H.; Hayakawa, H.; Miyasaka, T. "Umpolung" of reactivity at the C-6 position of uridine: a simple and general method for 6-substituted uridines, *Tetrahedron* 1982, 38, 2635-2642.

xxxvii. Sowa, T.; Ouchi, S. Facile synthesis of 5'-nucleotides by selective phosphorylation of a primary hydroxyl group of nucleosides with phosphoryl chloride. *Bull. Chem. Soc. Jpn.* 1975, 48, 2084-2090.

xxxviii. Ueda, T.; Yamamoto, M.; Yamane, A.; Imazawa, M.; Inoue, H. Conversion of uridine nucleotides to the 6-cyano derivatives: synthesis of orotidylic acid. *Carbohyd. Nucleosides Nucleotides* 1978, 5, 261-271.

xxxix. Poduch, E.; Bello, A. M.; Tang, S.; Fujihashi, M.; Pai, E. F.; Kotra, L. P. *J. Med. Chem.* 2006, 49, 4937-4935.

xl. Tanaka, H.; Hayakawa, H.; Haraguchi, K.; Miyasaka, T. *Nucleosides & Nucleotides* 1985, 4, 607-612.

xli. Tanaka, H.; Hayakawa, H.; Miyasaka, T. *Tetrahedron* 1982, 38, 2635-2642.

xlii. Sowa, T.; Ouchi, S. *Bull. Chem. Soc. Jpn.* 1975, 48, 2084-2090.

xliii. Ueda, T; Yamamoto, M.; Yamane, A.; Imazawa, M.; Inoue, H. *Carbohyd. Nucleosides Nucleotides* 1978, 5, 261-271.

xliv. Tanaka, H.; Hayakawa, H.; Haraguchi, K.; Miyasaka, T. Introduction of an azido group to the C-6 position of uridine by the use of a 6-iodouridine derivative. *Nucleosides Nucleotides* 1985, 4, 607-612.

xlv. Tanaka, H.; Hayakawa, H.; Miyasaka, T. "Umpolung" of reactivity at the C-6 position of uridine: a simple and general method for 6-substituted uridines. *Tetrahedron* 1982, 38, 2635-2642.

xlvi. Sowa, T.; Ouchi, S. Facile synthesis of 5'-nucleotides by selective phosphorylation of a primary hydroxyl group of nucleosides with phosphoryl chloride. *Bull. Chem. Soc. Jpn.* 1975, 48, 2084-2090.

xlvii. Ueda, T; Yamamoto, M.; Yamane, A.; Imazawa, M.; Inoue, H. Conversion of uridine nucleotides to the 6-cyano derivatives: synthesis of orotidylic acid. *Carbohyd. Nucleosides Nucleotides* 1978, 5, 261-271.

xlviii. Smilkstein, M.; Sriwilaijaroen, N.; Kelly, J. X.; Wilairat, P.; Riscoe, M. Simple and inexpensive fluorescence-based technique for high-throughput anti-malarial drug screening. *Antimicrob. Agents Chemother.* 2004, 48, 1803-1806.

xlix. Campling, B. G.; Pym, J.; Galbraith, P. R.; Cole, S. P. Use of MTT assay for rapid determination of chemosensitivity of human leukemic blast cells. *Leukemia Res.* 1988, 12, 823-831.

(l) Alejandro G. Marangoni, Enzyme Kinetics: A Modern Approach. John Wiley & Sons. Inc. 2003.

(li) Otwinowski, Z.; Minor, W., Processing of X-ray Diffraction Data Collected in Oscillation Mode. In *Macromolecular Crystallography, Part A*, Carter, C. W., Jr.; Sweet, R. M., Eds. Academic Press: 1997; Vol. 276, pp 307-326.

(lii) Collaborative Computational Project, N. The CCP4 suite: programs for protein crystallography. *Acta Crystallogr D Biol Crystallogr* 1994, 50, 760-763.

(liii) Jones, T. A.; Zou, J.-Y.; Cowan, S. W. Improved Methods for Building Protein Models in Electron Density Maps and the Location of Errors in these Models. *Acta Crystallogr A* 1991, 47, 110-119.

(liv) Brunger, A. T.; Adams, P. D.; Clore, G. M.; DeLano, W. L.; Gros, P.; Grosse-Kunstleve, R. W.; Jiang, J. S.; Kuszewski, J.; Nilges, M.; Pannu, N. S.; Read, R. J.; Rice, L. M.; Simonson, T.; Warren, G. L. Crystallography & NMR system: A new software suite for macromolecular structure determination. *Acta Crystallogr D Biol Crystallogr* 1998, 54 Part 5, 905-921.

We claim:

1. A method of treating or preventing malaria comprising administering to a subject in need thereof a anti-malarial effective amount of a compound selected from a compound of Formula I, tautomers thereof and pharmaceutically acceptable salts, solvates, and prodrugs thereof:

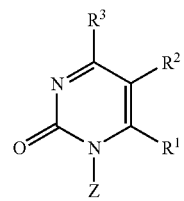

(I)

wherein, $R^1$ is selected from CN, $N_3$, I, Br, $NH_2$, $NO_2$, $C(O)C_{1-6}$alkyl, $NH_1$—$C_6$alkyl, $N(C_1-C_6alkyl)_2$, $NHC(O)C_1-C_6$alkyl and $NHC(O)OC_1-C_6$alkyl;

$R^2$ is selected from H, halo, $C_1-C_6$alkyl, $C_1-C_6$alkoxy, fluoro-substituted-$C_1-C_6$alkyl, fluoro-substituted-$C_1-C_6$alkoxy, $N_3$, $NH_2$ and CN;

$R^3$ is selected from OH, $NH_2$, H and $NHC(O)C_1-C_6$alkyl;

Z is selected from:

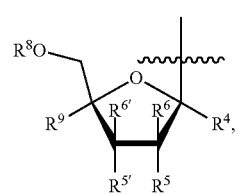

II

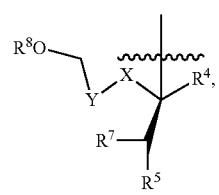

III

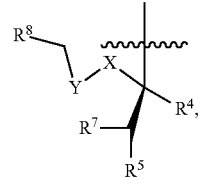

IV

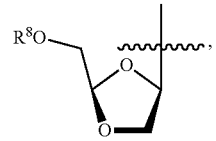

V

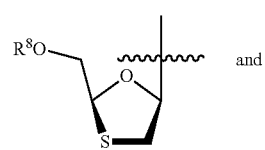

VI

-continued

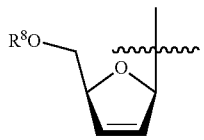
VII wherein,
R⁴ is selected from H, $C_1$-$C_6$alkyl and hydroxy-substituted-$C_1$-$C_6$alkyl;
One of R⁵ and R⁶ is hydrogen and the other is selected from H, OH and F and one of R⁵' and R⁶' is hydrogen and the other is selected from H, OH and F or R⁵ and R⁶ or R⁵' and R⁶' together is =O or =CH₂;
R⁷ is selected from H, F and OH;
R⁸ is selected from H, C(O)$C_1$-$C_6$alkyl, P(O)(OH)₂, P(O)(O$C_1$-$C_6$alkyl)₂ and P(O)(O$C_1$-$C_6$alkyl)OH;
R⁹ is selected from H, N₃, CN, $C_1$-$C_6$alkyl; and
X—Y is selected from —CH₂—O—, —O—CH₂— and —S—CH₂—.

2. The method according to claim 1, wherein R¹ in the compounds of Formula I is selected from I, Br, NO₂, N($C_1$-$C_4$alkyl)₂, NHC(O)$C_1$-$C_4$alkyl and NHC(O)O$C_1$-$C_4$alkyl.

3. The method according to claim 2, wherein R¹ in the compounds of Formula I is selected from I, Br, NO₂, N(CH₃)₂, NHC(O)CH₃ and NHC(O)CH₃.

4. The method according to claim 3, wherein R¹ in the compounds of Formula I is selected from I, Br and N(CH₃)₂.

5. The method according to claim 4, wherein R¹ in the compounds of Formula I is I.

6. The method according to claim 1, wherein R² in the compounds of Formula I is selected from H, halo, $C_1$-$C_4$alkyl, $C_1$-$C_4$alkoxy, fluoro-substituted-$C_1$-$C_4$alkyl, fluoro-substituted-$C_1$-$C_4$alkoxy, N₃, NH₂ and CN.

7. The method according to claim 6, wherein R² in the compounds of Formula I is selected from H, fluoro, chloro, bromo, CH₃, OCH₃, CF₃, CF₃O, N₃, NH₂ and CN.

8. The method according to claim 7, wherein R² in the compounds of Formula I is selected from H, fluoro, chloro, bromo, OCH₃ and CF₃, CF₃O.

9. The method according to claim 1, wherein R³ in the compounds of Formula I is selected from OH and NH₂.

10. The method according to claim 9, wherein R³ in the compounds of Formula I is OH and the compound of Formula I has the following tautomeric structure:

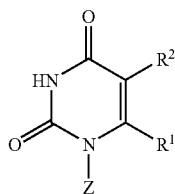

11. The method according to claim 1, wherein in the compounds of Formula I, Z is Formula II.

12. The method according to claim 1, wherein R⁴ in the compounds of Formula I is H.

13. The method according to claim 1, wherein, R⁵ and R⁵' are both OH and R⁶ and R⁶' are both H.

14. The method according to claim 1, wherein R⁵ is H, R⁵' is OH and R⁶ and R⁶' are both H.

15. The method according to claim 1, wherein R⁷ in the compounds of Formula I is H or OH.

16. The method according to claim 1, wherein R⁸ in the compounds of Formula I is selected from H, C(O)$C_1$-$C_4$alkyl, P(O)(OH)₂, P(O)(O$C_1$-$C_4$alkyl)₂ and P(O)(O$C_1$-$C_4$alkyl)OH.

17. The method according to claim 16, wherein R⁸ in the compounds of Formula I is selected from H, C(O)CH₃, P(O)(OH)₂, P(O)(OCH₃)₂ and P(O)(OCH₃)OH.

18. The method according to claim 17, wherein R⁸ in the compounds of Formula I is selected from H, C(O)CH₃, and P(O)(OH)₂.

19. The method according to claim 1, wherein R⁹ in the compounds of Formula I is H.

20. The method according to claim 1, wherein X—Y is —O—CH₂—.

21. The method according to claim 1, wherein the compound of Formula I has the following structure:

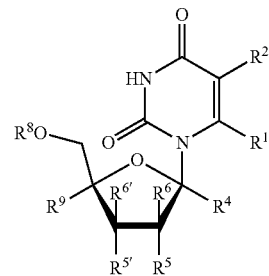
I

22. The method according to claim 1, wherein the compound of Formula I is selected from the group consisting of:
6-Cyanouridine;
6-Cyanouridine-5'-monophosphate;
6-Azido uridine;
6-Azido uridine-5'-O-monophosphate;
6-Amino uridine-5'-O-monophosphate;
6-Amino uridine;
6-Methyl uridine;
6-Methyl uridine-5'-O-monophosphate;
6-Iodo-uridine;
6-N-Methylamino uridine;
6-N,N-Dimethylamino uracil;
6-N,N-Dimethylamino uridine;
6-N-Methylamino uridine-5'-O-monophosphate;
6-Iodo uridine-5'-O-monophosphate;
5-Fluoro-6-amino uridine;
5-Bromo-6-iodo uridine;
5-Fluoro-6-azido uridine;
5-Fluoro-6-iodo uridine;
5-Fluoro-6-amino uridine-5'-O-monophosphate;
5-Bromo-6-iodo uridine-5'-O-monophosphate;
5-Fluoro-6-azido uridine-5'-O-monophosphate;
5-Fluoro-6-iodo uridine-5'-O-monophosphate;
6-Methoxycarbonyl uridine;
6-Ethoxycarbonyl uridine;
6-Methoxycarbonyl uridine-5'-O-monophosphate;
6-Ethoxycarbonyl uridine-5'-O-monophosphate;
11-Hydroxymethyl-6-iodo-uridine;
11-Hydroxymethyl-6-iodo-uridine-5'-monophosphate, and
pharmaceutically acceptable salts, solvates, and prodrugs thereof.

23. A method of preventing or treating an infection of a malarial parasite in a subject comprising administering to the subject an anti-malarial effective amount of a compound of Formula I, and pharmaceutically acceptable salts, solvates, and prodrugs thereof, wherein the compound of Formula I is as defined in claim 1.

24. A method of inhibiting ODCase in a plasma or blood sample isolated from a subject comprising adding to said plasma or blood sample an inhibiting effective amount of a compound of Formula I as defined above, and pharmaceutically acceptable salts, solvates, and prodrugs thereof, wherein the compound of Formula I is as defined in claim 1.

25. A compound of Formula I, wherein Formula I is as defined in claim 1, selected from the group consisting of:
  6-(dimethylamino) uridine;
  5-fluoro-6-amino uridine;
  5-bromo-6-amino uridine;
  5-fluoro-6-azido uridine;
  1'-Hydroxymethyl-6-iodo-uridine;
  6-(dimethylamino) 2'-deoxyuridine;
  5-fluoro-6-amino 2'-deoxyuridine;
  5-bromo-6-amino 2'-deoxyuridine;
  5-fluoro-6-azido 2'-deoxyuridine;
  5-chloro-6-iodo 2'-deoxyuridine;
  5-chloro-6-azido 2'-deoxyuridine;
  5-methoxy-6-iodo 2'-deoxyuridine;
  5-methoxy-6-azido 2'-deoxyuridine;
  5-methoxy-6-amino 2'-deoxyuridine;
  5-bromo-6-iodo 2'-deoxyuridine;
  5-bromo-6-azido 2'-deoxyuridine;
  6-(dimethylamino) uridine 5'-monophosphate;
  5-fluoro-6-amino uridine 5'-monophosphate;
  5-bromo-6-amino uridine 5'-monophosphate;
  5-fluoro-6-azido uridine 5'-monophosphate;
  1'-Hydroxymethyl-6-iodo-uridine-5'-monophosphate
  6-(dimethylamino) 2'-deoxyuridine 5'-monophosphate;
  5-fluoro-6-amino 2'-deoxyuridine 5'-monophosphate;
  5-bromo-6-amino 2'-deoxyuridine 5'-monophosphate;
  5-fluoro-6-azido 2'-deoxyuridine 5'-monophosphate;
  5-chloro-6-iodo 2'-deoxyuridine 5'-monophosphate;
  5-chloro-6-azido 2'-deoxyuridine 5'-monophosphate;
  5-methoxy-6-iodo 2'-deoxyuridine 5'-monophosphate;
  5-methoxy-6-azido 2'-deoxyuridine 5'-monophosphate;
  5-methoxy-6-amino 2'-deoxyuridine 5'-monophosphate;
  5-bromo-6-iodo 2'-deoxyuridine 5'-monophosphate;
  5-bromo-6-azido 2'-deoxyuridine 5'-monophosphate;
  5-fluoro-6-iodo uridine 5'-monophosphate;
  6-iodo uridine 5'-acetate;
  6-iodo 2'-deoxyuridine 5'-acetate, and
pharmaceutically acceptable salts, solvates, and prodrugs thereof.

26. A pharmaceutical composition comprising one or more of a compound according to claim 25 and a pharmaceutically acceptable carrier therefore.

* * * * *